United States Patent [19]
Bito

[11] Patent Number: 6,019,720
[45] Date of Patent: Feb. 1, 2000

[54] SYSTEM FOR EVULSING SUBCUTANEOUS TISSUE

[75] Inventor: Shiro Bito, Tokyo, Japan

[73] Assignee: Olympus Optical Co., Ltd., Tokyo, Japan

[21] Appl. No.: 09/023,540

[22] Filed: Feb. 13, 1998

Related U.S. Application Data

[62] Division of application No. 08/676,856, Jul. 3, 1996, Pat. No. 5,759,150.

[30] Foreign Application Priority Data

| Jul. 7, 1995 | [JP] | Japan | 7-172140 |
| Jul. 7, 1995 | [JP] | Japan | 7-172342 |
| Jul. 7, 1995 | [JP] | Japan | 7-172467 |
| Sep. 29, 1995 | [JP] | Japan | 7-253310 |
| Feb. 19, 1996 | [JP] | Japan | 8-030424 |
| Feb. 20, 1996 | [JP] | Japan | 8-031690 |
| Jun. 26, 1996 | [JP] | Japan | 8-166063 |

[51] Int. Cl.⁷ ............................................. A61B 1/04
[52] U.S. Cl. ..................... 600/123; 600/104; 600/127; 600/129
[58] Field of Search .................. 600/104, 105, 600/121, 123, 127, 129, 135; 606/39, 40, 45, 46, 47, 48, 49, 50

[56] References Cited

U.S. PATENT DOCUMENTS

| 3,967,092 | 6/1976 | Conta et al. . |
| 4,055,743 | 10/1977 | Conta et al. . |
| 4,130,752 | 12/1978 | Conta et al. . |
| 4,469,091 | 9/1984 | Slanetz, Jr. . |
| 4,793,346 | 12/1988 | Mindich . |
| 4,947,185 | 8/1990 | Mitsushima et al. . |
| 4,960,106 | 10/1990 | Kubokawa et al. . |
| 5,092,693 | 3/1992 | Uchimura . |
| 5,271,380 | 12/1993 | Riek et al. . |
| 5,318,582 | 6/1994 | Chow . |
| 5,346,503 | 9/1994 | Chow . |
| 5,356,419 | 10/1994 | Chow . |
| 5,373,840 | 12/1994 | Knighton . |
| 5,385,572 | 1/1995 | Nobles et al. . |
| 5,431,151 | 7/1995 | Riek et al. . |
| 5,540,711 | 7/1996 | Kieturakis et al. ................. 606/190 X |
| 5,591,183 | 1/1997 | Chin ................................. 606/167 X |
| 5,593,418 | 1/1997 | Mollenauer ........................ 606/191 X |
| 5,601,581 | 2/1997 | Fogarty et al. ......................... 606/159 |
| 5,607,441 | 3/1997 | Sierocuk et al. .................... 606/192 X |
| 5,634,935 | 6/1997 | Taheri ................................... 606/190 |

FOREIGN PATENT DOCUMENTS

| 0 484 725 A1 | 5/1992 | European Pat. Off. . |
| 61-7686 | 3/1986 | Japan . |
| 4-10328 | 2/1992 | Japan . |
| 4-17648 | 3/1992 | Japan . |
| 5-161660 | 6/1993 | Japan . |
| 7-172139 | 4/1996 | Japan . |
| 8-117181 | 5/1996 | Japan . |
| 94/11052 | 5/1994 | WIPO . |
| 96/00597 | 1/1996 | WIPO . |

*Primary Examiner*—Beverly M. Flanagan
*Attorney, Agent, or Firm*—Frishauf, Holtz, Goodman, Langer & Chick, P.C.

[57] ABSTRACT

A system for evulsing subcutaneous tissue including an endoscope adapted to be inserted into subcutaneous tissue through a skin cut portion to observe tissue to be evulsed and existing under the skin, a dissecting unit adapted to be inserted into the subcutaneous tissue through the skin cut portion so as to dissect the tissue, to be evulsed, from surrounding tissue in order to form a cavity along the tissue to be evulsed and below the skin, a cavity maintaining unit adapted to be inserted from the skin cut portion into the cavity formed by the dissecting unit and to be retained in the cavity in order to maintain, around the tissue to be evulsed, a treatment space which permits the endoscope to be inserted and removed and which enables treatment of the tissue to be evulsed, and at least one treatment tool adapted to be inserted into the treatment space maintained by the cavity maintaining unit in order to perform, in the treatment space, treatment required to evulse the tissue to be evulsed.

20 Claims, 64 Drawing Sheets

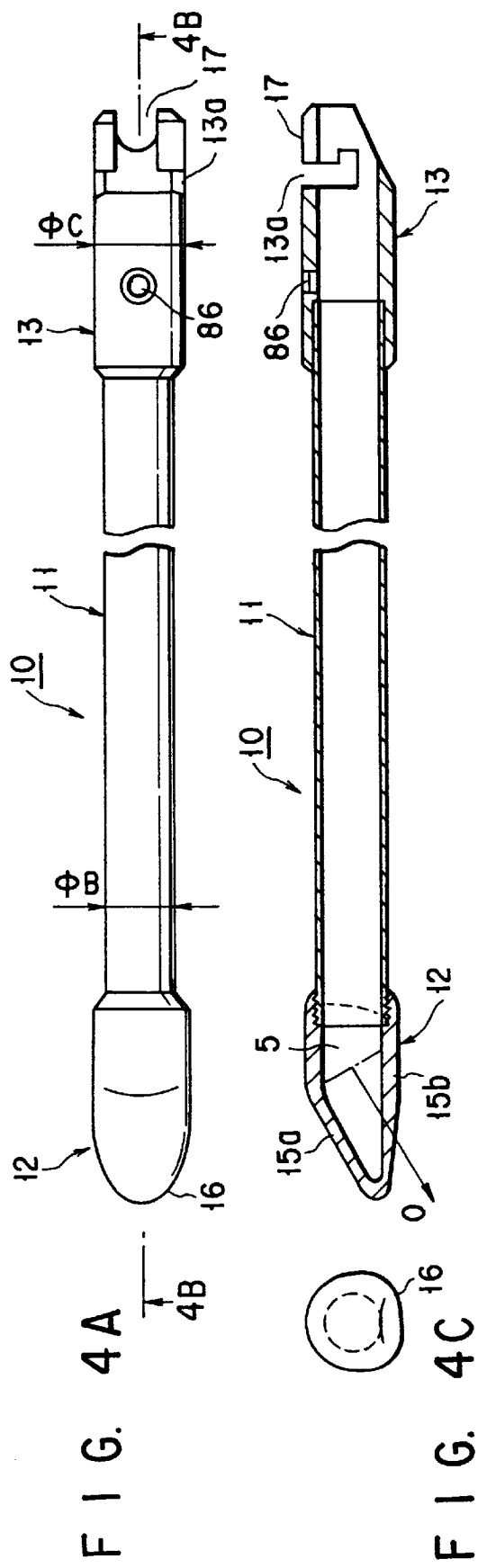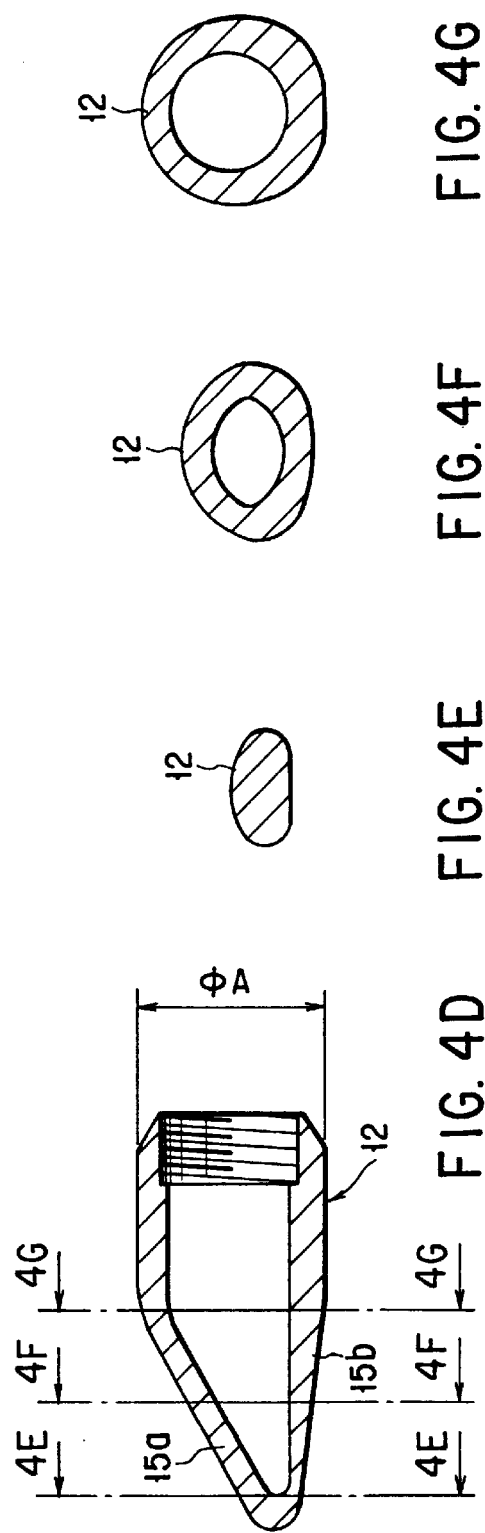

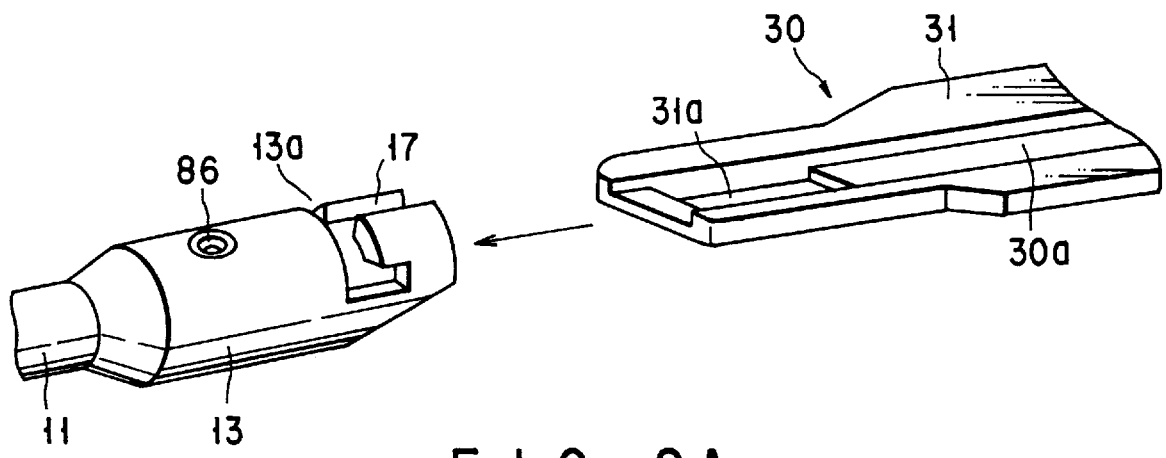
F I G. 8A
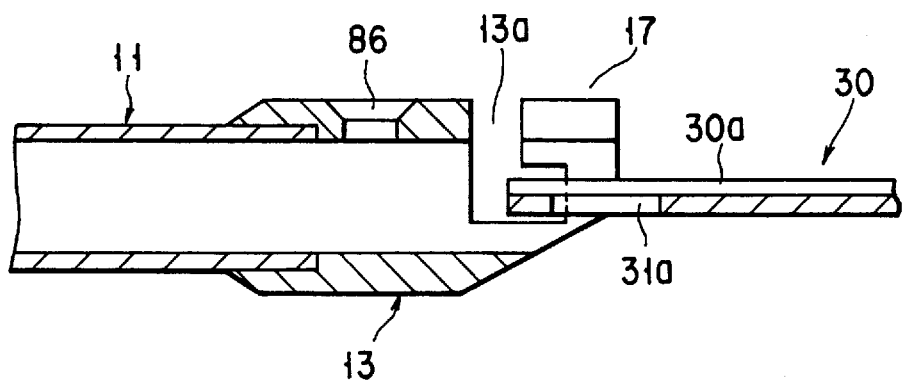
F I G. 8B
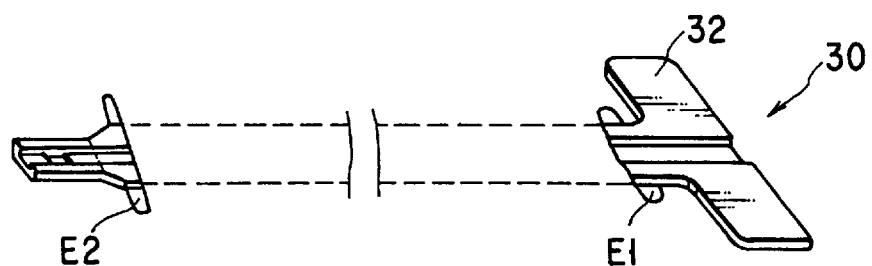
F I G. 9

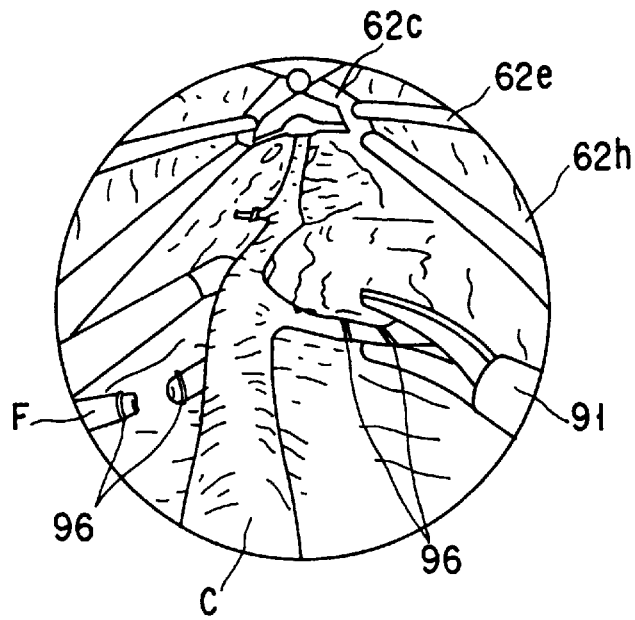
F I G. 18
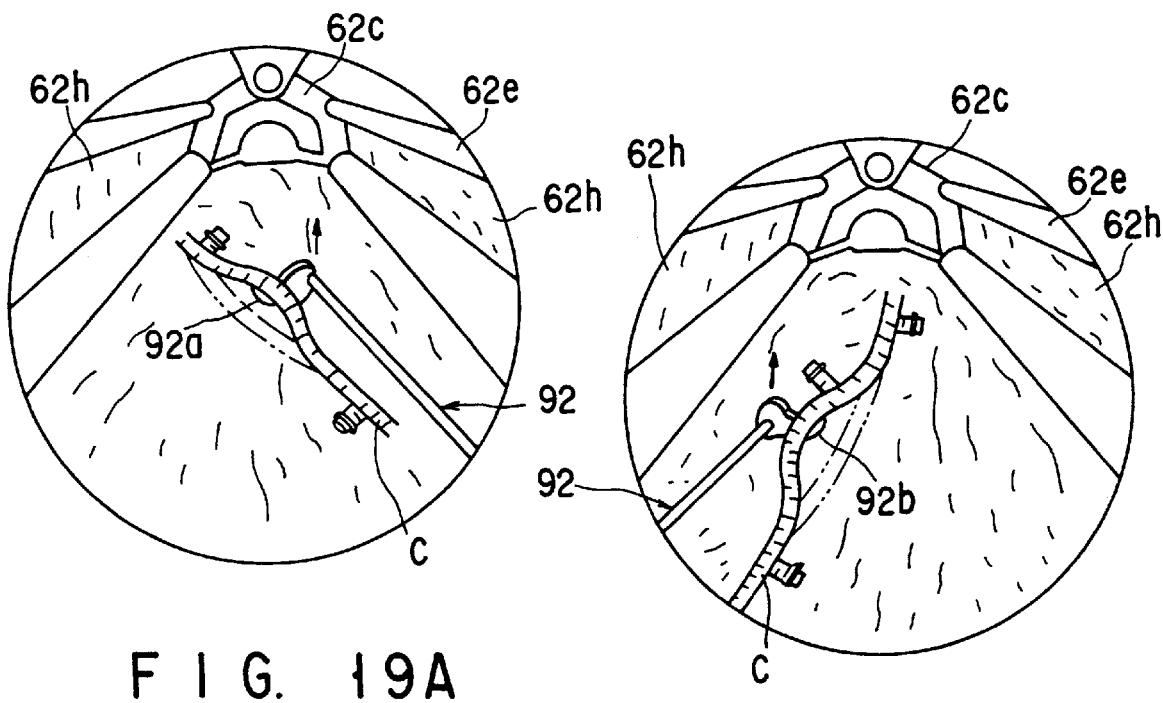
F I G. 19A
F I G. 19B

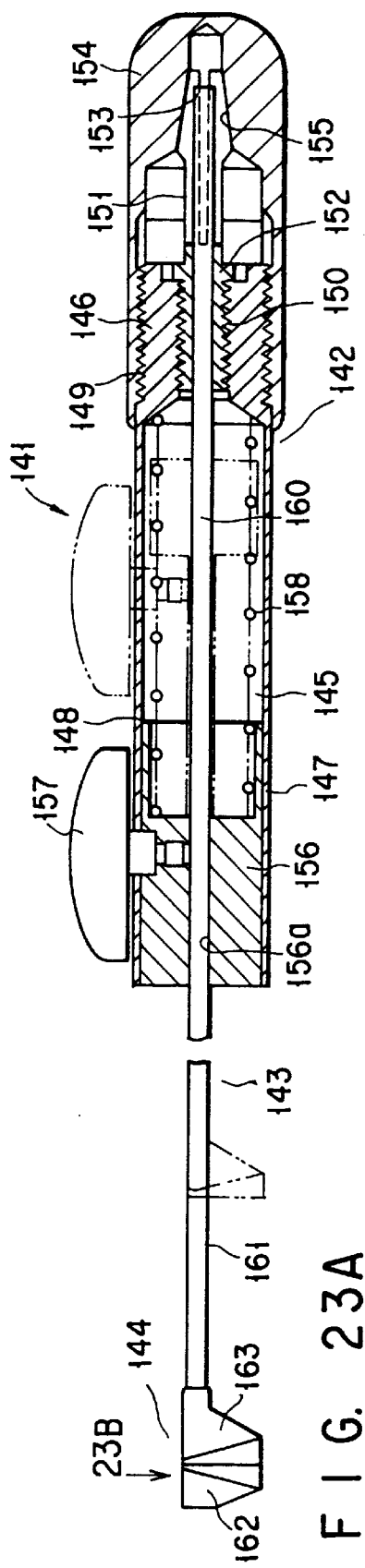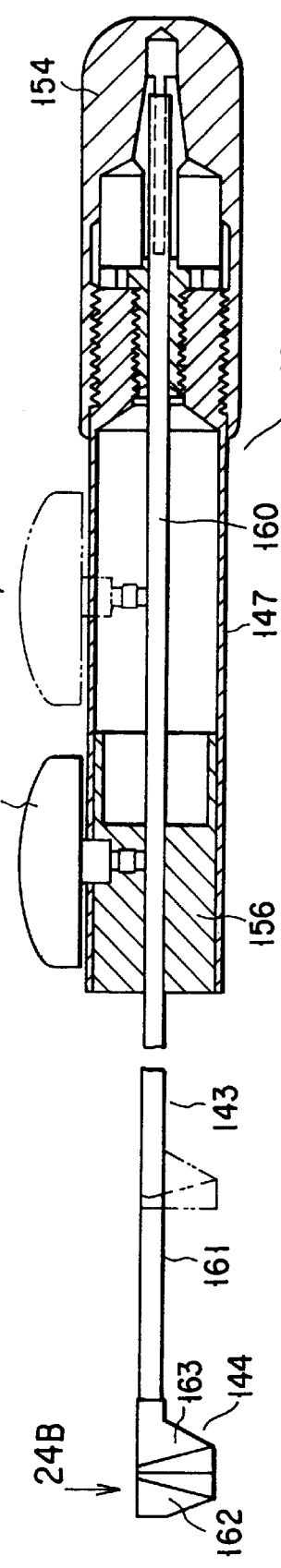

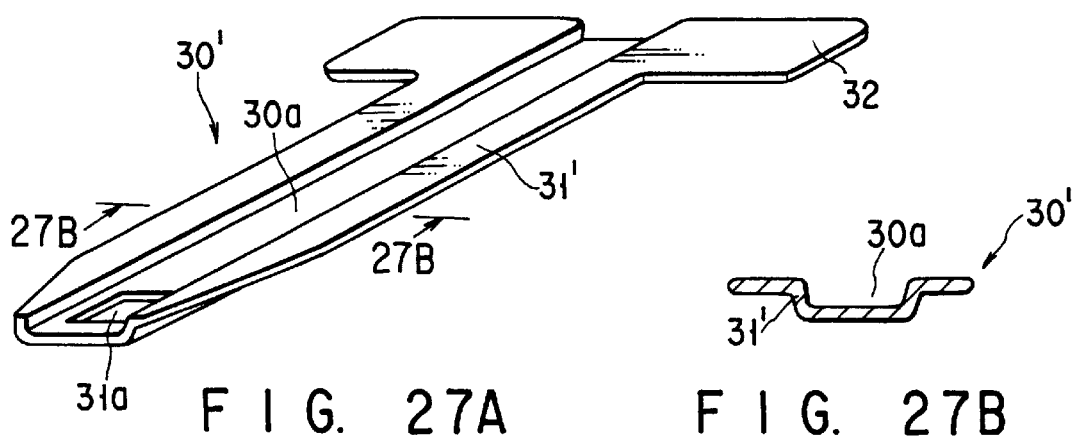
FIG. 27A    FIG. 27B
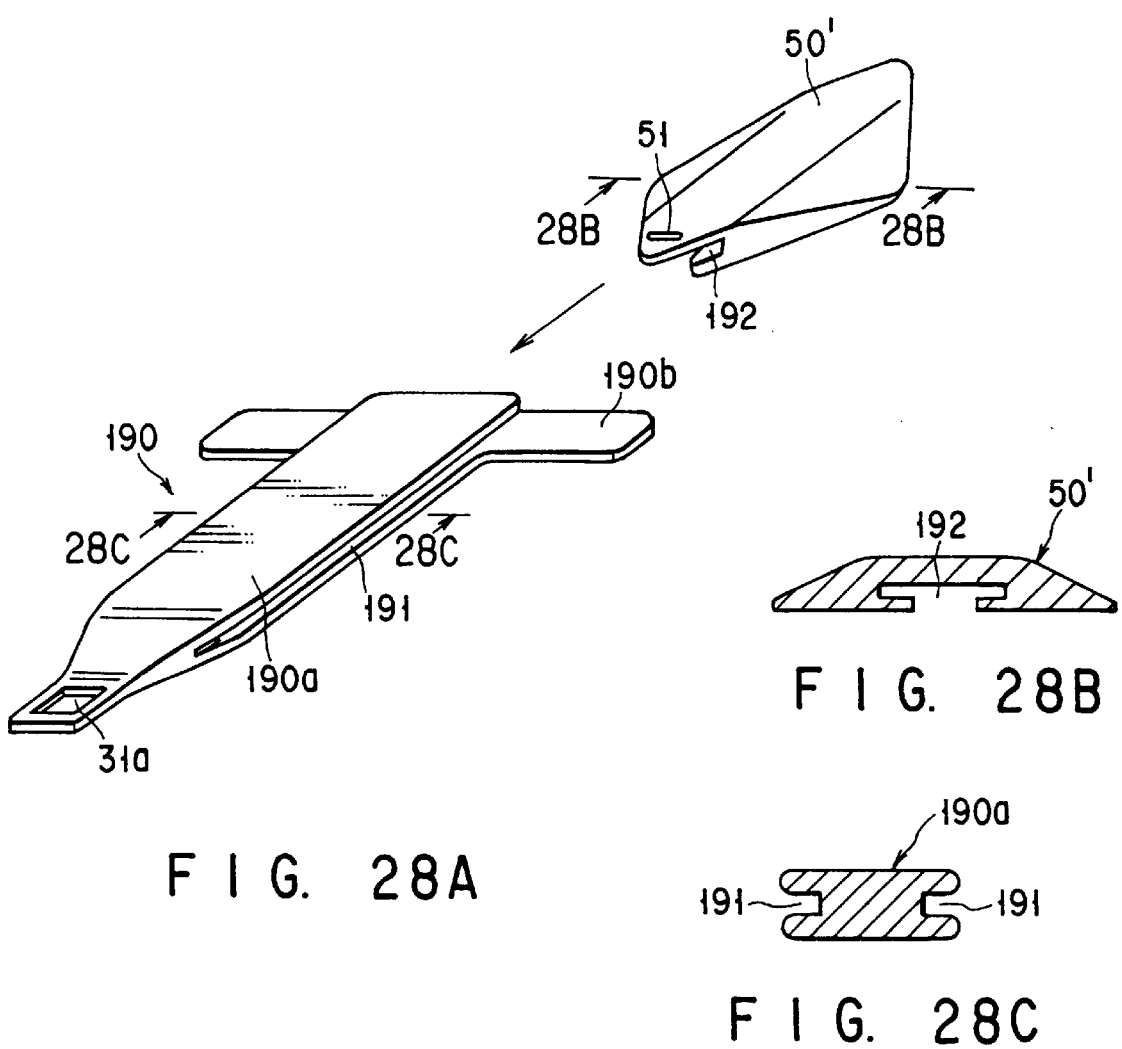
FIG. 28A
FIG. 28B
FIG. 28C

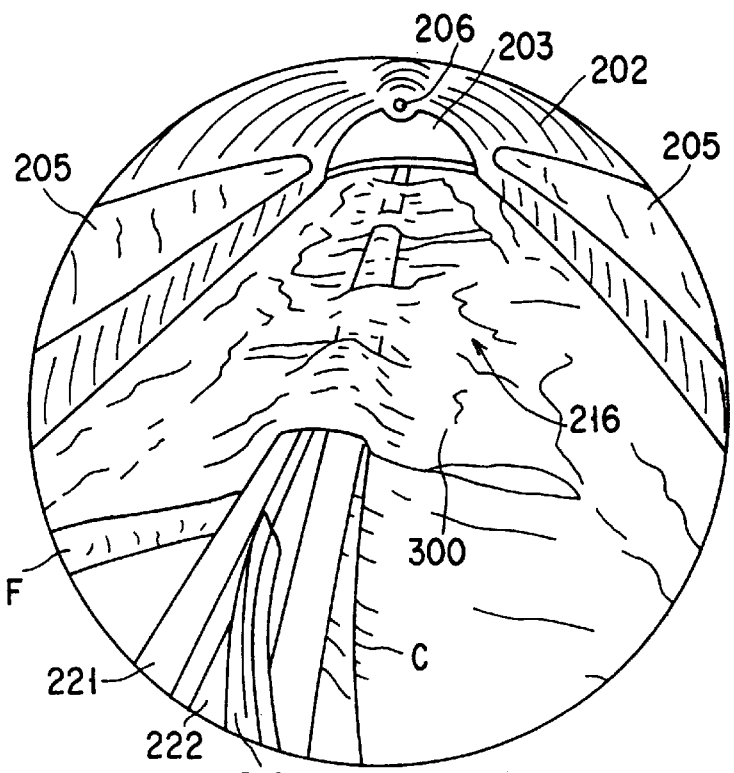
F I G. 34
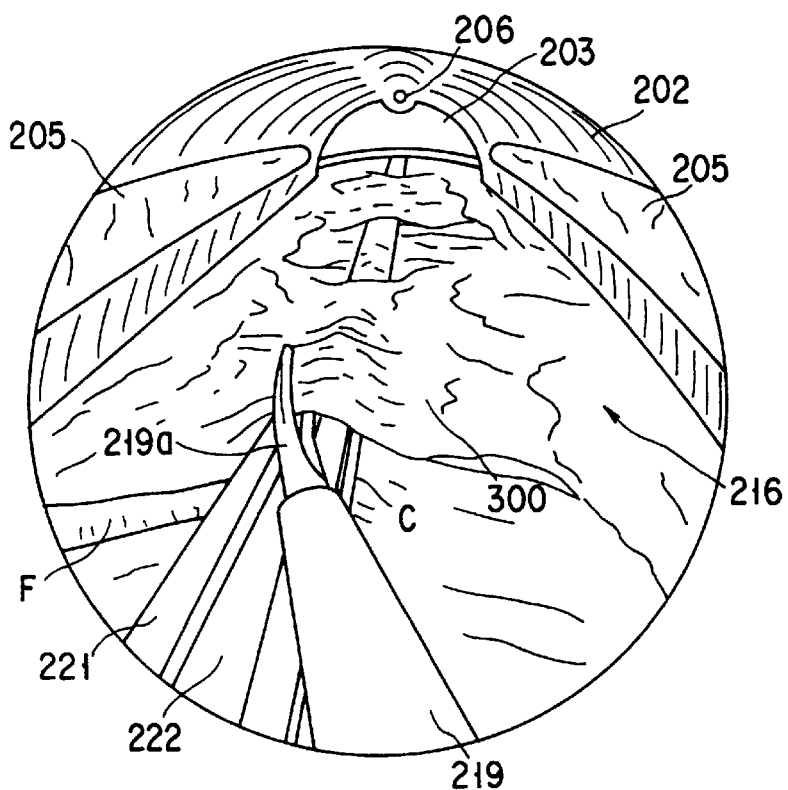
F I G. 35

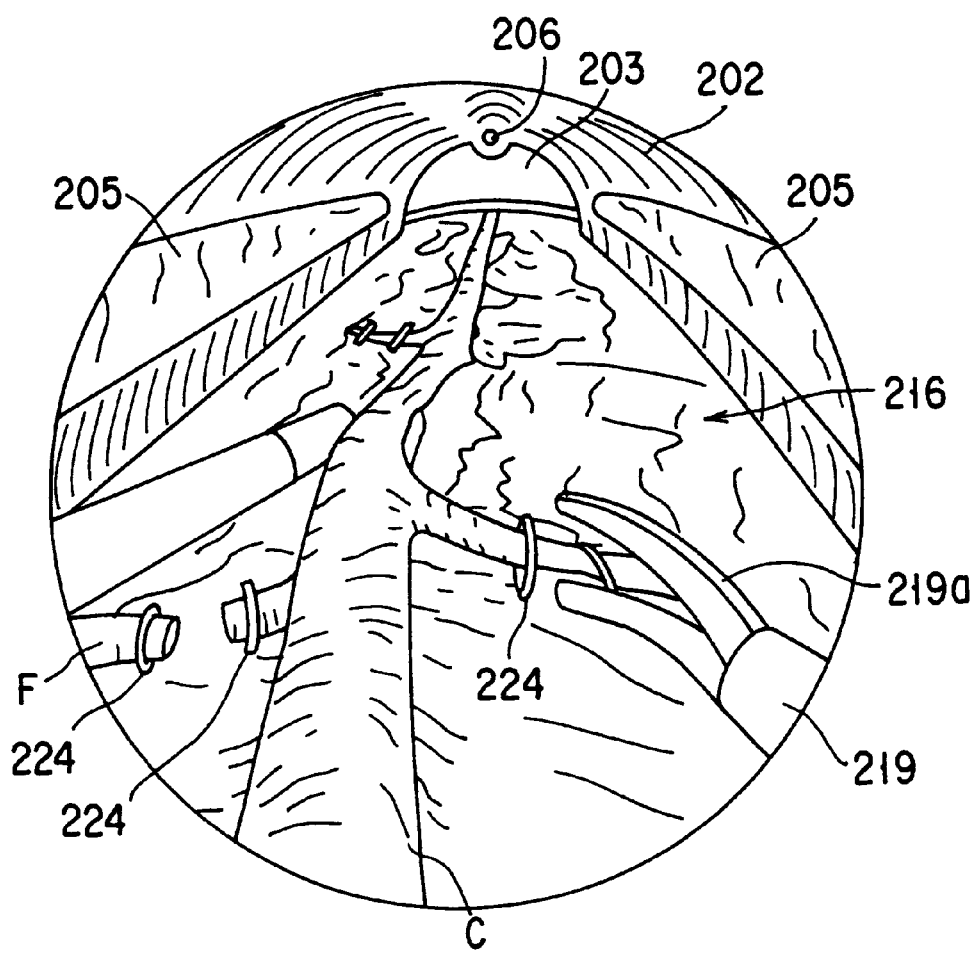
F I G. 38
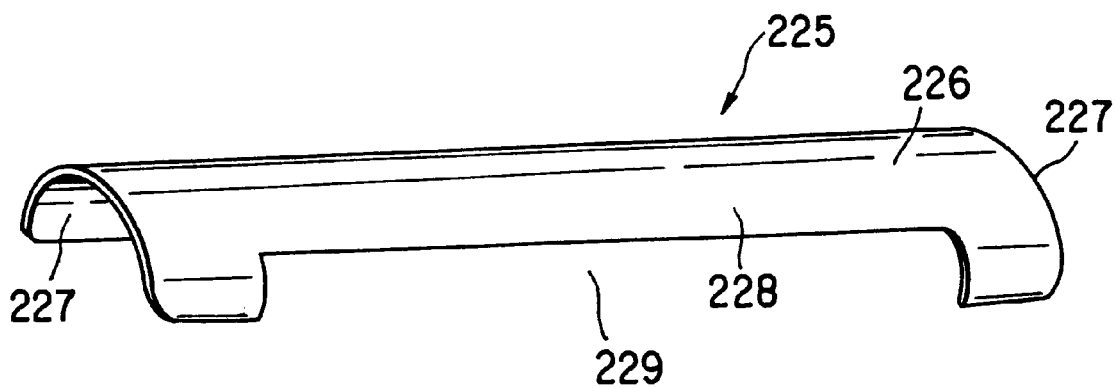
F I G. 39

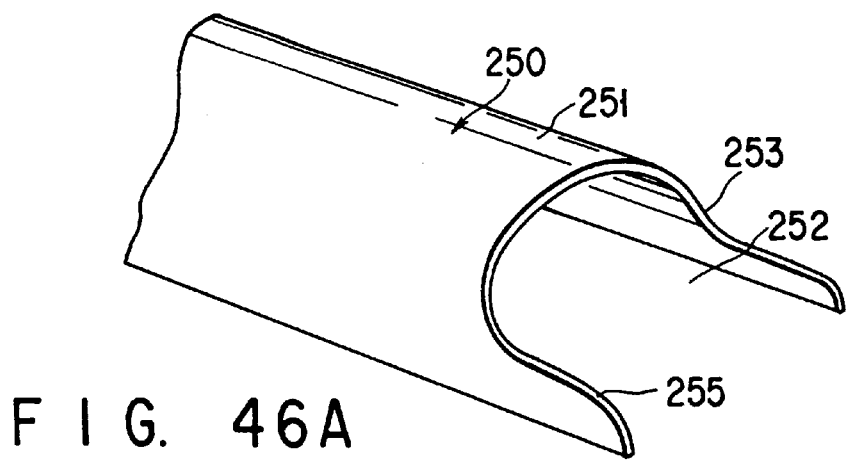
F I G. 46A
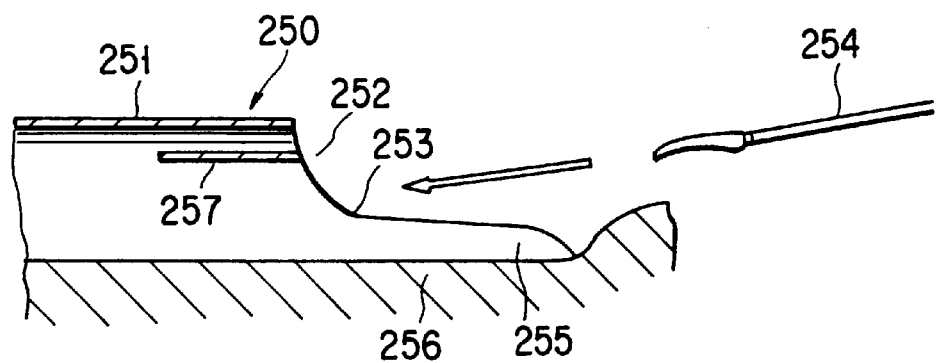
F I G. 46B
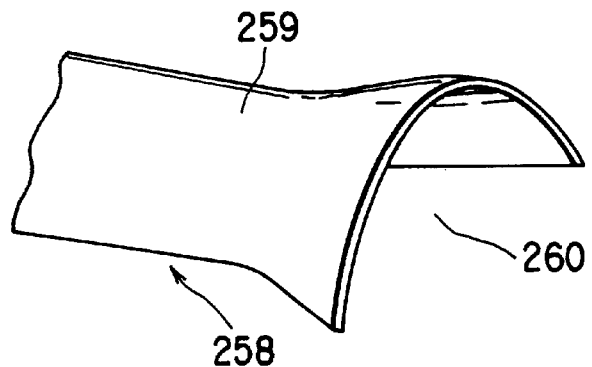
F I G. 47

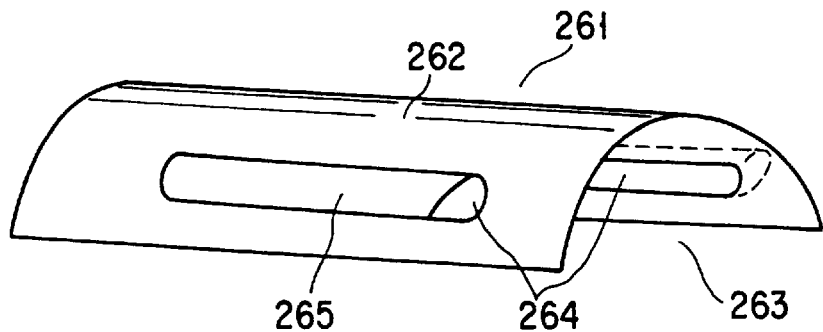
F I G. 48A
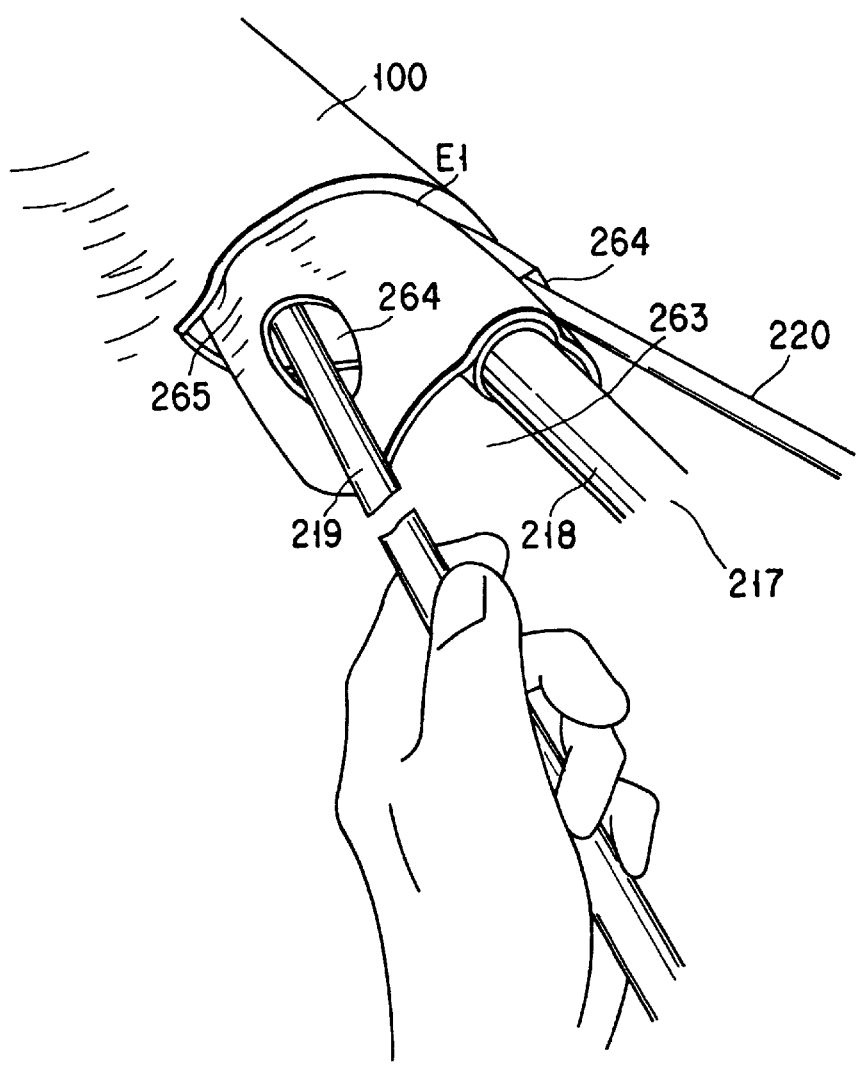
F I G. 48B

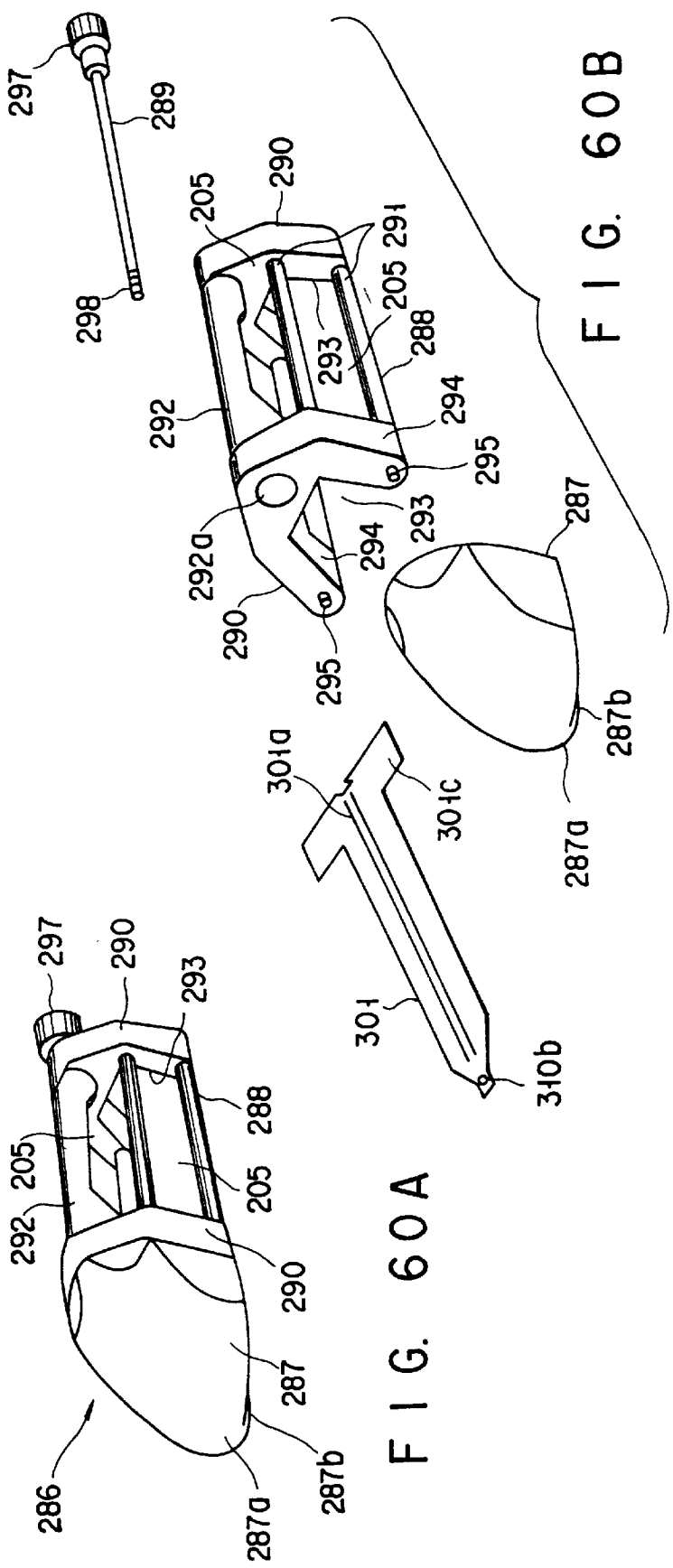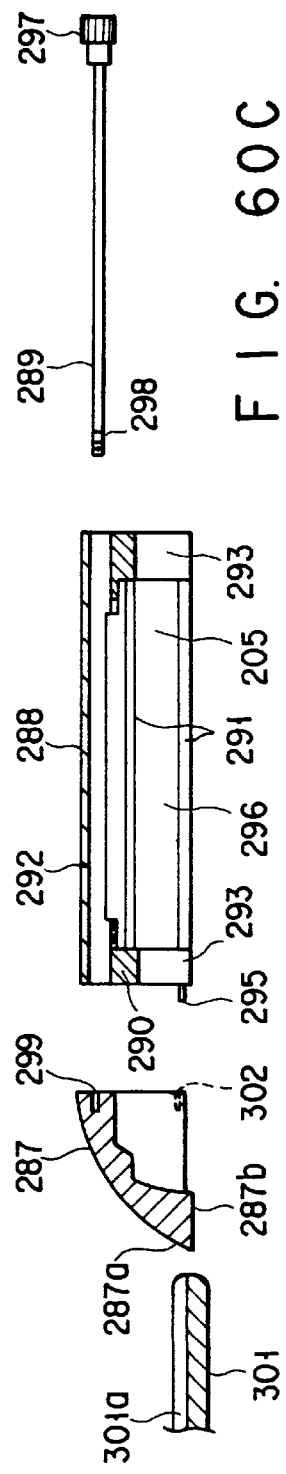

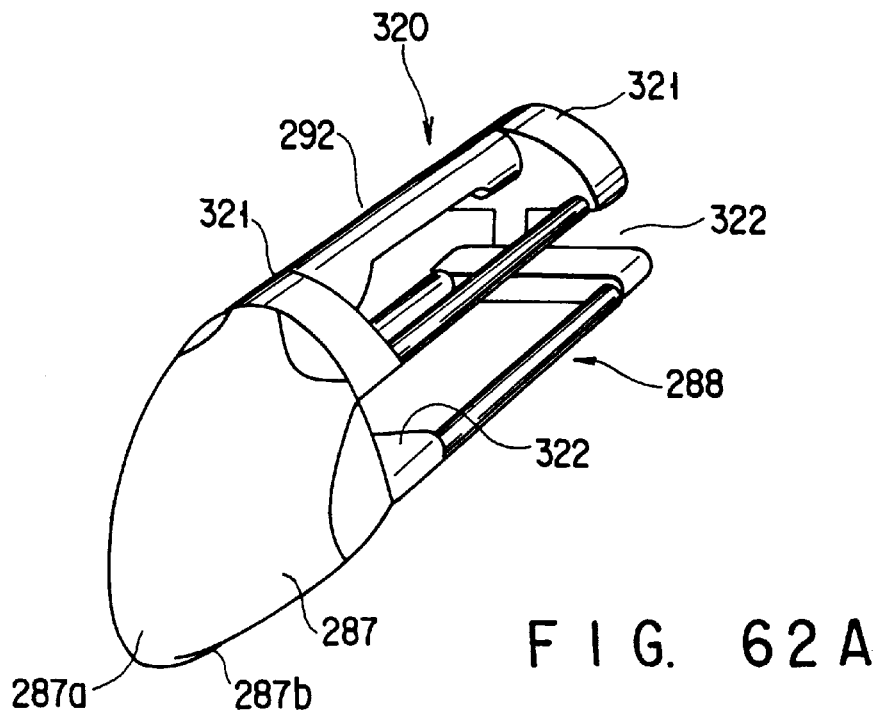
F I G. 62A
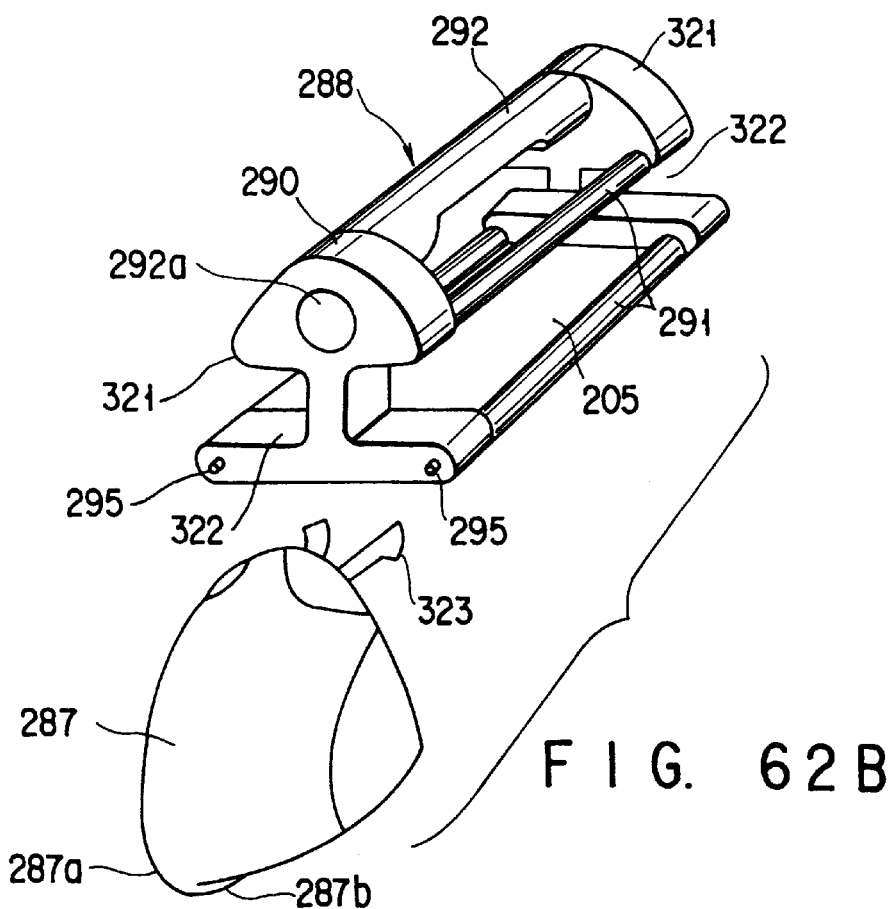
F I G. 62B

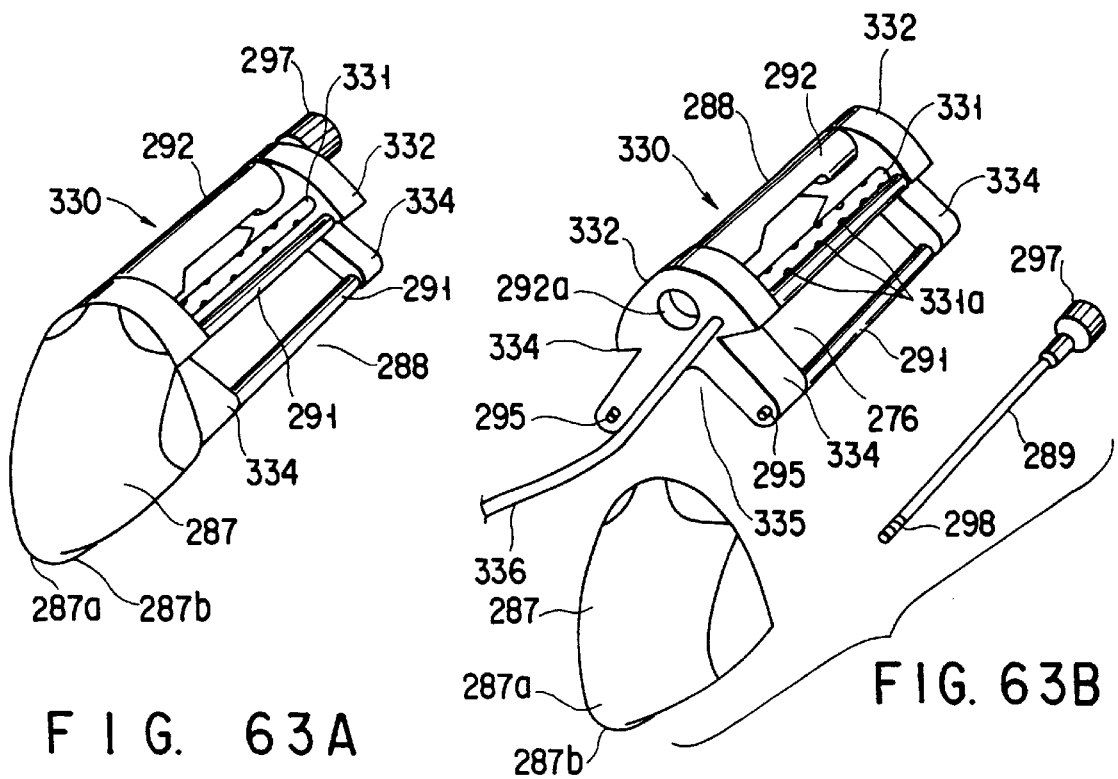
FIG. 63A
FIG. 63B
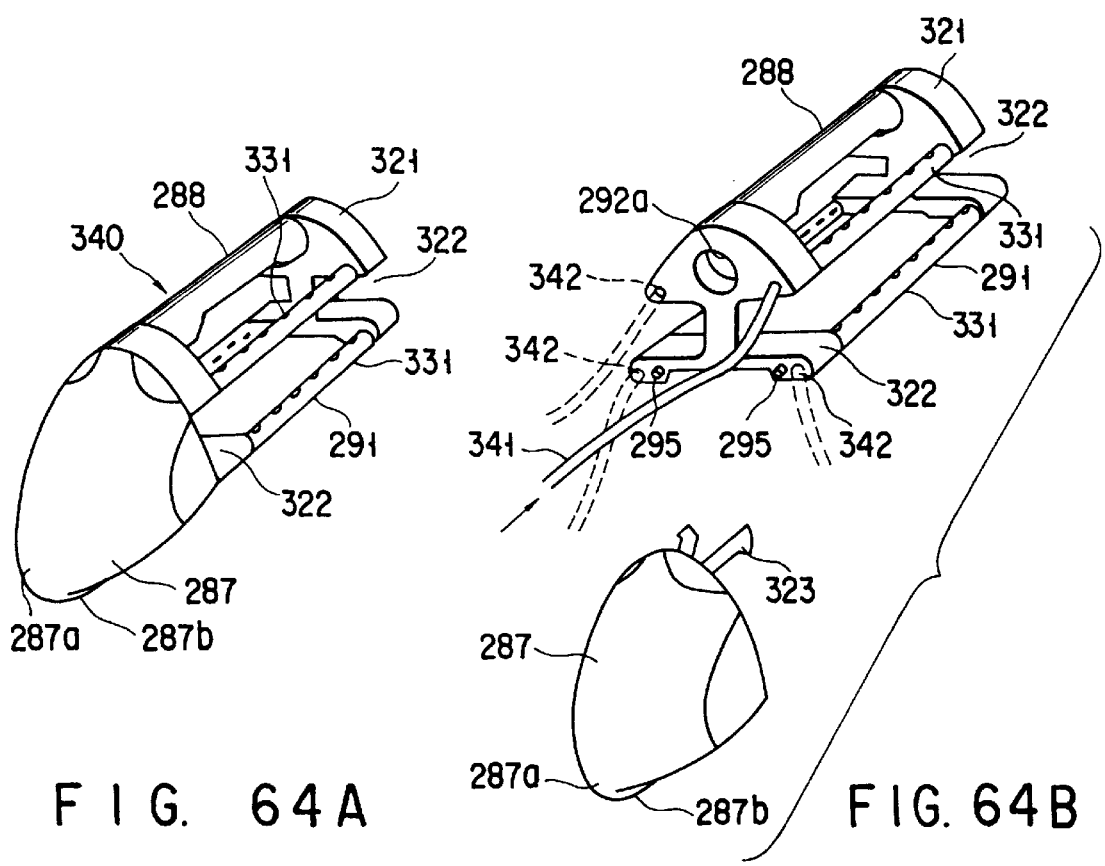
FIG. 64A
FIG. 64B

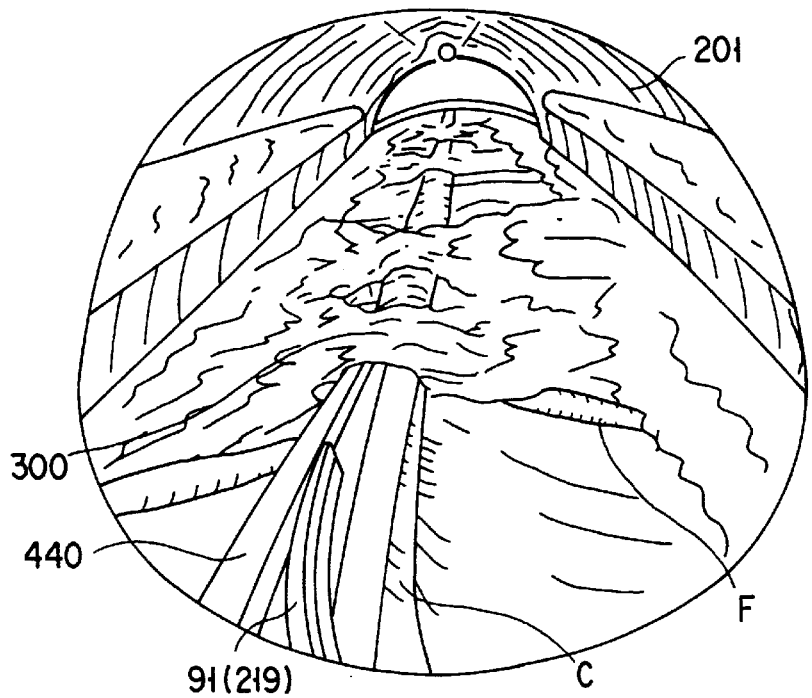
F I G. 67A
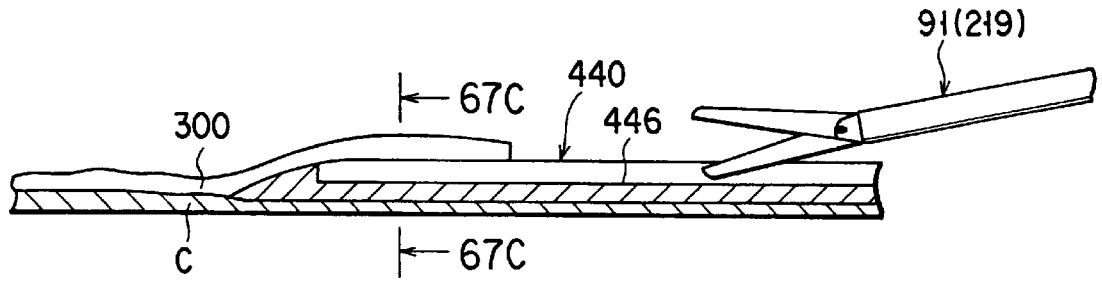
F I G. 67B
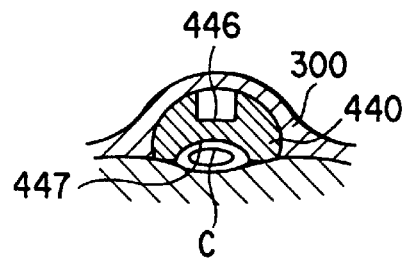
F I G. 67C

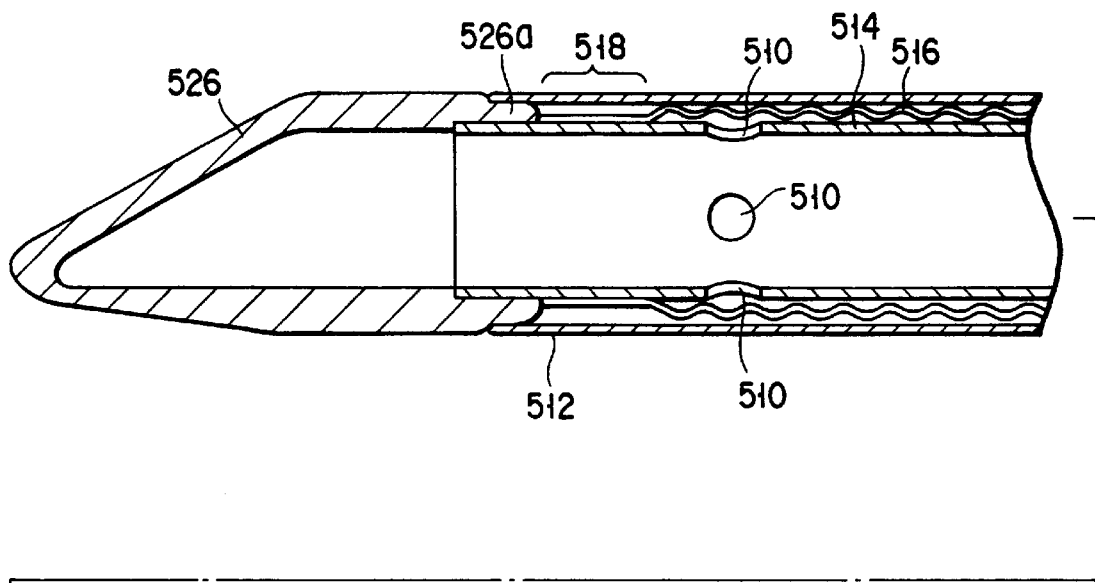
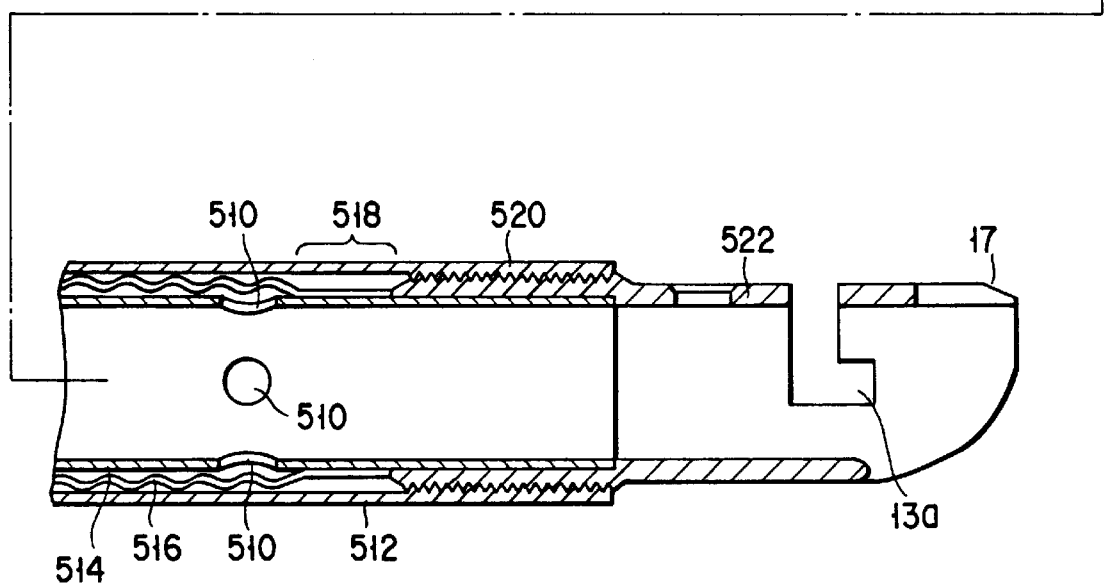
FIG. 73

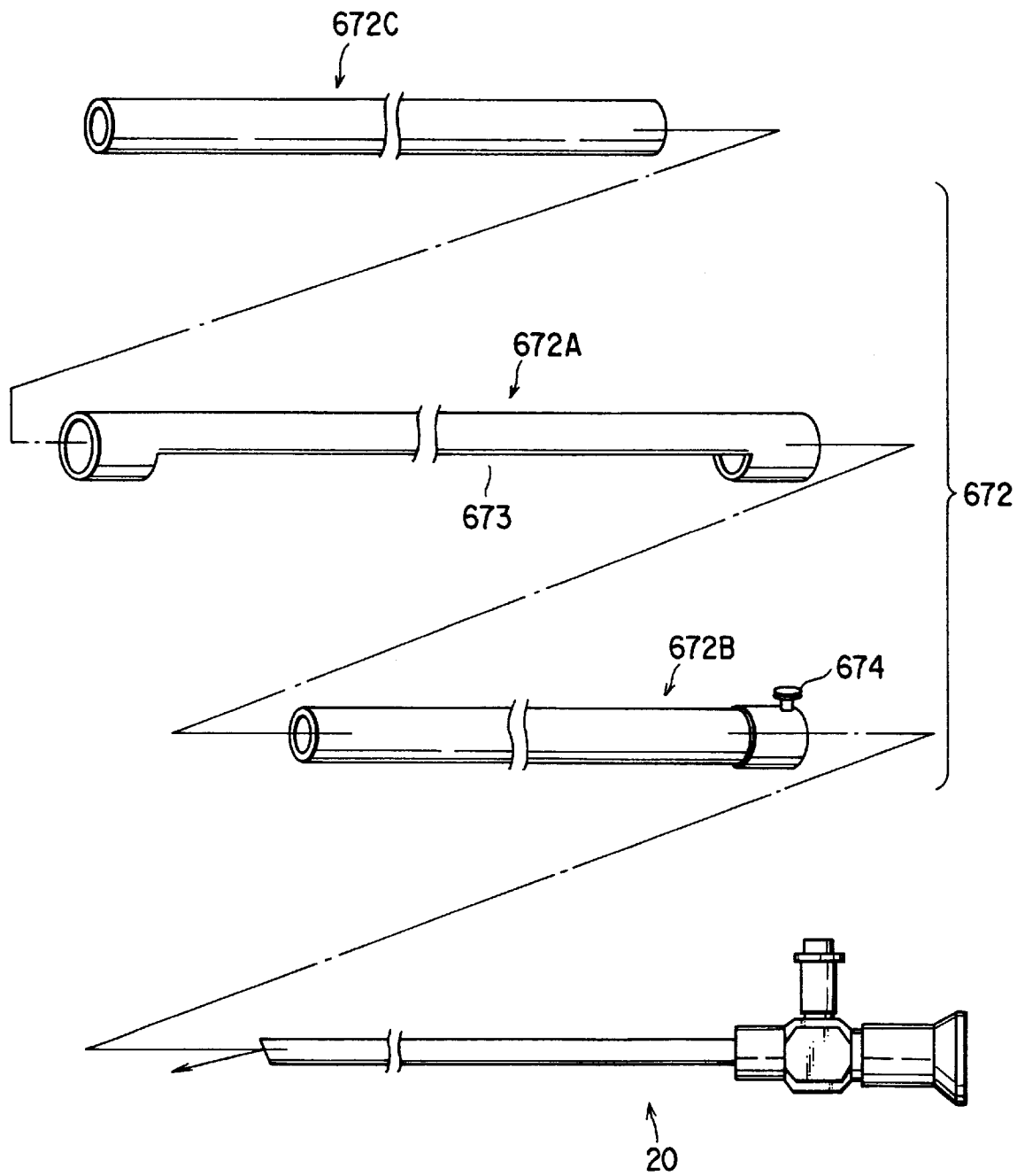
F I G. 79

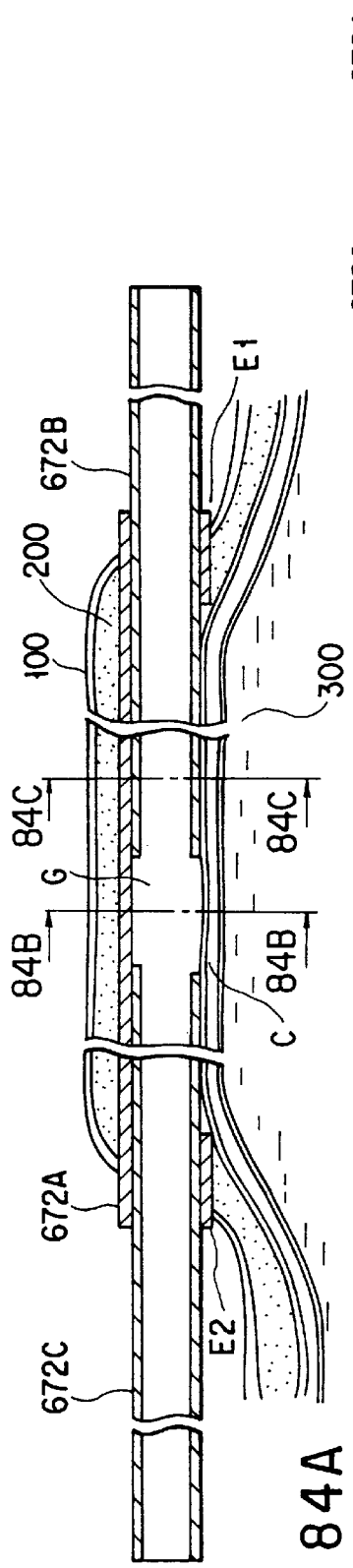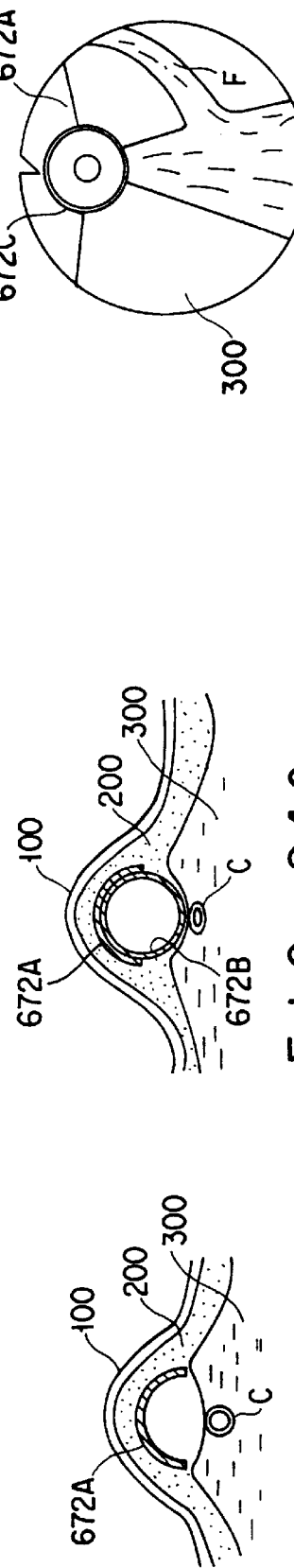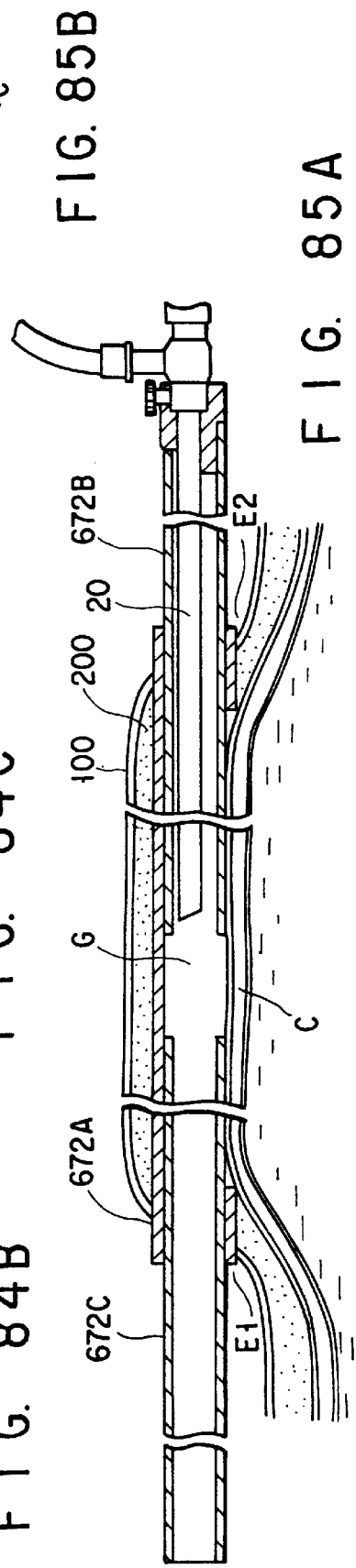

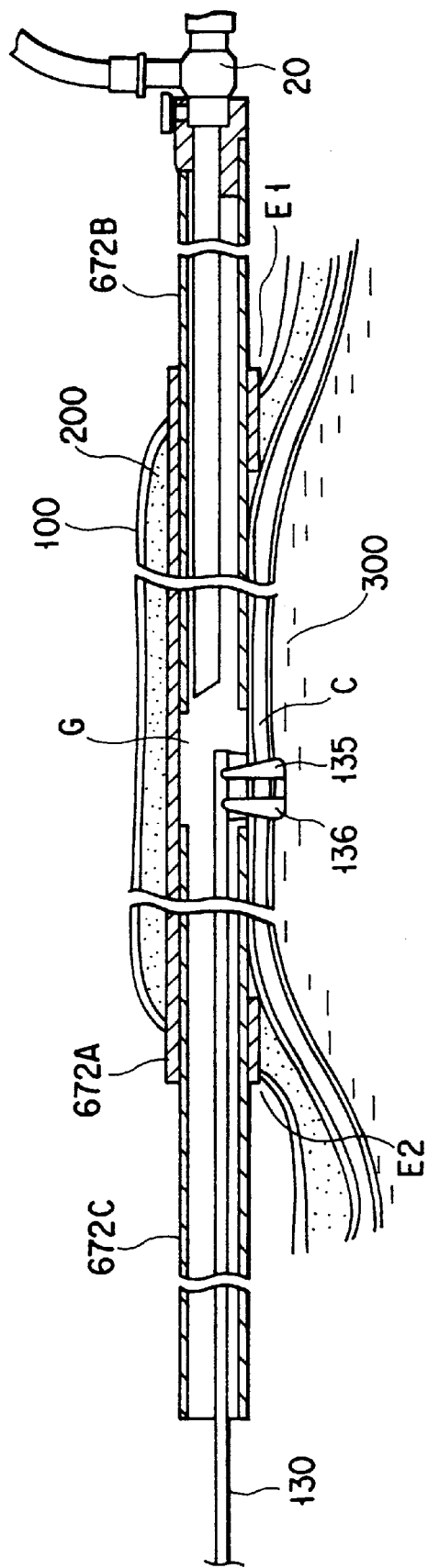
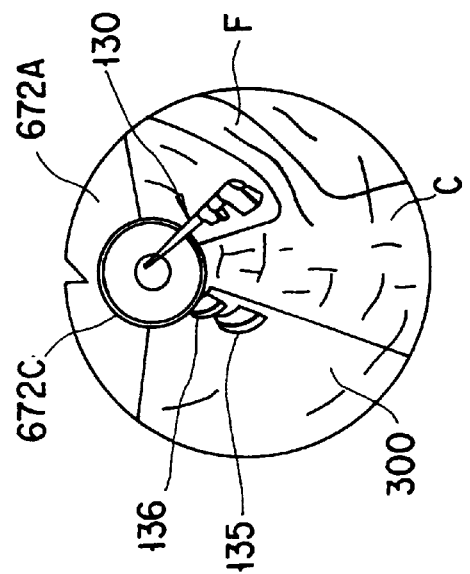
FIG. 86A
FIG. 86B

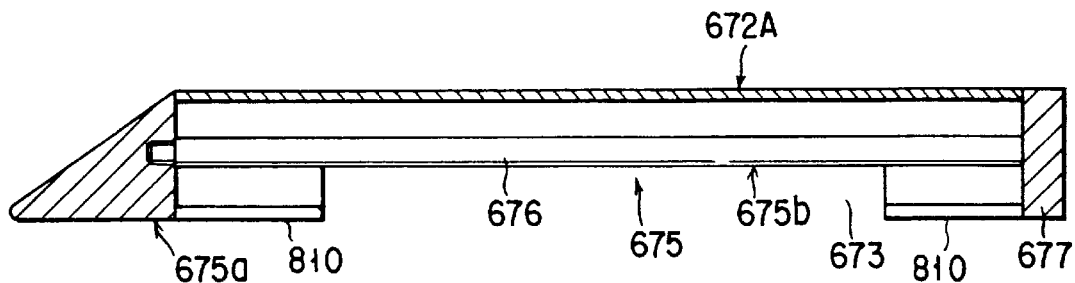
F I G. 94
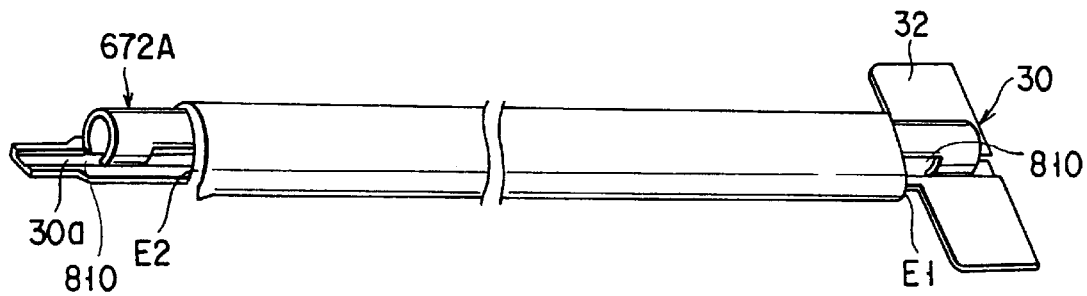
F I G. 95
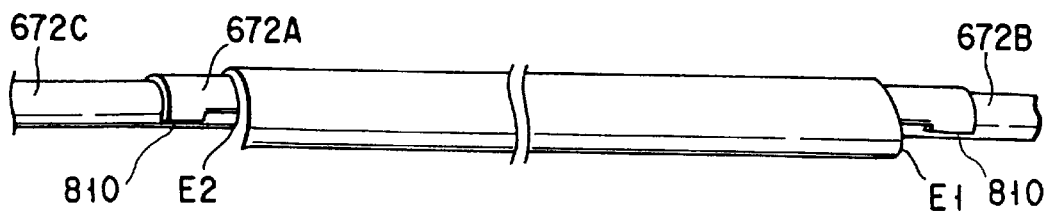
F I G. 96

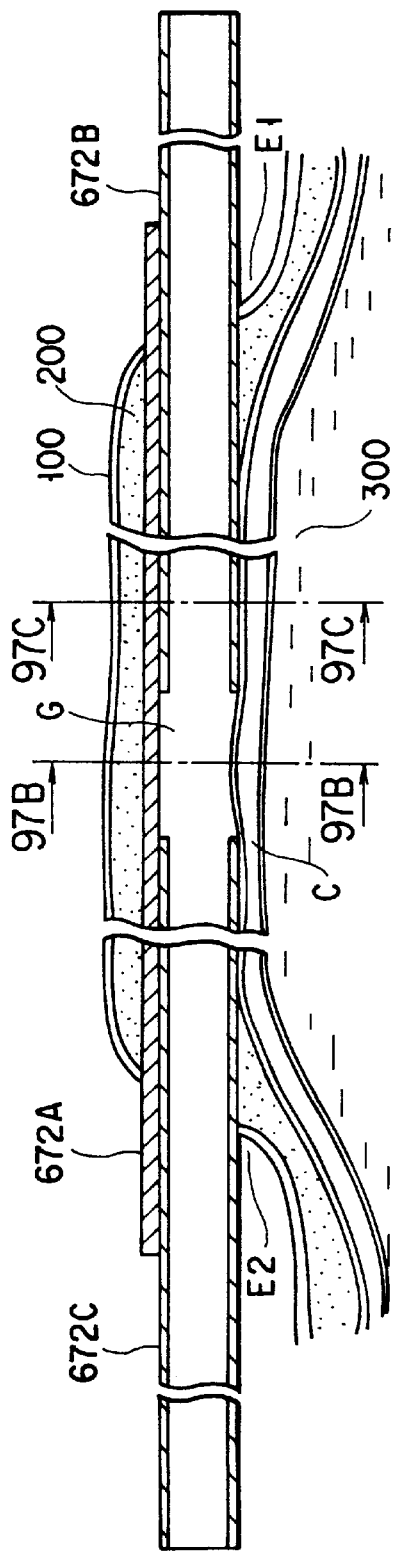
FIG. 97A
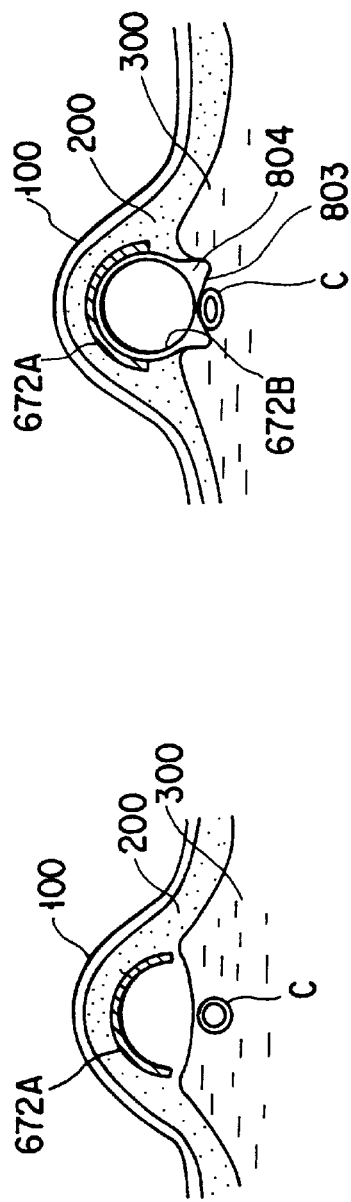
FIG. 97C
FIG. 97B

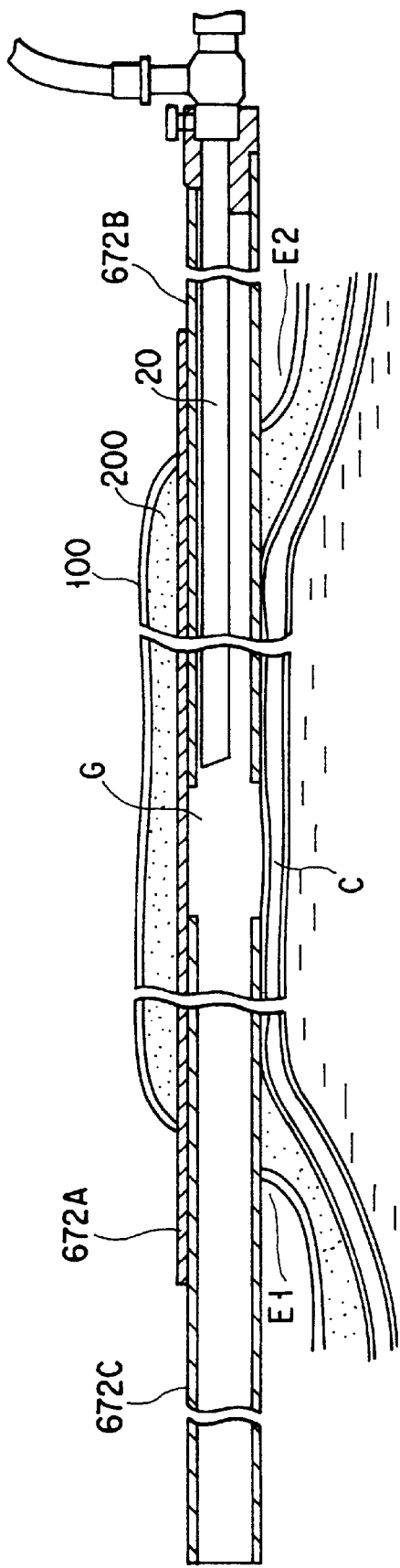
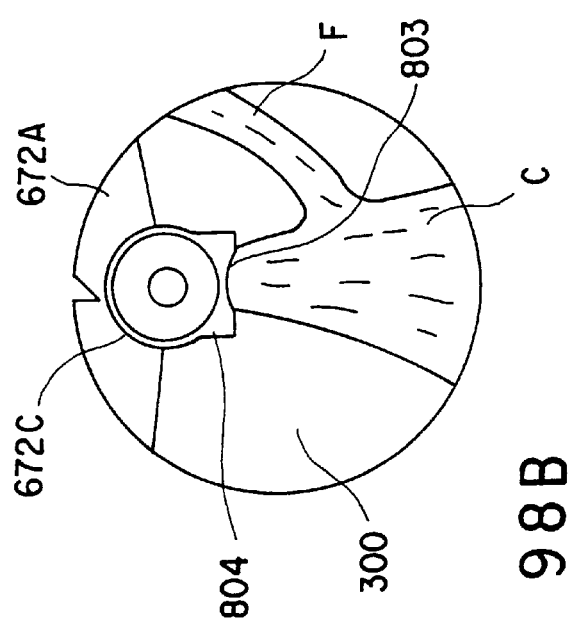
FIG. 98A
FIG. 98B

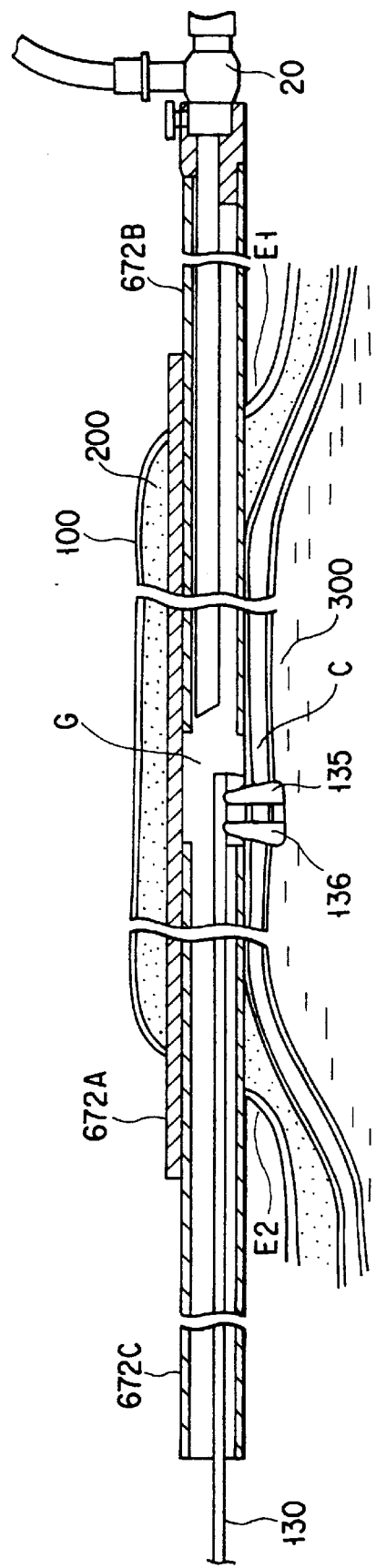
F I G. 99A
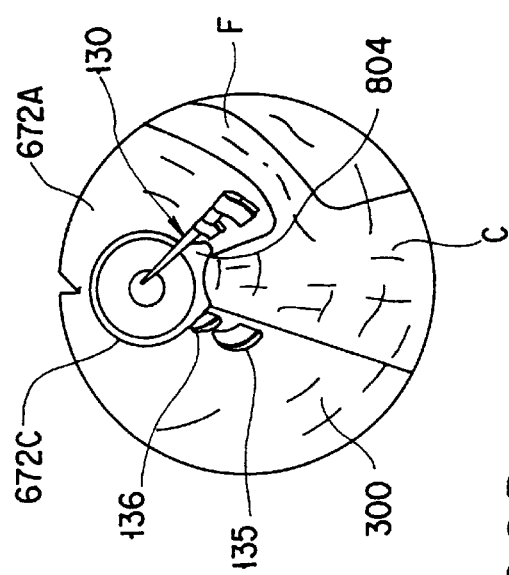
F I G. 99B

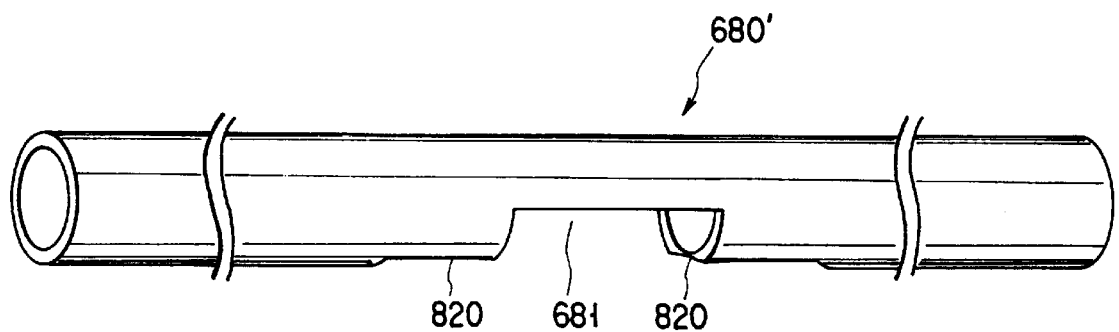
F I G. 100
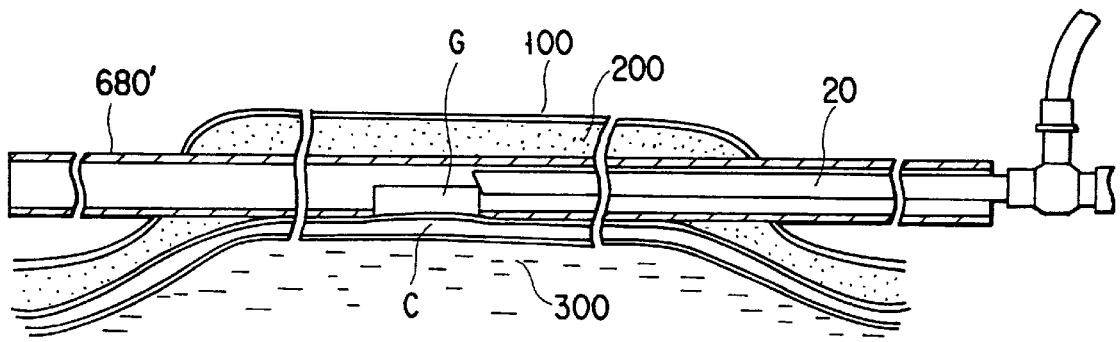
F I G. 101A
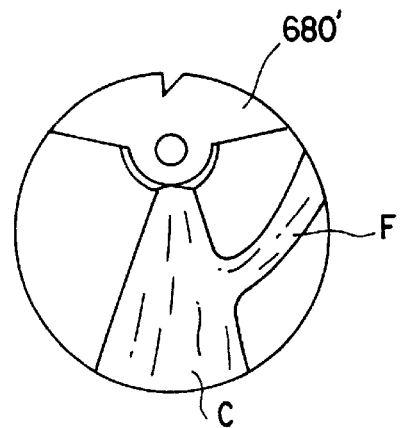
F I G. 101B

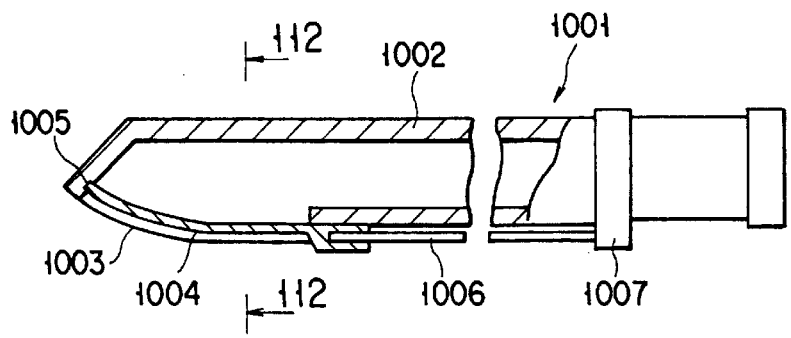
F I G. 111A
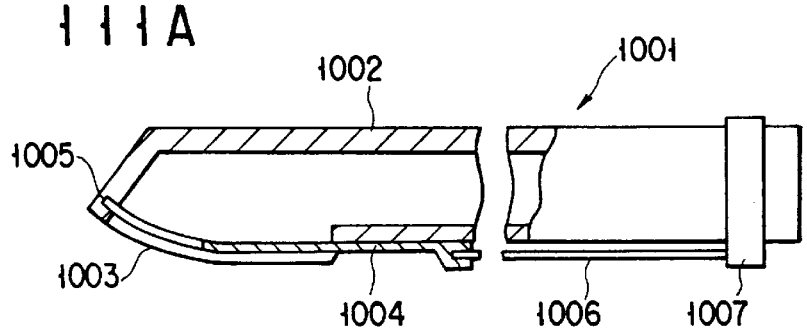
F I G. 111B
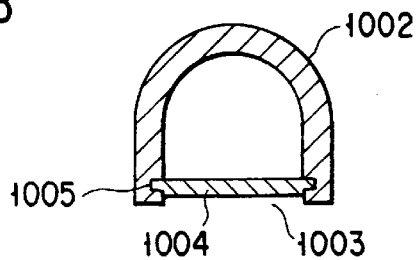
F I G. 112
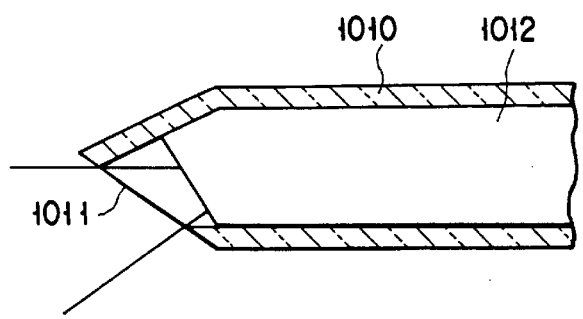
F I G. 113A
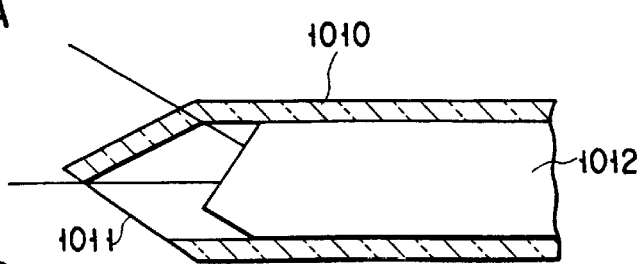
F I G. 113B

SYSTEM FOR EVULSING SUBCUTANEOUS TISSUE

This is a divisional application of application Ser. No. 08/676,856, filed Jul. 3, 1996, now U.S. Pat. No. 5,759,150.

BACKGROUND OF THE INVENTION

1. Field of the Invention

The present invention relates to a system for evulsing subcutaneous tissue represented by a subcutaneous blood vessel, such as a saphenous vein, by using an endoscope.

2. Description of the Related Art

When, for example, an operation for bypassing a blood vessel in the heart is performed, a saphenous vein existing in the leg of the body is extracted in order to use the saphenous vein as a bypass blood vessel. When the saphenous vein is extracted, an operation for separating the saphenous vein from other textures is initially required. The upper texture of the saphenous vein has a structure formed by sequentially stacking the connective tissue covering the saphenous vein, and fat and the skin formed on the connective tissue.

When an operation for extracting the subcutaneous blood vessel, such as the saphenous vein in the lower extremity, is performed, the skin is incised along the blood vessel below the skin with, for example, a knife. Then, the subcutaneous tissue, such as the panniculus adiposis, in the lower layer of the skin and the connective tissue on the blood vessel are incised so that the blood vessel having a length intended to be extracted is exposed. The two ends of the exposed blood vessel are is cut and taken out to the outside of the body. However, the extracting operation results in the skin being considerably incised, and an excessively long time is required for the patient to be cured. What is worse, the incised portion is scarred and hardened, thus causing a problem in that the patient has a cramp in the leg when he moves the leg and thus the patient feels a pain.

Accordingly, it might be considered feasible to extract the subcutaneous blood vessel, such as the saphenous vein, through a small cut portion on the skin in the lower extremity. The other methods for extracting the subcutaneous blood vessel, such as the saphenous vein, through a small cut portion of the skin have been disclosed in, for example, U.S. Pat. No. 4,793,346 and U.S. Pat. No. 5,373,840. Especially, the method disclosed in U.S. Pat. No. 5,373,840 is concerned with extracting the subcutaneous blood vessel by using an endoscope.

The method disclosed in U.S. Pat. No. 4,793,346 has the steps of incising the skin of the lower extremity; inserting, through the incised portion, a tube having an inner diameter somewhat larger than the outer diameter of the vein; and allowing an electric current to flow through a knife disposed at the leading end of the tube, so that the tube is moved forwards while being rotated. As a result, the side branches of the vein are cauterized and cut by the knife so that the vein is extracted.

The method disclosed in U.S. Pat. No. 5,373,840 is arranged to use an endoscope having a channel extending longitudinally to take out an end of the blood vessel, to be extracted, through a cut portion of the body of a patient. Thus, the blood vessel is held by a grip means through the channel of the endoscope and the blood vessel is removed by cutting.

However, the method disclosed in U.S. Pat. No. 4,793,346 is a method of blindly moving forwards the tube having the knife. Therefore, the foregoing method has a risk of the saphenous vein, intended to be extracted, being undesirably cut in addition to the fact that the saphenous vein is not straight in general. Moreover, the method has a risk of the saphenous vein being burnt thermally due to the electric current allowed to flow from the knife.

With the method disclosed in U.S. Pat. No. 5,373,840, the endoscope is moved forward along the blood vessel and any one of a variety of treatment tools is inserted into the body through the channel of the endoscope. Then, the tissue is ablated by the treatment tool while being observed through the endoscope so that the blood vessel is treated. Therefore, a too complicated operation is required and a long time is required to complete the operation. What is worse, if the objective lens of the endoscope is contaminated with blood or the like, a complicated operation is required in which all of the devices are removed to the outside of the body.

In a case where the skin is cut to permit the endoscope and the treatment tool to be inserted into the lower extremity through the cut portion so as to extract the subcutaneous blood vessel, a cavity is required around the subcutaneous blood vessel because the blood vessel exists under the skin in which no cavity exists. That is, the blood vessel and the other portions including the connective tissue are required to be considerably apart from each other so as to form a working space between the blood vessel and the connective tissue to extract the blood vessel. However, a cavity cannot easily be formed around the subcutaneous blood vessel because the subcutaneous tissue, such as the panniculus adiposis, and the connective tissue on the blood vessel exist around the subcutaneous blood vessel.

A cannula for forming a cavity, into which the endoscope and the treatment tool can be inserted, in the body and which permits treatment and observation of a diseased part to be performed in the cavity with the endoscope has been disclosed in, for example, WO93/10704. The cannula has a body formed into a cylindrical shape having two opened ends. Moreover, a slit is formed along the axis of the cylindrical body of the cannula. The cannula is used such that the leading end of the body of the cannula is introduced into the body through an incised portion of the skin, and then its leading end is discharged to the outside of the body through another incised portion so that the two end openings are exposed and thus a cavity is formed in the body cavity. After the cavity has been formed in the body cavity by the cannula, the endoscope is introduced into the cannula through one of the openings of the body of the cannula, that is, into the cavity formed by the cannula. Moreover, a treatment tool is, through another opening or the slit of the body of the cannula, introduced into the cavity formed by the cannula. Thus, while observing the diseased part through the endoscope, the diseased part can be treated by the treatment tool.

Although the cannula is suitable to be in an operation for ablating a diseased part in the fibrous tissue as is performed in surgical treatment of a carpal tunnel syndrome, the cannula is unsuitable to be in an operation for extracting the subcutaneous blood vessel, such as the saphenous vein in the lower extremity, because a satisfactorily large cavity cannot be formed. If a satisfactorily large cavity cannot be formed, the endoscope and the treatment tool inserted into the cavity cannot easily be manipulated. Thus, the subject tissue and the surrounding tissues can easily be damaged.

As described above, the operator must pay great attention to protect the subcutaneous tissue from being damaged when the operator treats a portion in the vicinity of the subcutaneous tissue, such as the blood vessel and the nerve. However, the ablating operation and the incising operation, to be performed just above the saphenous vein intended to be extracted, have a risk of the saphenous vein being damaged by the treatment tool or the like during the operation. The operation for forming a cavity under the skin has a similar risk. The saphenous vein for use as a bypass blood vessel in the heart is required to be extracted while being protected from any damage. The foregoing requirement is not limited to the extraction of the saphenous vein. Also the same requirement arises in any case where the tissues, which must be protected, exist near the portion in which a treatment operation is performed.

On the other hand, a technique has been developed which has an arrangement such that a hood is attached to the insertion portion of the endoscope to protect an observation window of the endoscope from being contaminated due to adhesion of the tissue of the organism to the observation window and to form a space which permits an observation to be performed with the endoscope when the tissue of the organism, such as the subcutaneous tissue, having no cavity therein is observed and treated by using the endoscope. The foregoing objects are important facts when the subcutaneous tissue is evulsed.

The applicant of the present invention has applied a sheath which serves as the hood to be attached to the insertion portion of the endoscope and which has a cylindrical shape having an opened leading end (refer to Japanese Patent Application No. 7-172466 published as Japanese Patent Laid-Open No. 8-117181) and a hood having a shape capable of completely covering the endoscope and suitable to excise the tissue (refer to Japanese Patent Application No. 7-172139). Moreover, a hood has been disclosed in Japanese Patent Publication No. 4-10328, the hood having an opening formed on the side surface thereof for permitting a treatment tool, such as a knife, to be inserted through the opening. Another hood has been disclosed in WO94/11052, the hood having a tubular body, into which the endoscope is inserted and which has the end that can be opened for permitting a visual field to be maintained for the endoscope when the observation and treatment are performed. In Japanese Patent Publication No. 4-17648, a hood having a window which can be opened and closed for the treatment tool has been disclosed. In relation to the hoods disclosed as described above, a tracheal unit consisting of an outer tube and an internal needle has been disclosed in Japanese Utility Model Publication No. 61-7686 (corresponding to Laid-Open Publication No. 56-166006, the internal needle of the tracheal unit having a HF electrode attached thereto. In Japanese Patent Laid-Open No. 5-161660, a tracheal unit having a transparent leading end has been disclosed. The tracheal unit is combined with an endoscope and a laser beam unit.

As described above, in recent years, the treatment using an endoscope has been performed in a portion in which no cavity exists, as has been performed when the blood vessel in the human body is treated. In this case, also a technique is employed in which any of the various hoods is attached to the insertion portion of the endoscope; and the endoscope is moved forward while excising the portion between the tissues of the organism having no cavity. If the hood abuts against, for example, the fasciae between muscles during the operation of inserting the endoscope, only a sluggish operation using the hood encounters a great difficulty in incising the fasciae. If bleeding takes place unintentionally during the operation for excising the tissue, hemostasis is required. However, the conventional techniques cannot smoothly solve the foregoing problems.

That is, the technique disclosed in Japanese Patent Application No. 7-172139. permits only a sluggish operation to be performed such that the leading end of the hood is forcibly inserted into the tissue of the organism when, for example, an operation for incising the fasciae between the muscles is performed. Thus, the technique encounters a problem in that the operation efficiency cannot be improved. Moreover, when hemostasis of a bleeding portion is intended, a complicated operation is required such that another hemostasis means is, in parallel, inserted between tissues. The hood disclosed in Japanese Patent Publication No. 4-10328 and having the opening in the side surface thereof cannot effectively incise and/or excise the tissue of the organism in front of the endoscope in the case where the treatment tool, such as a knife, is inserted through the opening. Moreover, since no hemostasis means is provided, hemostasis of the bleeding portion cannot effectively be performed. Although the techniques disclosed in Japanese Patent Laid-Open No. 8-117181, Japanese Patent Publication No. 4-17648 and WO94/11052 are able to solve the foregoing problems by inserting an incising tool and a hemostasis tool into the body through the treatment tool channel of the endoscope, another problem arises in that the operation for inserting and drawing the treatment tool to and from the treatment tool channel of the endoscope and the operations of the treatment tools are too complicated. Since the technique disclosed in WO94/11052 has the structure such that the tubular body into which the endoscope is inserted is not transparent, the excising operation is required to be blindly performed. Thus, the operation cannot easily be completed and a problem arises in keeping safety.

SUMMARY OF THE INVENTION

An object of the present invention is to provide a system for evulsing subcutaneous tissue which is capable of easily and safely evulsing the subcutaneous tissue, represented by the subcutaneous blood vessel, such as the saphenous vein, while observing the portion to be evulsed through an endoscope.

The object of the present invention can be achieved by the following system for evulsing subcutaneous tissue: that is, according to one aspect of the present invention, there is provided a system for evulsing subcutaneous tissue, comprising: an endoscope adapted to be inserted into subcutaneous tissue through a skin cut portion in order to observe tissue below the skin which is a subject to be evulsed; an excising (dissecting) unit adapted to be inserted into the subcutaneous tissue through the skin cut portion and capable of excising the tissue, which is the subject to be evulsed, from surrounding tissue in order to form a cavity along the tissue, which is the subject to be evulsed, and below the skin; a cavity maintaining unit adapted to be inserted into the cavity formed by the excising unit through the skin cut portion and retained in the cavity in order to maintain a treatment space by itself around the tissue, which is the subject to be evulsed, for permitting the endoscope to be inserted and drawn and treatment of the tissue, which is the subject to be evulsed, to be performed; and at least one treatment tool adapted to be inserted into the treatment space maintained by the cavity maintaining unit to perform the treatment required to evulse the tissue, which is the subject to be evulsed, in the treatment space.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 4A is a plan view showing the excising member forming the system for evulsing subcutaneous tissue according to the first embodiment of the present invention;

FIG. 4B is a vertical cross sectional view showing the excising member shown in FIG. 4A;

FIG. 4C is a front view showing the excising member shown in FIG. 4A;

FIG. 4D is a vertical cross sectional view showing the leading end of the excising member shown in FIG. 4A;

FIG. 4E is a cross sectional view taken along line 4E—4E shown in FIG. 4D;

FIG. 4F is a cross sectional view taken along line 4F—4F shown in FIG. 4D;

FIG. 4G is a cross sectional view taken along line 4G—4G shown in FIG. 4D;

FIG. 8A is a perspective view showing a connection portion between the excising member and the tissue protective tool;

FIG. 8B is a vertical cross sectional view showing the connection portion in a state where the excising member and the tissue protective tool are connected to each other;

FIG. 9 is a perspective view showing a state where the tissue protective tool has been inserted between skin cut portions;

FIG. 18 shows an image observed with the hard endoscope;

FIG. 19A shows an image observed with the hard endoscope to illustrate a state where a hook probe is used;

FIG. 19B shows an image observed with the hard endoscope to illustrate a state where the hook probe is used;

FIG. 23A is a vertical cross sectional view showing a second example of the hook probe;

FIG. 23B is view showing the portion shown in FIG. 23A when viewed from a direction of an arrow 23B;

FIG. 24A is a vertical cross sectional view showing a third example of the hook probe;

FIG. 24B is a view showing the portion shown in FIG. 24A when viewed from a direction of an arrow 24B;

FIG. 27A is a perspective view showing a first modification of the tissue protective tool shown in FIG. 7A;

FIG. 27B is a cross sectional view taken along line 27B—27B shown in FIG. 27A;

FIG. 28A is a perspective view showing a second modification of the tissue protective tool and a first modification of the cavity forming tool;

FIG. 28B is a cross sectional view taken along line 28B—28B shown in FIG. 28A;

FIG. 28C is a cross sectional view taken along line 28C—28C shown in FIG. 28A;

FIG. 34 shows an image observed with the endoscope to illustrate a state in the cavity formed by the cavity maintaining tool shown in FIG. 29;

FIG. 35 shows an image observed with the endoscope to illustrate a state in the cavity formed by the cavity maintaining tool shown in FIG. 29;

FIG. 38 shows an image observed with the endoscope to illustrate a state in the cavity formed by the cavity maintaining tool shown in FIG. 29;

FIG. 39 is a perspective view showing a second modification of the cavity maintaining tool;

FIG. 46A is a perspective view showing a seventh modification of the cavity maintaining tool;

FIG. 46B is a cross sectional view showing a state where the cavity maintaining tool shown in FIG. 46A is retained below the skin;

FIG. 47 is a perspective view showing an eighth modification of the cavity maintaining tool;

FIG. 48A is a perspective view showing a ninth modification of the cavity maintaining tool;

FIG. 48B is a perspective view showing a state where the cavity maintaining tool shown in FIG. 48A is used:

FIG. 60A is a perspective view showing an assembled state of the cavity maintaining tool according to a thirteenth modification;

FIG. 60B is an exploded perspective view showing the cavity maintaining tool according to the thirteenth modification;

FIG. 60C is an exploded cross sectional view showing the cavity maintaining tool according to the thirteenth modification;

FIG. 62A is an assembled perspective view showing a cavity maintaining tool according to a fifteenth modification;

FIG. 62B is an exploded perspective view showing the cavity maintaining tool according to the fifteenth modification;

FIG. 63A is an assembled perspective view showing a cavity maintaining tool according to a sixteenth modification;

FIG. 63B is an exploded perspective view showing the cavity maintaining tool according to the sixteenth modification;

FIG. 64A is an assembled perspective view showing a cavity maintaining tool according to a seventeenth modification;

FIG. 64B is an exploded perspective view showing the cavity maintaining tool according to the seventeenth modification;

FIG. 66B is a side cross sectional view of FIG. 66A;

FIG. 67A is a diagram showing a state where the saphenous vein and the connective tissue are excised by using the guide member shown in FIG. 65A;

FIG. 67B is a side cross sectional view of FIG. 67A;

FIG. 67C is a cross sectional view taken along line 67C—67C shown in FIG. 67B;

FIG. 68A is a diagram showing a state where the connective tissue is cut by using the pincers guided by the guide member shown in FIG. 65A;

FIG. 68B is a side cross sectional view of FIG. 68A;

FIG. 69A is a perspective view showing a second example of the guide member;

FIG. 69B is horizontal cross sectional view showing the guide member shown in FIG. 69A;

FIG. 69C is a vertical cross sectional view showing the guide member shown in FIG. 69A;

FIG. 70 is a perspective view showing a third example of the guide member;

FIG. 71A is a horizontal cross sectional view showing the guide member shown in FIG. 70;

FIG. 71B is a vertical cross sectional view showing the guide member shown in FIG. 70;

Figure 10A:
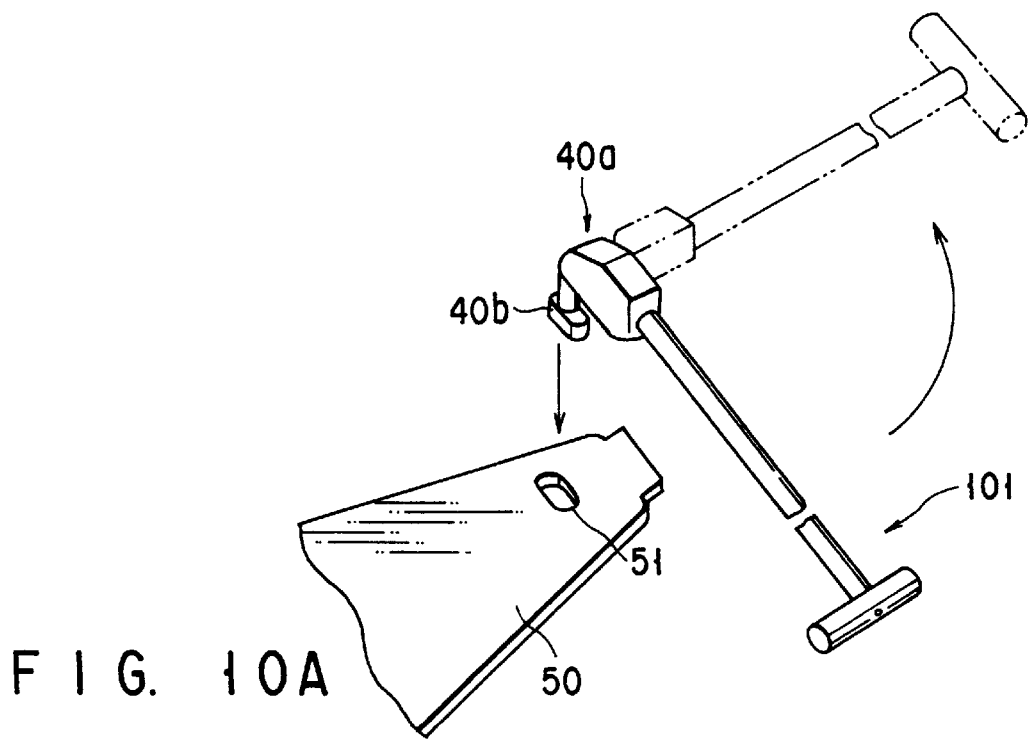
FIG. 10A is perspective view showing a state where a dilator hook is connected to a cavity forming tool.
Figure 11A:
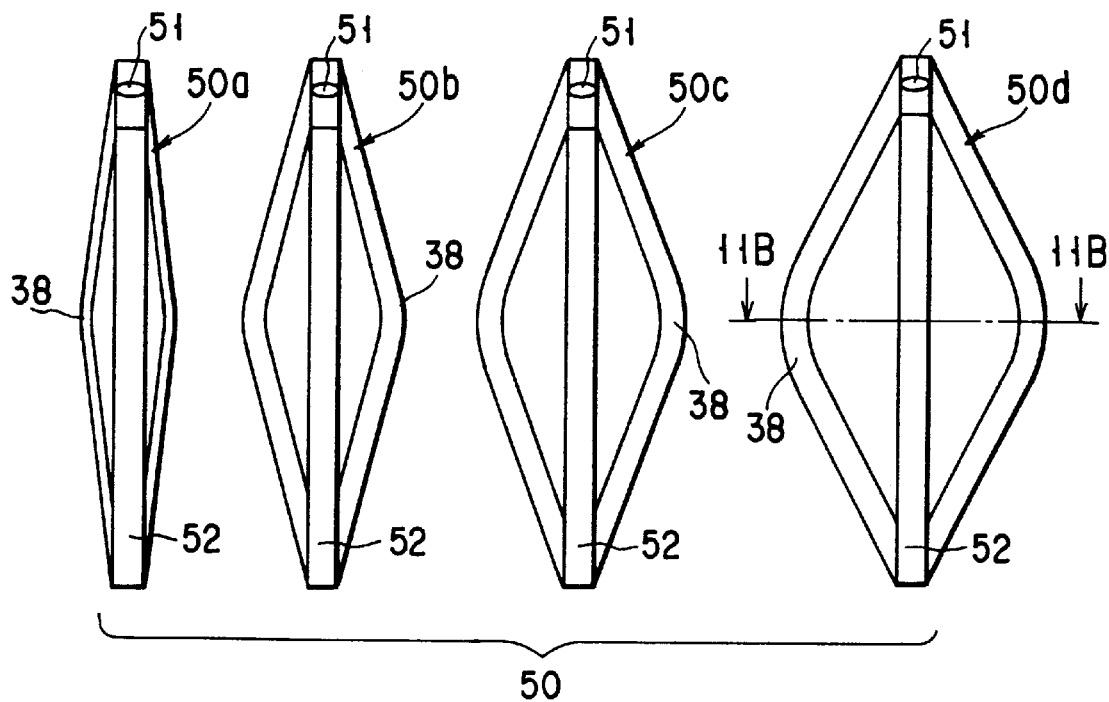
FIG. 11A is a rear view showing the cavity forming tool.
Figure 11B:
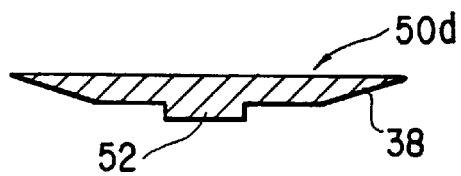
FIG. 11B is a cross sectional view taken along line 11B—11B shown in FIG. 11A.
Figure 70:
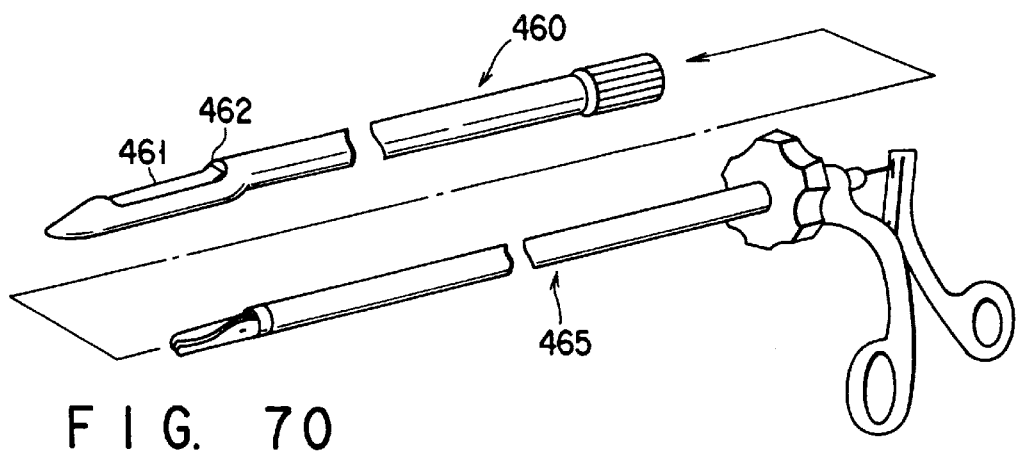
Figure 71A:
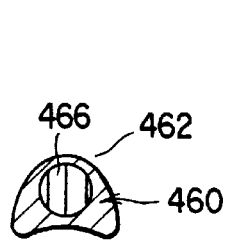
Figure 71B:
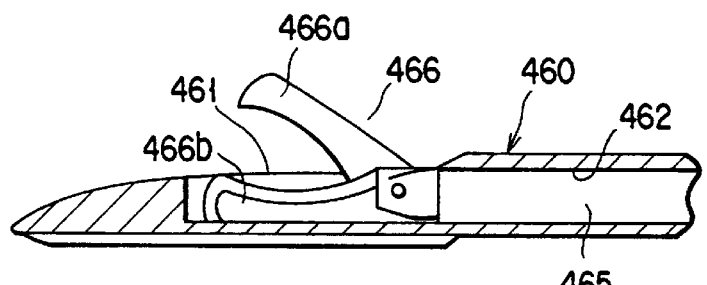
Figure 71C:
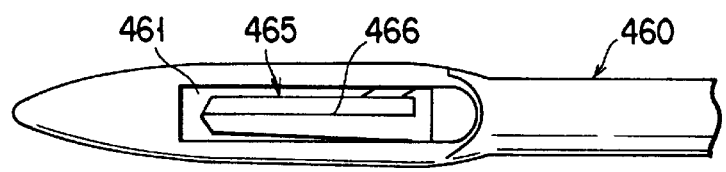
Figure 72A:
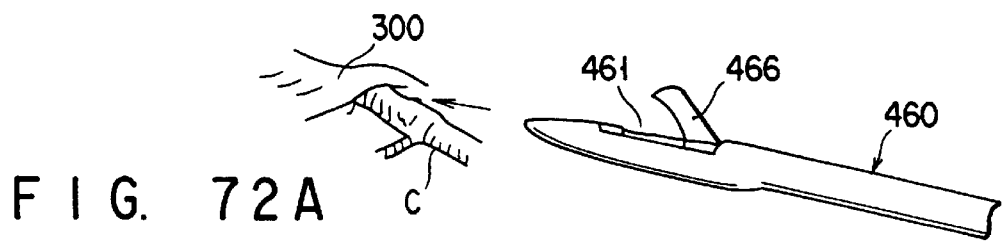
Figure 72B:
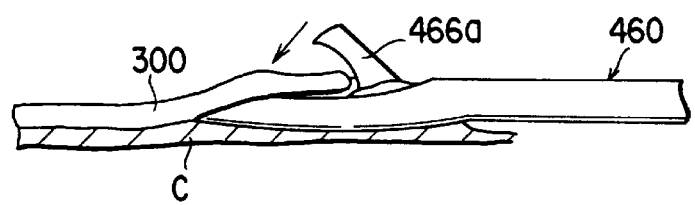
Figure 74:
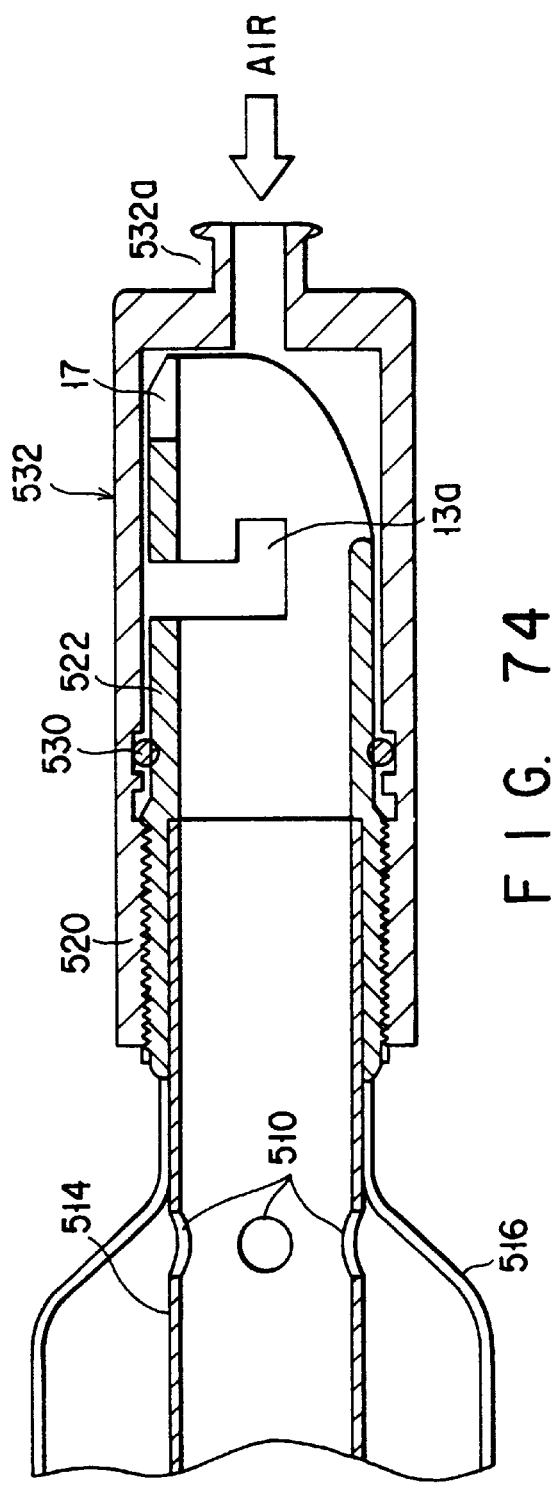
Figure 75:
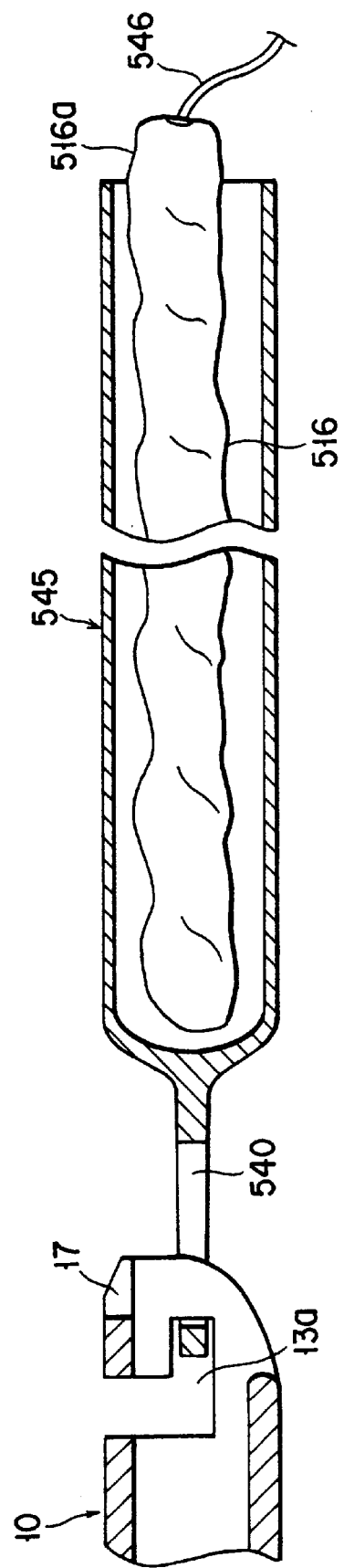
Figure 76:
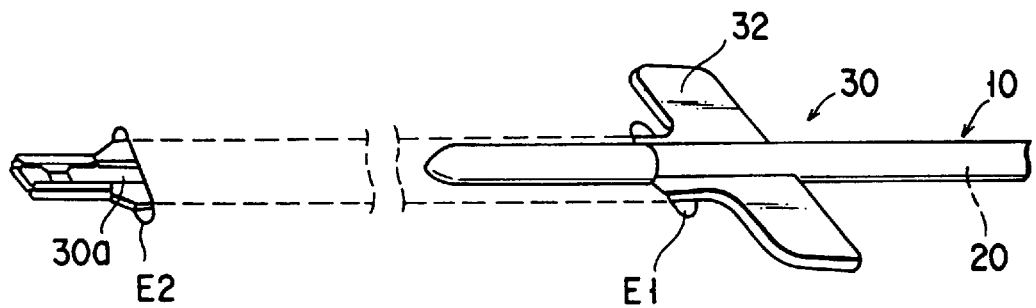
Figure 77:
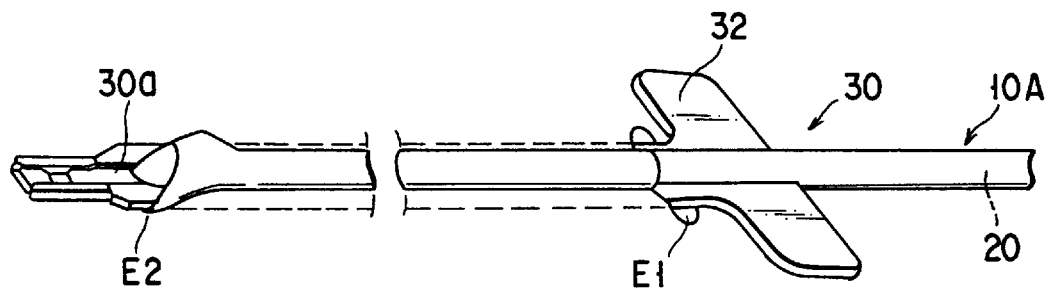
Figure 78:
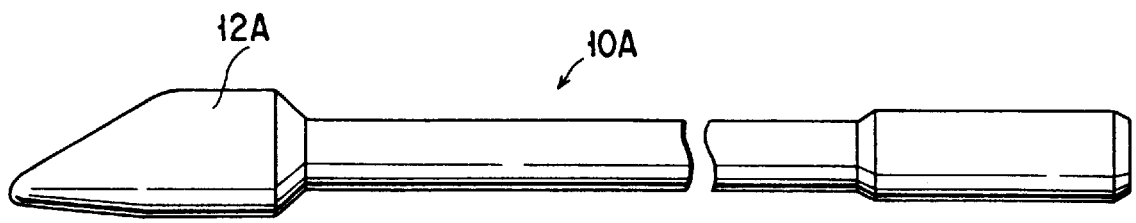
Figure 80:
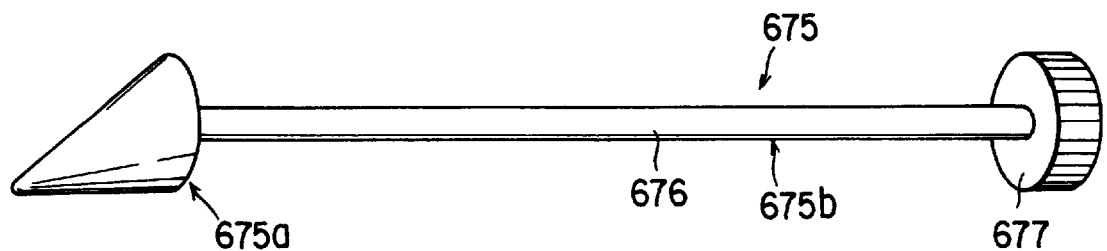
Figure 81:
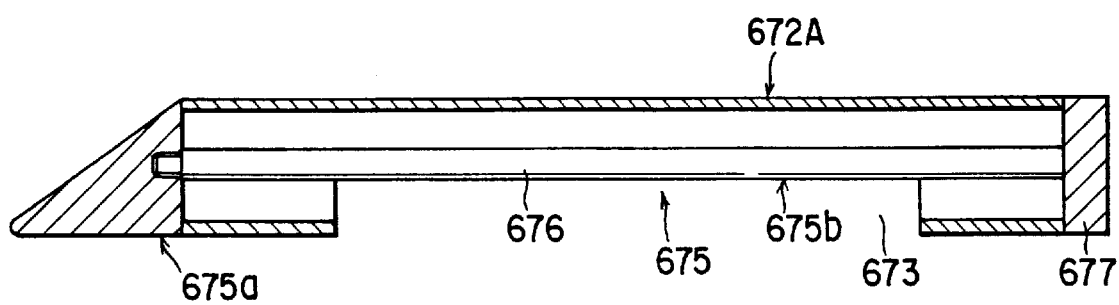
Figure 82:
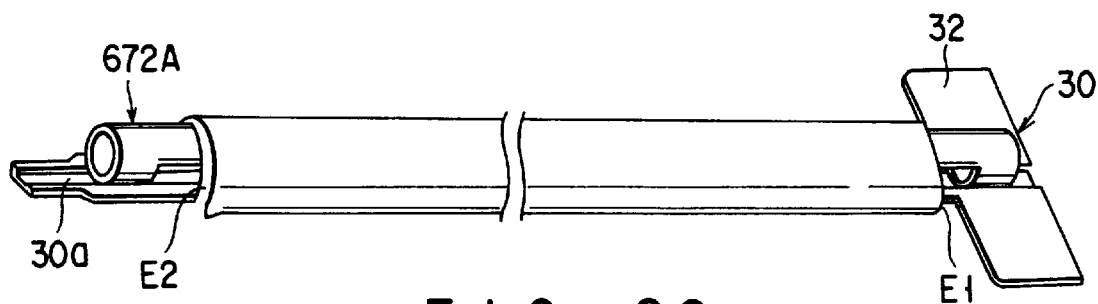
Figure 83:
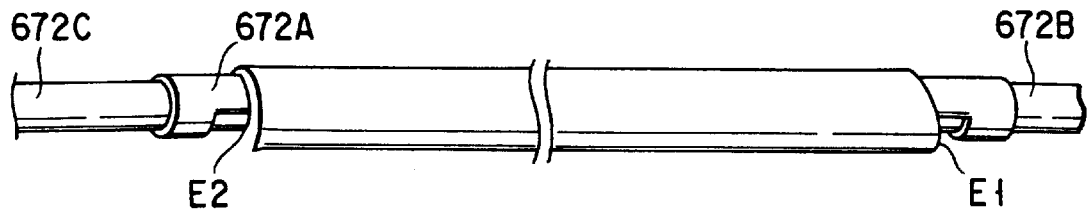
Figure 87:
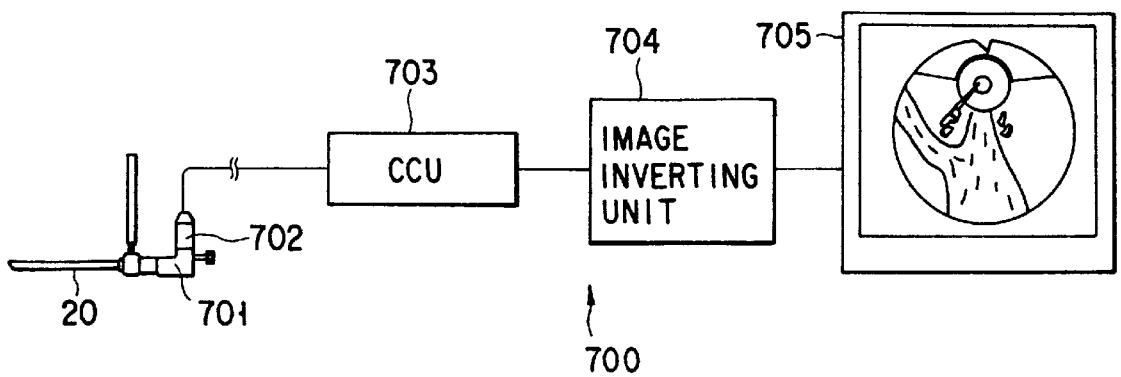
Figure 88A:
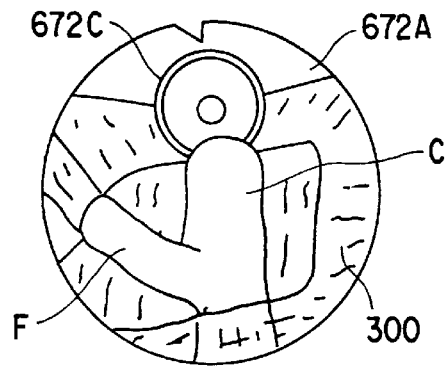
Figure 88B:
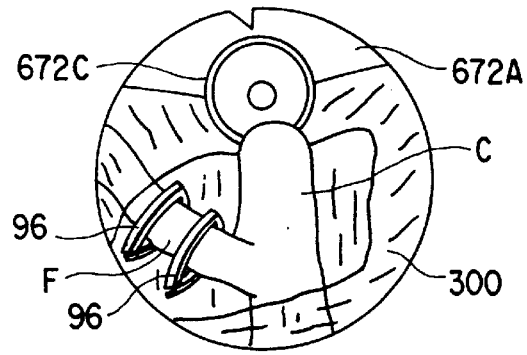
Figure 88C:
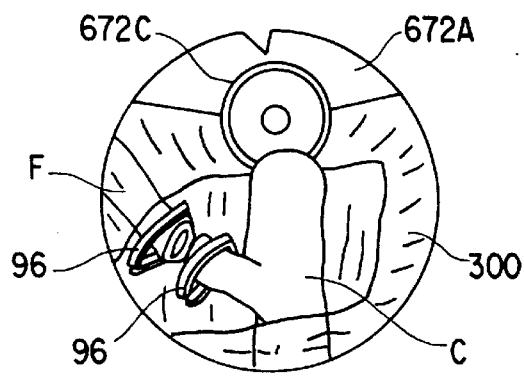
Figure 89:
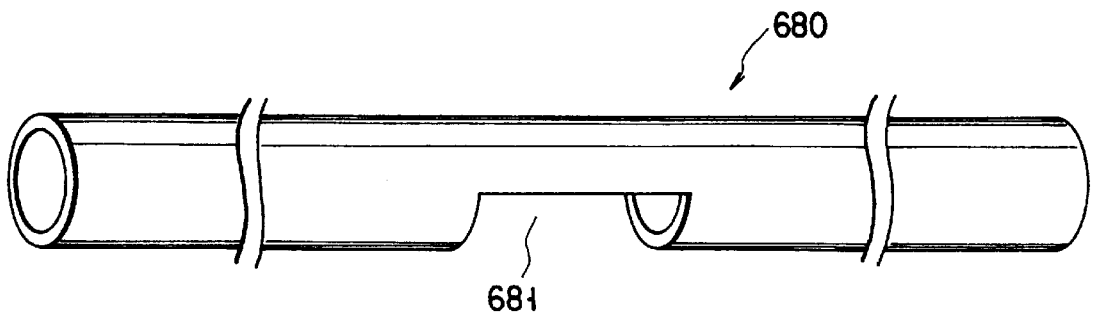
Figure 90A:
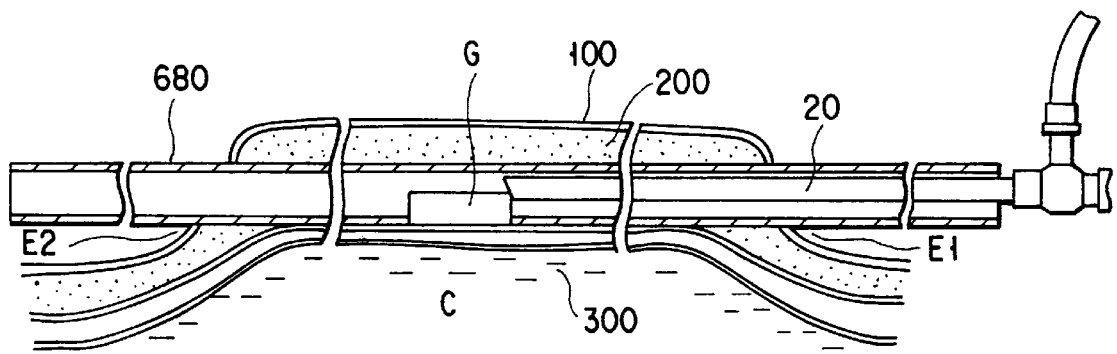
Figure 90B:
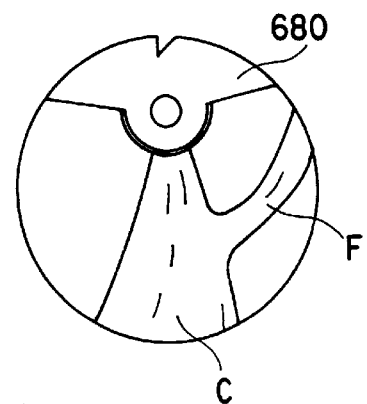
Figure 91A:
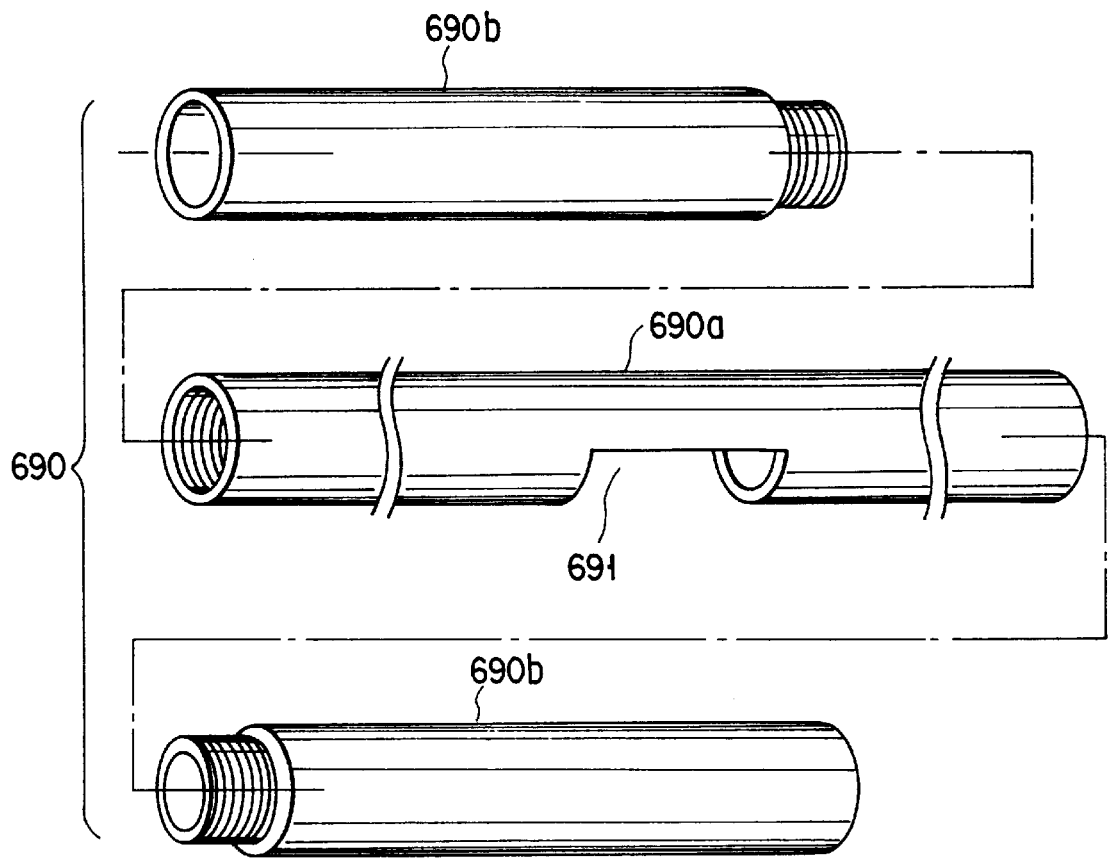
Figure 91B:
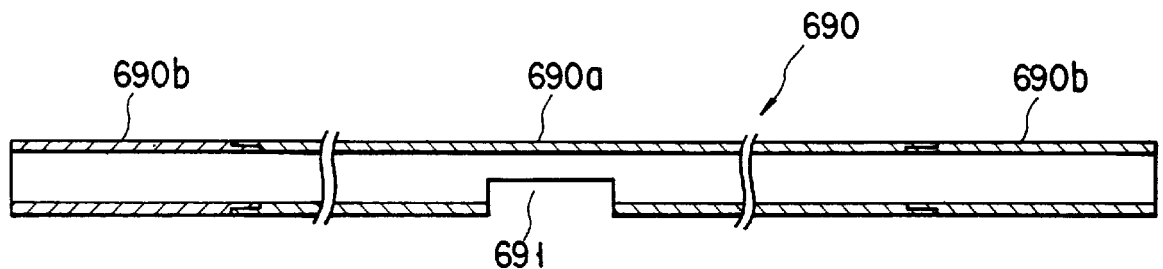
Figure 92:
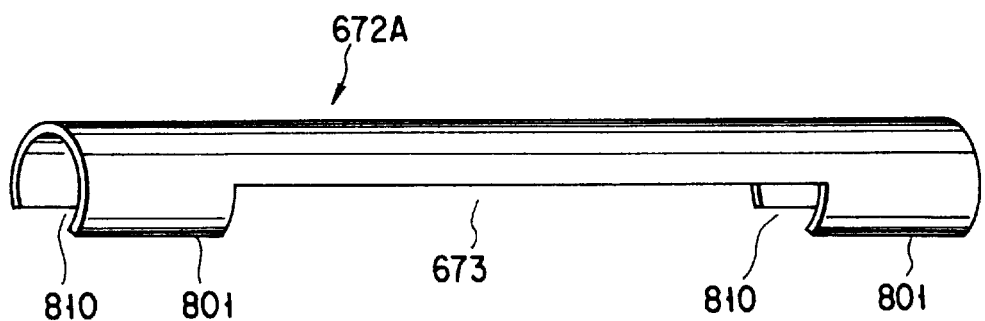
Figure 93:
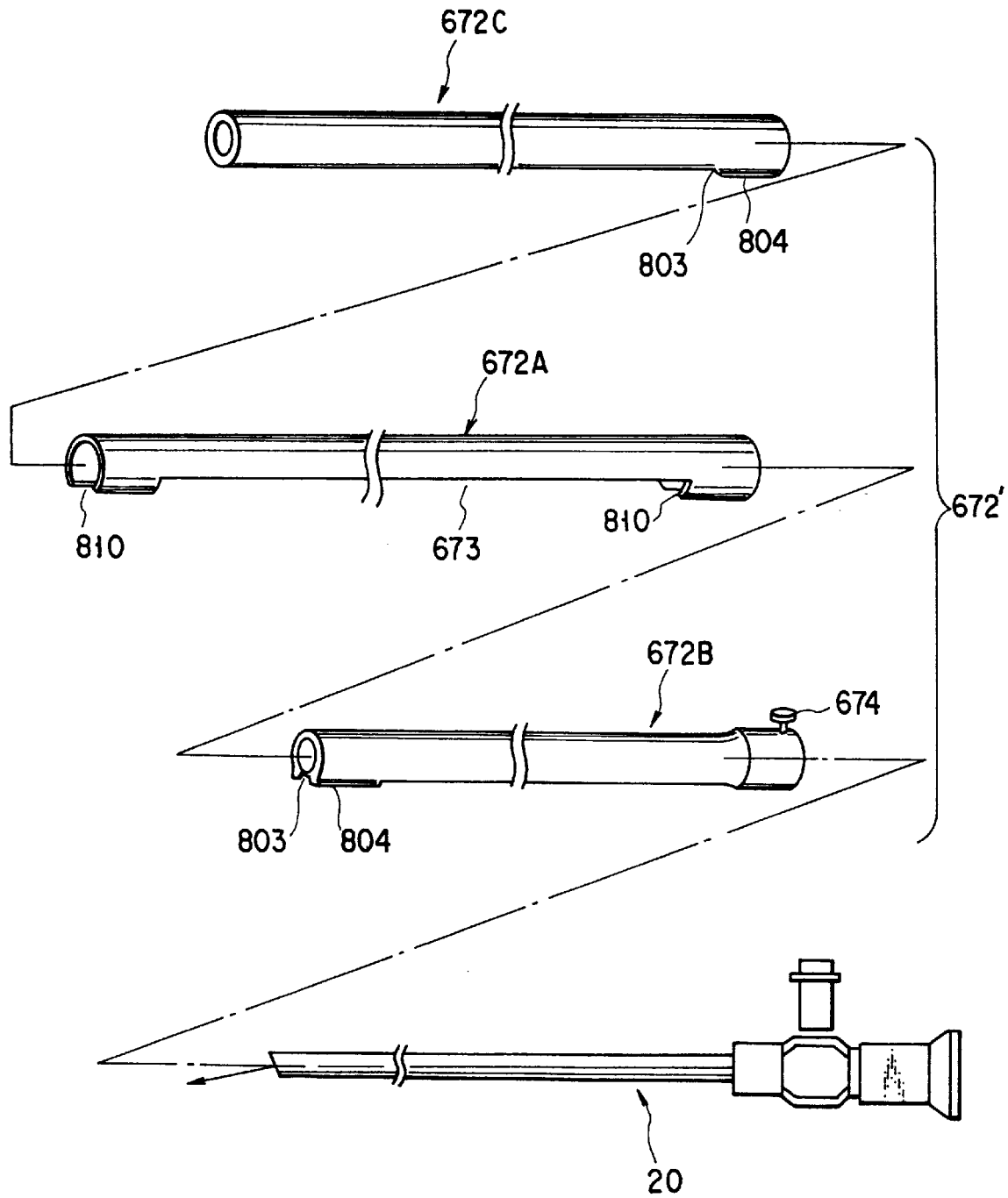
Figure 102A:
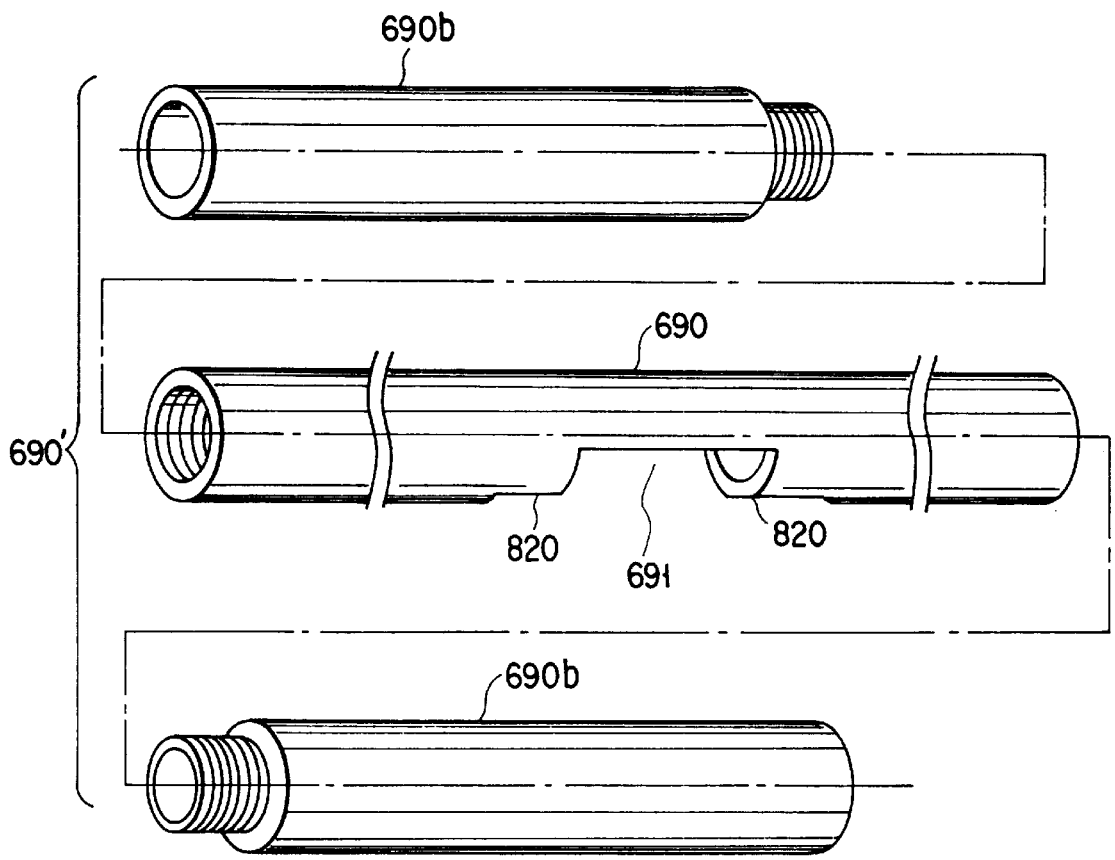
Figure 102B:
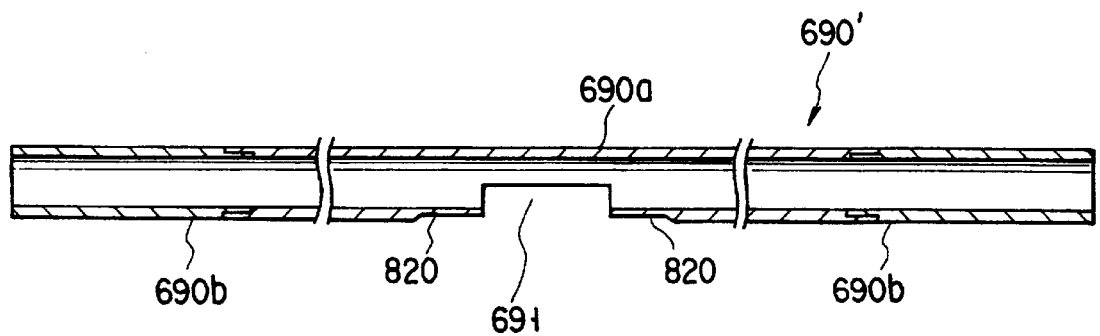
Figure 103A:
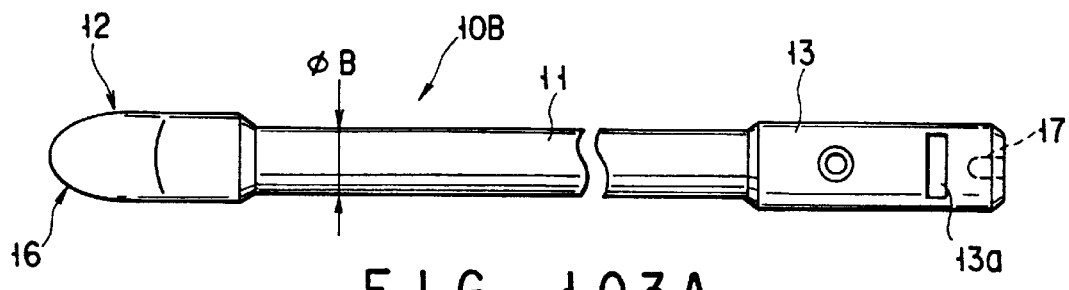
Figure 103B:
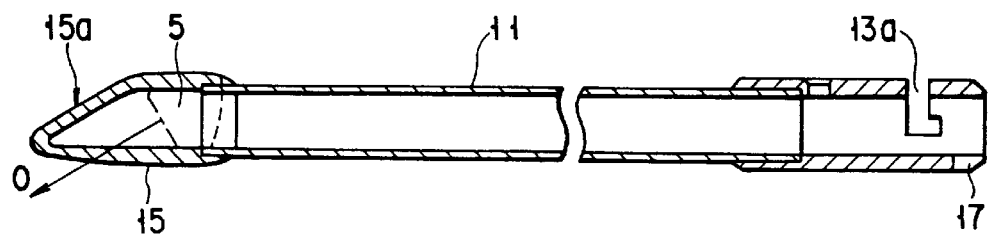
Figure 104A:
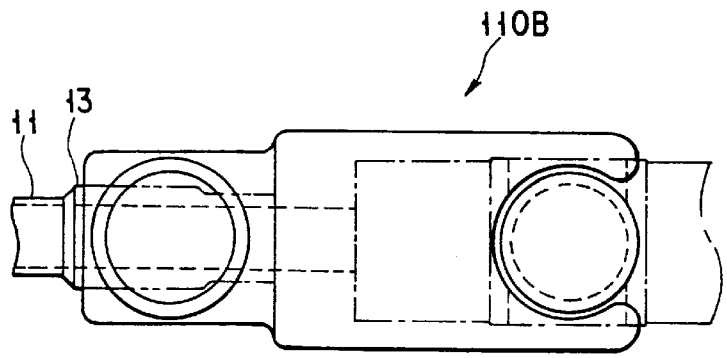
Figure 104B:
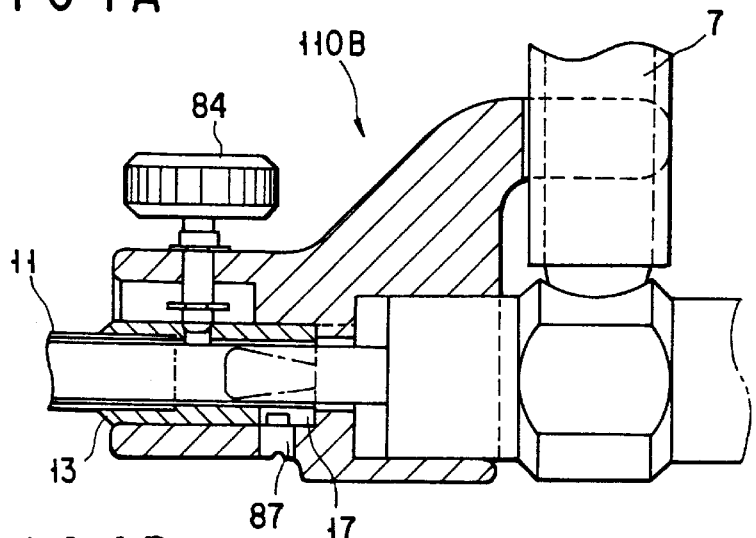
Figure 105A:
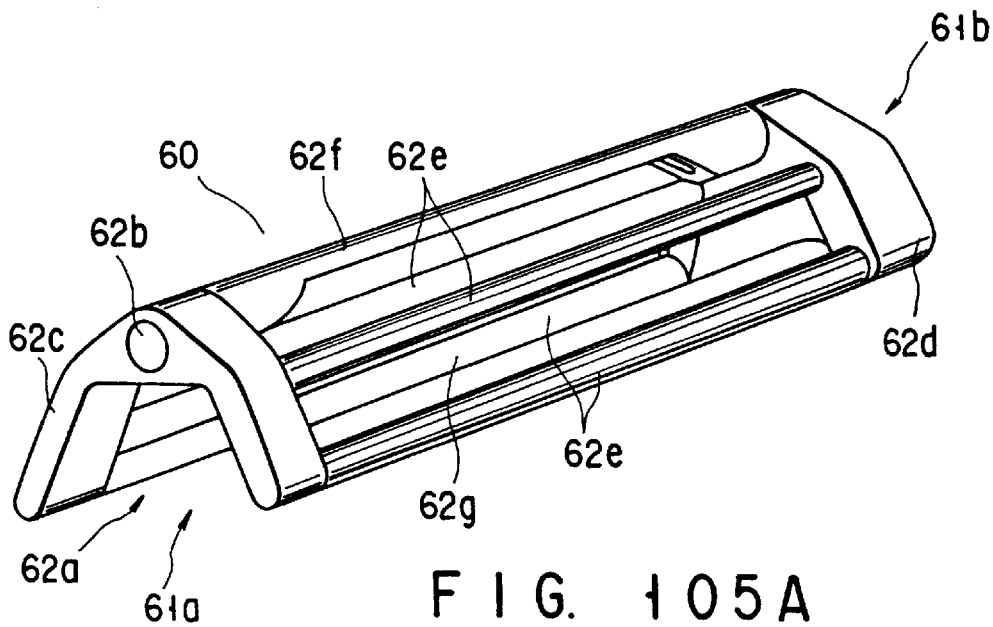
Figure 105B:
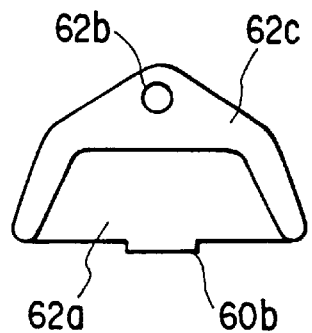
Figure 105C:
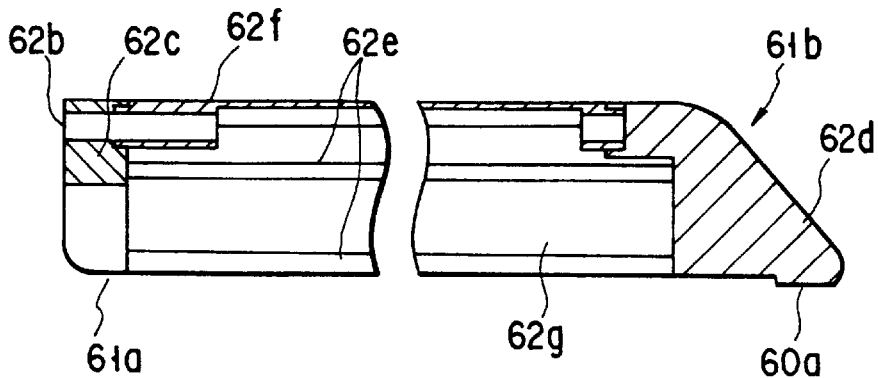
Figure 106:
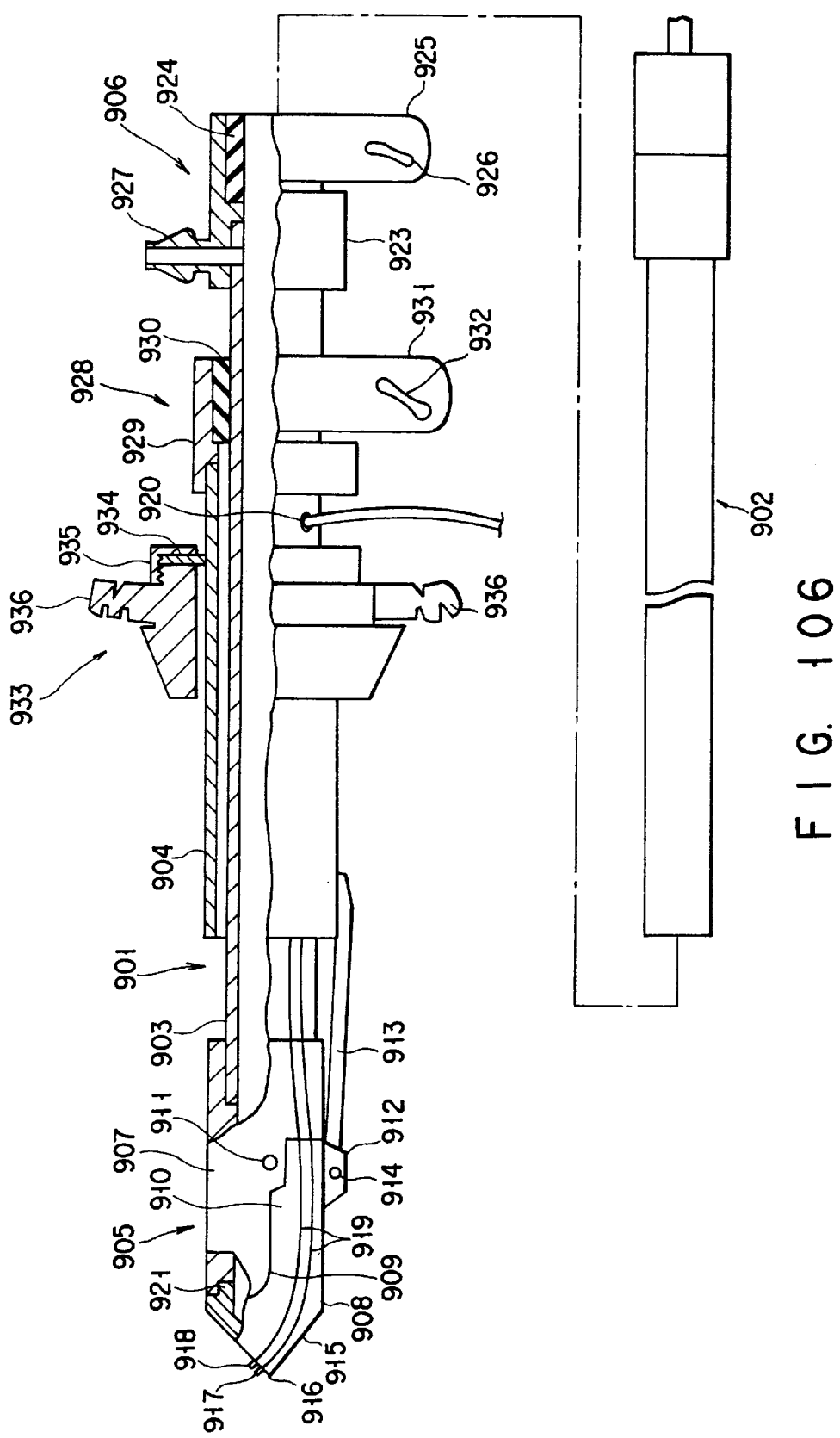
Figure 107A:
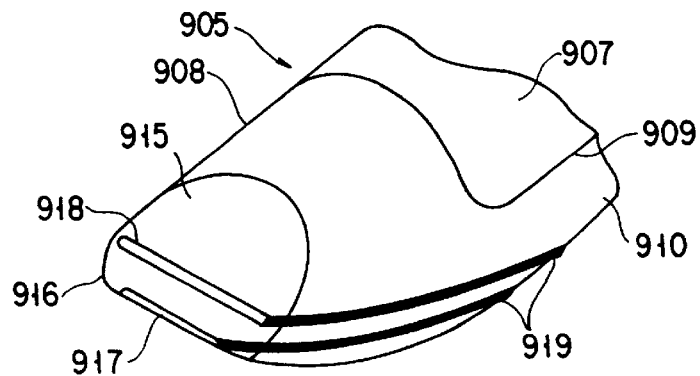
Figure 107B:
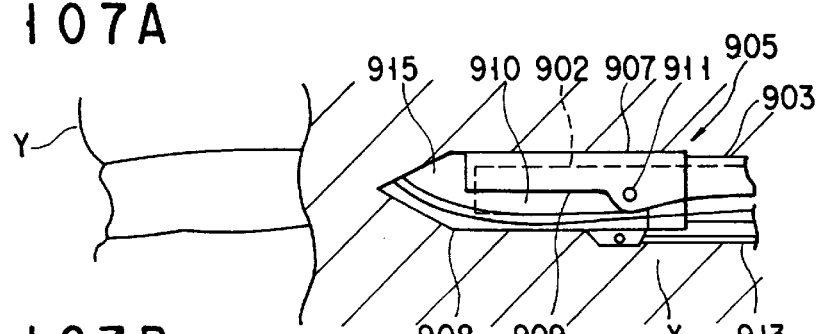
Figure 107C:
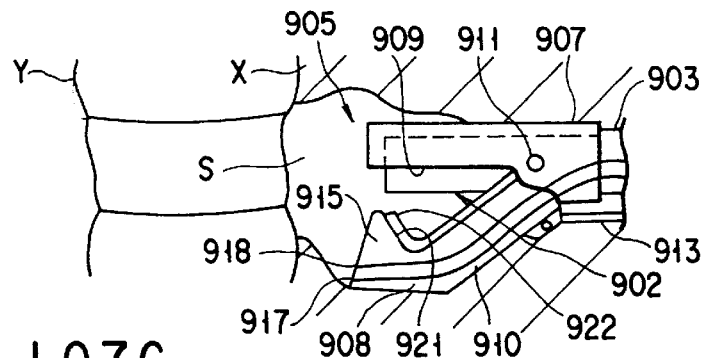
Figure 107D:
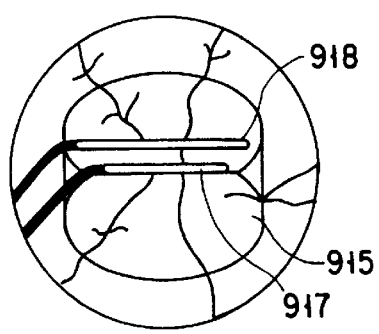
Figure 107E:
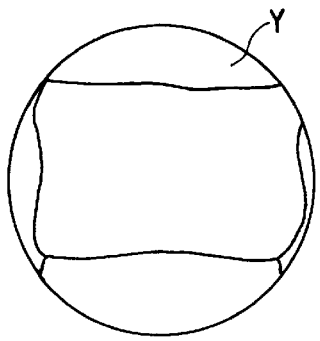
Figure 108A:
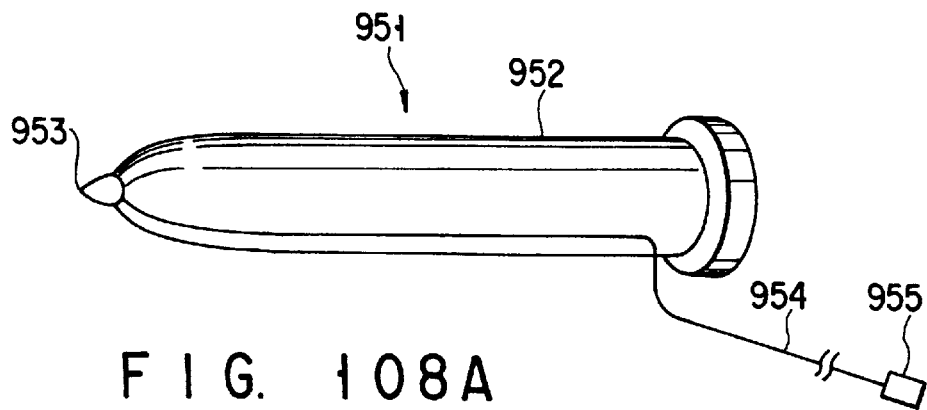
Figure 108B:
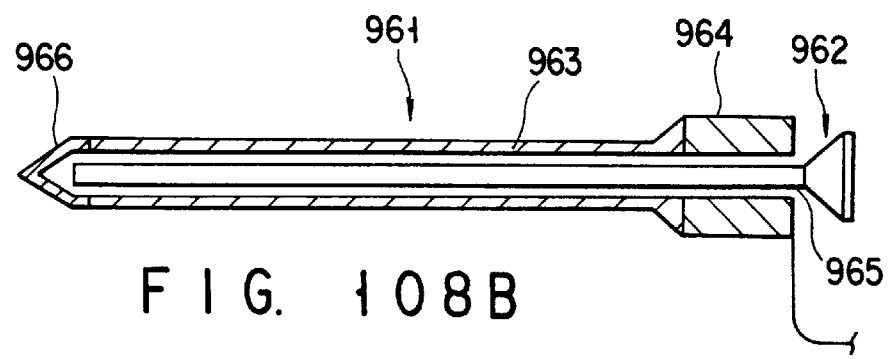
Figure 108C:
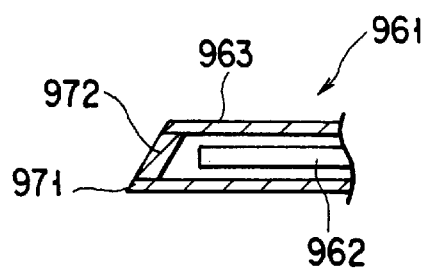
Figure 109:
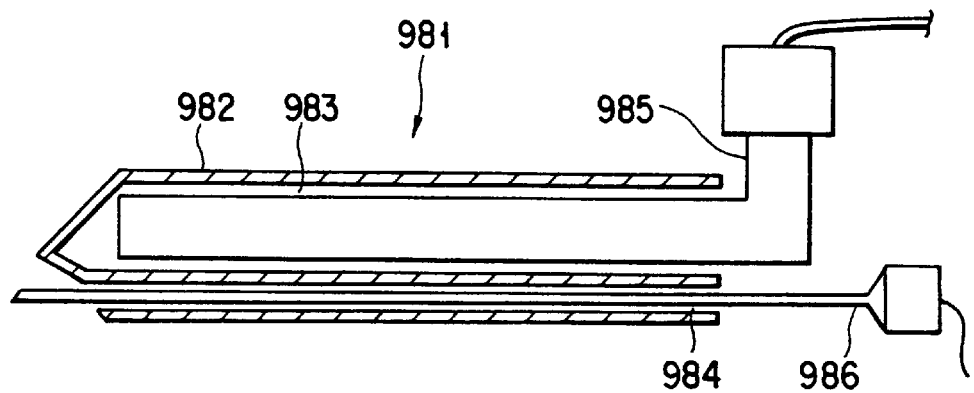
Figure 110A:
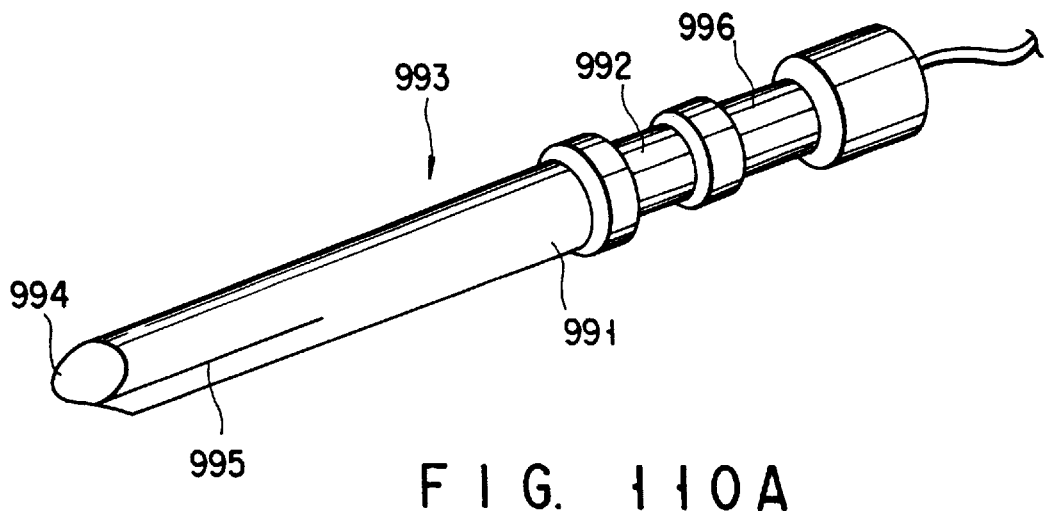
Figure 110B:
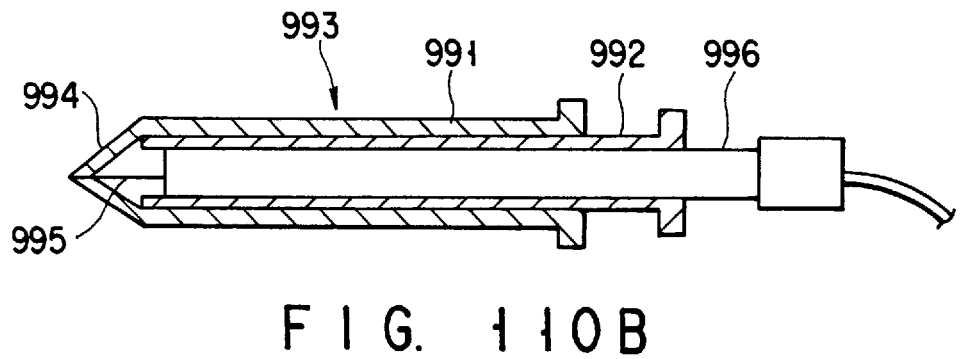
Figure 110C:
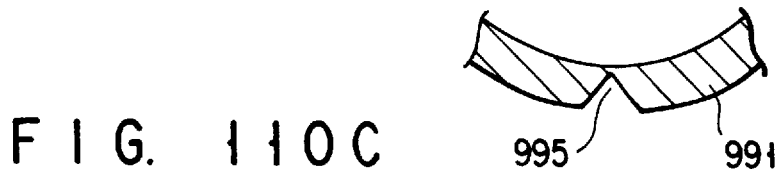
Figure 110D:
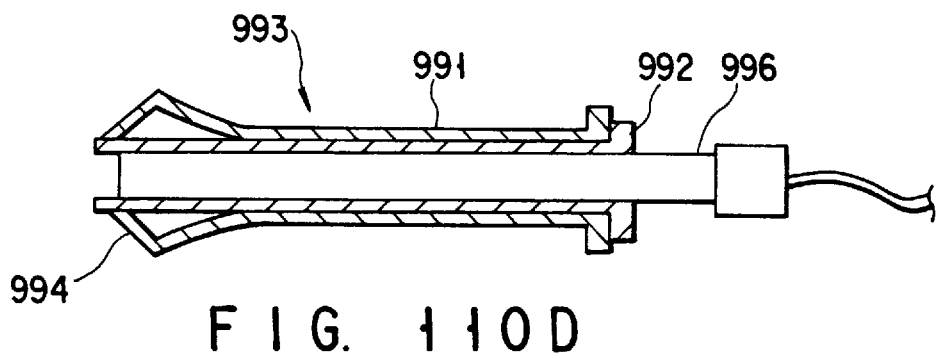

FIG. 71C is a plan view showing the guide member shown in FIG. 70;

FIG. 72A is a diagram showing a state where the connective tissue is cut by using the guide member and the treatment tool shown in FIG. 70;

FIG. 72B is a side cross sectional view of FIG. 72A;

FIG. 73 is a side cross sectional view showing a second modification of the excising member;

FIG. 74 is a side cross sectional view showing a state where a balloon of the excising member shown in FIG. 73 has been expanded;

FIG. 75 is a side cross sectional view showing a modification of the excising member shown in FIG. 73;

FIG. 76 is a diagram showing a state of the system for evulsing subcutaneous tissue according to a second embodiment of the present invention where the excising member is inserted through either of the skin cut portions while being moved along a groove in the top surface of the tissue protective tool to reach the residual skin cut portion;

FIG. 77 is a diagram showing a state where the excising member forming the system for evulsing subcutaneous tissue according to the second embodiment is inserted through either of the skin cut portions while being moved along a groove in the top surface of the tissue protective tool to reach the residual skin cut portion;

FIG. 78 is a side view showing the excising member forming the system for evulsing subcutaneous tissue according to the second embodiment;

FIG. 79 is an exploded perspective view showing a cavity maintaining tool forming the system for evulsing subcutaneous tissue according to the second embodiment;

FIG. 80 is a perspective view showing an insertion helper for guiding and helping insertion of an outer tube of the cavity maintaining tool shown in FIG. 79;

FIG. 81 is a side cross sectional view showing a state where the insertion helper shown in FIG. 80 is attached to the outer tube of the cavity maintaining tool shown in FIG. 79;

FIG. 82 is a perspective view showing a state where the outer tube of the cavity maintaining tool shown in FIG. 79 has been inserted into the subcutaneous tissue;

FIG. 83 is a diagram showing a state where an inner tube is inserted into the outer tube in a state shown in FIG. 82;

FIG. 84A is a vertical cross sectional view of FIG. 83;

FIG. 84B is a cross sectional view taken along line 84B—84B shown in FIG. 84A;

FIG. 84C is a cross sectional view taken along line 84C—84C shown in FIG. 84A;

FIG. 85A is a vertical cross sectional view showing a state where the hard endoscope has been inserted into the inner tube in the state shown in FIG. 84A;

FIG. 85B shows an image observed with the endoscope in the state shown in FIG. 85A;

FIG. 86A is a vertical cross sectional view showing a state where the hook probe has been inserted into the inner tube in the state shown in FIG. 85A;

FIG. 86B shows an image observed with the endoscope in the state shown in FIG. 86A;

FIG. 87 is a schematic view showing the structure of the endoscope system;

FIG. 88A shows an image observed by the endoscope;

FIG. 88B shows an image observed by the endoscope;

FIG. 88C shows an image observed by the endoscope;

FIG. 89 is a perspective view showing a cavity maintaining tool according to a first modification of the second embodiment;

FIG. 90A is a vertical cross sectional view showing a state where the hard endoscope has been inserted into the inner tube in a state where the cavity maintaining tool shown in FIG. 89 has been inserted into the subcutaneous tissue;

FIG. 90B shown an image observed by the endoscope in the state shown in FIG. 90A;

FIG. 91A is an exploded perspective view showing a cavity maintaining tool according to a second modification of the second embodiment;

FIG. 91B is a vertical cross sectional view showing the cavity maintaining tool shown in FIG. 91A in an assembled state;

FIG. 92 is a perspective view showing the outer tube of a cavity maintaining tool according to a third Modification of the second embodiment;

FIG. 93 is an exploded perspective view showing the cavity maintaining tool according to the third modification of the second embodiment;

FIG. 94 is a side cross sectional view showing a state where the insertion helper shown in FIG. 80 has been attached to the outer tube shown in FIG. 92;

FIG. 95 is a perspective view showing a state where the outer tube of the cavity maintaining tool shown in FIG. 92 has been inserted into the subcutaneous tissue;

FIG. 96 is a diagram showing a state where the inner tube has been inserted into the outer tube in the state shown in FIG. 95;

FIG. 97A is a vertical cross sectional view of FIG. 96;

FIG. 97B is a cross sectional view taken along line 97B—97B shown in FIG. 97A;

FIG. 97C is a cross sectional view taken along line 97C—97C shown in FIG. 97A;

FIG. 98A is a vertical cross sectional view showing a state where the hard endoscope has been inserted into the inner tube in the state shown in FIG. 97A;

FIG. 98B shows an image observed with the endoscope in the state shown in FIG. 98A;

FIG. 99A is a vertical cross sectional view showing a state where the hook probe has been inserted into the inner tube in the state shown in FIG. 98A;

FIG. 99B shown an image observed with the endoscope in the state shown in FIG. 99A;

FIG. 100 is a perspective view showing a cavity maintaining tool according to a fourth modification of the second embodiment;

FIG. 101A is a vertical cross sectional view showing a state where the hard endoscope has been inserted into the inner tube in the state where the cavity maintaining tool shown in FIG. 100 has been inserted into the subcutaneous tissue;

FIG. 101B shows an image observed with the endoscope in the state shown in FIG. 101A;

FIG. 102A is an exploded perspective view showing a cavity maintaining tool according to a fifth modification of the second embodiment;

FIG. 102B is a vertical cross sectional view showing a state where the cavity maintaining tool shown in FIG. 102A has been assembled;

FIG. 103A is a plan view showing a modification of the excising member according to the first embodiment;

FIG. 103B is a vertical cross sectional view of FIG. 103A;

FIG. 104A is a plan view showing a sheath holder according to a modification of the first embodiment which has been set to the endoscope together with the excising member shown in FIG. 103A;

FIG. 104B is a vertical cross sectional view showing an assembly set as shown in FIG. 104A;

FIG. 105A is a perspective view showing a modification of the cavity maintaining tool according to the first embodiment;

FIG. 105B is a front view showing the cavity maintaining tool shown in FIG. 105A;

FIG. 105C is a vertical cross sectional view showing the cavity maintaining tool shown in FIG. 105A;

FIG. 106 is a cross sectional view showing a first embodiment of a hood for an endoscope;

FIG. 107A is a perspective view showing the leading end of the hood for an endoscope shown in FIG. 106;

FIG. 107B is a vertical cross sectional view showing a state where excision of tissue is performed by using the hood for an endoscope shown in FIG. 106;

FIG. 107C is a vertical cross sectional view showing a state where the hood has been opened after the excision of tissue has been performed by using the hood for an endoscope shown in FIG. 106;

FIG. 107D shows an image obtained with the endoscope in the state shown in FIG. 107B;

FIG. 107E shows an image obtained with the endoscope in the state shown in FIG. 107C;

FIG. 108A is a vertical cross sectional view showing a second embodiment of the hood for an endoscope;

FIG. 108B is a vertical cross sectional view showing a third embodiment of the hood for an endoscope;

FIG. 108C is a vertical cross sectional view showing a fourth embodiment of the hood for an endoscope;

FIG. 109 is a vertical cross sectional view showing a fifth embodiment of the hood for an endoscope;

FIG. 110A is a perspective view showing a sixth embodiment of the hood for an endoscope;

FIG. 110B is a vertical cross sectional view showing a state where the opening at the leading end of the hood for an endoscope shown in FIG. 110A is closed;

FIG. 110C is a horizontal cross sectional view showing an engraved stripe portion of the hood for an endoscope shown in FIG. 10A;

FIG. 110D is a vertical cross sectional view showing a state where the opening at the leading end of the hood for an endoscope shown in FIG. 110A is opened;

FIG. 111A is a vertical cross sectional view showing a seventh embodiment of the hood for an endoscope;

FIG. 111B is a vertical cross sectional view showing a state where a shutter member of the hood for an endoscope shown in FIG. 111A is opened;

FIG. 112 is cross sectional view taken along line 112—112 shown in FIG. 11A;

FIG. 113A is a vertical cross sectional view showing a state where observation is performed through the opening of a transparent sheath of the hood for an endoscope according to an eighth embodiment; and FIG. 113B is a vertical cross sectional view showing a state where observation is performed through the transparent portion of the transparent sheath of the hood for an endoscope according to the eighth embodiment.

DETAILED DESCRIPTION OF THE PREFERRED EMBODIMENTS

Referring to the drawings, preferred embodiments of the present invention will now be described with reference to the drawings.

FIGS. 1 to 19B show a first embodiment of the present invention. Prior to describing a system for evulsing subcutaneous tissue according to this embodiment, a procedure for evulsing the blood vessel in the lower extremity by the system for evulsing subcutaneous tissue according to this embodiment by means of an endoscope will now be described with reference to FIGS. 1 and 2E.

Figure 1:
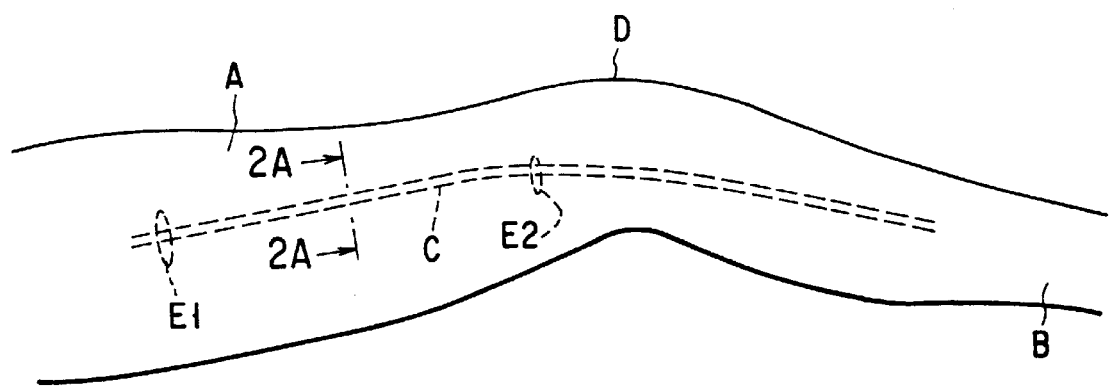
FIG. 1 is diagram showing a state where a skin cut portion is formed in the lower extremity to apply a system for evulsing subcutaneous tissue according to a first embodiment of the present invention.

FIG. 1 shows the lower extremity. When a blood vessel (hereinafter simply called as "blood vessel"), such as the saphenous vein extending from the inguinal region A of the thigh to the knee D and intended to be evulsed, is evulsed, a skin cut portion E1 is, by a knife or the like, formed in the inguinal region A of the thigh at a position just above the blood vessel C. Then, the blood vessel C is exposed through the skin cut portion E1 by a pair of peeling forceps or the like. Then, the tissue just above the blood vessel C is dissected similarly by a pair of peeling forceps for a distance which can be observed by the naked eye through the skin cut portion E1.

Figure 2A:
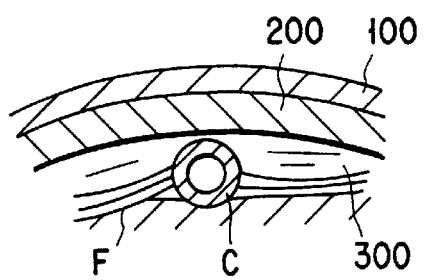
FIG. 2A is a cross sectional view taken along line 2A—2A of FIG. 1.
Figure 2B:
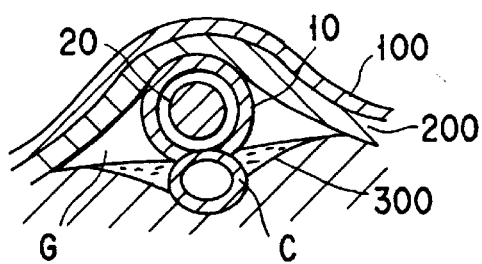
FIG. 2B is a cross sectional view showing a state where an excising member has been inserted into the subcutaneous tissue and corresponding to FIG. 2A.
Figure 2C:
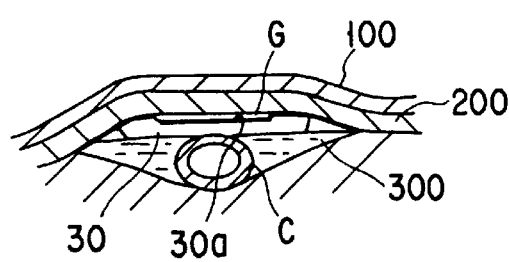
FIG. 2C is a cross sectional view showing a state where a tissue protective tool has been inserted into the subcutaneous tissue and corresponding to FIG. 2A.
Figure 2D:
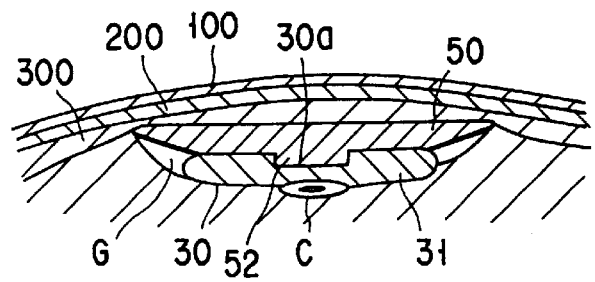
FIG. 2D is a cross sectional view showing a state where the tissue protective tool and a cavity forming tool have been inserted into the subcutaneous tissue and corresponding to FIG. 2A.
Figure 2E:
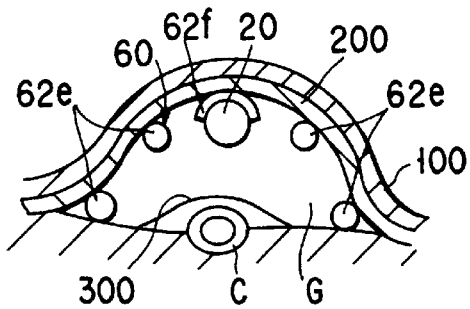
FIG. 2E is a cross sectional view showing a state where a cavity maintaining tool has been inserted into the subcutaneous tissue and corresponding to FIG. 2A.
Figure 3:
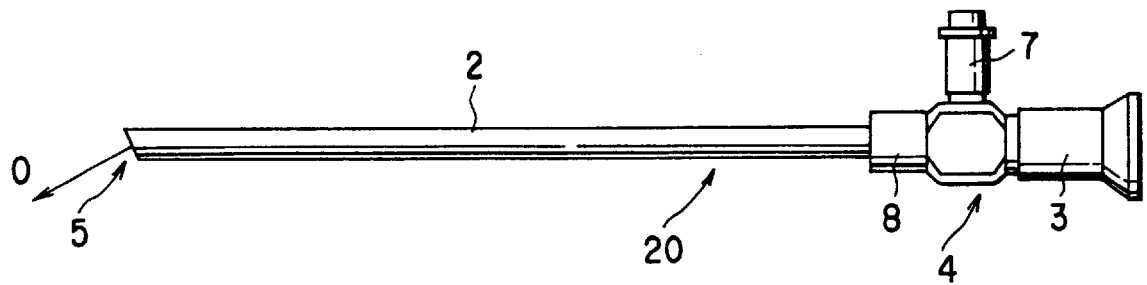
FIG. 3 is a side view showing a hard endoscope forming the system for evulsing subcutaneous tissue according to the first embodiment of the present invention.

FIG. 2A is a cross sectional view taken along line 2A—2A shown in FIG. 1. Referring to FIG. 2E, reference numeral 100 represents a skin, 200 represents a subcutaneous tissue and 300 represents a connective tissue on the blood vessel C. The blood vessel C exists below the connective tissue 300 on the blood vessel C. When the blood vessel C is evulsed in the state shown in FIG. 2A, the excising member 10 shown in FIG. 4A is used to separate the blood vessel C and the surrounding tissues from each other so that cavity G is formed, as shown in FIG. 2B. In the foregoing case, the hard endoscope 20 shown in FIG. 3 is inserted into the excising member 10 followed by being secured. Then, the leading end of the excising member 10 is, through the skin cut portion E1 in the inguinal region A, inserted along the portion above the blood vessel C toward the knee D. Since the leading end of the excising member 10 is made of a transparent member, the blood vessel C and its side branch F can clearly be observed through the hard endoscope 20 during the foregoing process. The excising member 10 is inserted gradually in such a manner that the excising member 10, slightly, is moved forward and rearward while observing the movement of blood vessel C through the hard endoscope 20. As a result, the excising member 10 is inserted to a position near the knee D along the blood vessel C. Then, the skin just above the leading end of the excising member 10 is incised so that skin cut portion E2 is formed, followed by penetrating the leading end of the excising member 10 to the outside of the body through the skin cut portion E2.

Figure 7A:
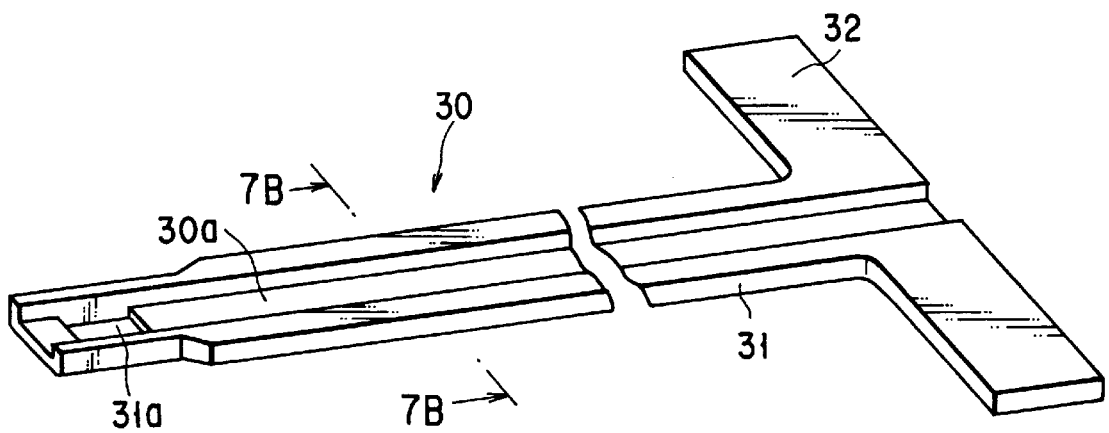
FIG. 7A is a perspective view showing the tissue protective tool forming the system for evulsing subcutaneous tissue according to the first embodiment.

Then, while leaving the excising member 10 in the body, the hard endoscope 20 is drawn, and then a tissue protective tool 30 shown in FIG. 7A is attached to the side portion of the excising member 10 adjacent to the operator, which is positioned near the skin cut portion E1 in the inguinal region A. Then, while drawing, to the outside, the excising member 10 through the skin cut portion E2 above the knee D, the tissue protective tool 30 is introduced into the cavity G dissected by the excising member 10 so that a state shown in FIG. 2C is realized. Note that the tissue protective tool 30 can be inserted without a heavy load because the widthwise cross sectional area of the tissue protective tool 30 is substantially the same as the widthwise cross sectional area of the excising member 10. The tissue protective tool 30 is separated from the excising member 10 after the end portion of the excising member 10 adjacent to the operator's hand has been pulled out through the skin cut portion E2, the tissue protective tool 30 being then retained in the cavity G.

Then, a cavity forming tool (cavity expansion means) 50 shown in FIG. 11A is used to expand the cavity G. In the foregoing case, the cavity forming tool 50 is, as shown in FIG. 2D, introduced into the cavity G in a state where a projection 52 of the cavity forming tool 50 is received in a groove 30a in the upper surface of the tissue protective tool 30. The cavity forming tool 50 is introduced into the cavity G by means of a dilator hook 101 having a tapered leading end, the diameter of which is reduced toward the leading end, as shown in FIG. 10A. As shown in FIG. 11A, the cavity forming tool 50 is formed into a substantially rhombic shape having a flat leading end. A plurality of cavity forming tools, for example, 50a to 50d are prepared to serve as the cavity forming tool 50 respectively having various widths. When the cavity G is expanded by using the cavity forming tool 50, initially the dilator hook 101 is inserted to the skin cut portion E1 of the inguinal region A through the skin cut portion E2 above the knee D. Then, the cavity forming tool 50a having the smallest width is attached to the leading end of the dilator hook 101 protruding to the outside through the skin cut portion E1. Then, the operator holds the handle of the dilator hook 101 to pull the dilator hook 101 so that the cavity forming tool 50a is slowly introduced into the cavity G through the skin cut portion E1 in the inguinal region A while moving the projection 52 of the cavity forming tool 50a along the groove 30a of the tissue protective tool 30. Then, the cavity forming tool 50a is pulled out to the outside through the skin cut portion E2 above the knee D. Then, in a similar procedure, the cavity forming tools 50b to 50d, the widths of which are enlarged in this sequential order, are sequentially inserted and pulled out to and from the cavity G. As a result, the cavity G is expanded by stage. Note that the size of the cut portion of each of the skin cut portion E1 and skin cut portion E2 is determined to be the size which permits the cavity forming tool 50 having the largest width (for example, 50d) to be inserted.

After the foregoing operation has been completed, the cavity maintaining tool 60 is retained in the expanded cavity G so that the cavity G is maintained, as shown in FIG. 2E.

In the foregoing state, the blood vessel C is exposed into the cavity G maintained by the cavity maintaining tool 60. In this state, the hard endoscope 20 is inserted into a guide tube 62f of the cavity maintaining tool 60 to observe the overall body of the cavity G. Due to the observation above, the blood vessel C is completely exposed in a case where the excising member 10 has passed through a layer just above the blood vessel C. In a case where the excising member 10 passes through the blood vessel C through a membrane tissue, the upper portion of the blood vessel C is covered with the connective tissue 300 on the blood vessel C. Therefore, the connective tissue 300 on the blood vessel C is required to initially be removed in the foregoing case. The removal of the connective tissue 300 on the blood vessel C will be described later.

Then, the system for evulsing subcutaneous tissue according to this embodiment will now be described in detail.

FIG. 3 shows the hard endoscope 20. As shown in FIG. 3, the hard endoscope 20 comprises a hard insertion portion 2 including an observation optical system and an irradiation optical system; and an endoscope body 4 disposed at the base portion of the insertion portion 2 and having a connection portion 3 to be connected to the endoscope unit. An axial member 8 extends from the body 4. The insertion portion 2 has the leading end at which a leading end section 5 having an inclined type observation window inclined with respect to the axial line of the insertion portion 2 and an irradiation window is formed. The endoscope body 4 has a connector 7 which is connected to a light guide cable (not shown).

FIGS. 4A to 4G show the excising member 10. As shown in FIG. 4A, the excising member 10 comprises a body 11 formed into an elongated tube into which the hard endoscope 20 can be inserted; a large-diameter pipe 13 formed in the body 11 at a position adjacent to the operator's hand; and a transparent leading end 12 connected to the leading end of the body 11 and arranged to cover the leading end section 5 of the hard endoscope 20. The large-diameter pipe 13 has a slit 13a to which a tissue protective tool 30, to be described later, can be hooked.

As shown in FIGS. 4B to 4D, the leading end 12 is formed into a cylindrical cap made of a transparent synthetic resin and having a cross section which is completely closed as shown in FIGS. 4E to 4G. A ridge portion 16 between a slope 15a of the leading end 12 and an observation portion 15b is formed into a moderate shape to protect the blood vessel from being damaged. As a result of the performed investigation, the ridge portion 16 is required to be formed into a round shape having a curvature radius of at least 1 mm or larger, preferably 3 mm. If the curvature radius of the ridge portion 16 is too small, there arises a risk that the blood Vessel is cut unintentionally, in particular, the branch blood vessel is cut unintentionally.

The excising member 10 is arranged to satisfy $\phi A > \phi B$ assuming that the diameter of the leading end 12 is $\phi A$ and that of the body 11 is $\phi B$. The axial length of the leading end 12 is about 20 mm. As a result of the investigation, the structure that $\phi A$ is about 9 mm and $\phi B$ is about 6.5 mm enables the portion surrounding the blood vessel to efficiently be dissected while protecting the blood vessel from being damaged. The large-diameter pipe 13 is engaged to a sheath holder 110 shown in FIGS. 5A and 5B, the large-diameter pipe 13 having diameter $\phi C$ which is smaller than the diameter $\phi A$ of the leading end 12.

Figure 5A:
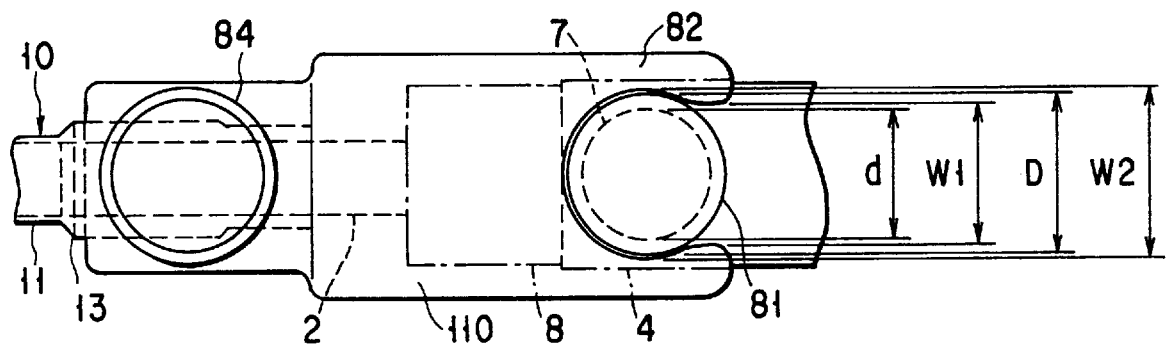
FIG. 5A is a plan view showing a sheath holder set to the endoscope together with the excising member.
Figure 5B:
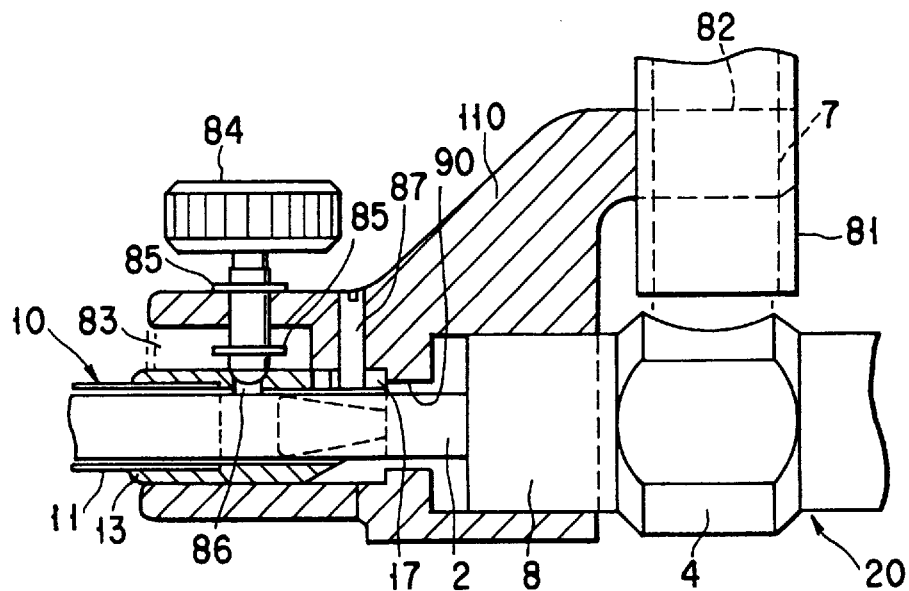
FIG. 5B is a vertical cross sectional view showing an assembly set into the state shown in FIG. 5A.

As shown in FIGS. 5A and 5B, the sheath holder 110 is slid along the outer surface of the insertion portion 2 of the hard endoscope 20 from the portion adjacent to the leading end of the insertion portion 2 so that the sheath holder 110 is attached to the endoscope body 4. A light connector 7 of the hard endoscope 20 has a cap adapter 81 at the mouth portion thereof so as to be connected to an arbitrary and conventional cable. In the foregoing case, the outer diameter of the connector 7 is set to diameter d, while the outer diameter of the cap adapter 81 is set to diameter D when connected to the connector 7 (see FIG. 5A). The sheath holder 110 has, in the base portion thereof, a joint 82. The joint 82 is formed into purse-like shape having an opened rear end and wide body portion. The diameter of the narrowest portion of the opened portion is set to diameter $W_1$. The maximum diameter of the wide body portion of the joint 82 is set to diameter $W_2$ so as to insert a cap adapter 81 therein. The diameters have a relationship expressed as $W_2 > D > W_1 > d$. That is, in the state where the cap adapter 81 has been attached to the connector 7, the sheath holder 110 cannot be attached to the endoscope body 4. In a state where the cap adapter 81 has been removed from the connector 7, the sheath holder 110 is attached to the endoscope body 4. Then, the cap adapter 81 is attached to the connector 7 so that the sheath holder 110 is fixedly attached to the endoscope body 4.

As shown in FIG. 5B, the sheath holder 110 has a joining port 83 at a position near the leading end thereof to receive the excising member 10. Moreover, a fixing screw 84 for fixing the excising member 10 is, together with a C-ring 85, disposed above the joining port 83. Thus, the leading end of the fixing screw 84 can be engaged to an engaging opening 86 formed in the large-diameter pipe 13 of the excising member 10. The sheath holder 110 has an opening in its portion which runs parallel to the portion in which the fixing screw 84 is inserted. A control pin 87 for controlling rotation of the excising member 10 is, from outside, inserted into the opening to project into a joining port 83. The projection portion of the control pin 87 projecting into the joining port 83 is received in a rotation-stopping groove 17 formed in the large-diameter pipe 13 of the excising member 10. As a result, when the excising member 10 is attached to the hard endoscope 20, the position of the excising member 10 in the rotational direction can automatically be determined. When the excising member 10 and the sheath holder 110 have been attached to the hard endoscope 20 as described above, as shown n FIG. 4B, the leading end section 5 of the hard endoscope 20 is placed to a position near the leading end of the leading end 12 of the excising member 10. In this state, observation by means of the hard endoscope 20 through the observation portion 15b is permitted in such a manner that the observation direction 0 of the hard endoscope 20 is diagonally downward. In this case, the slope 15a of the leading end 12 is directed to diagonally upward with respect to the axis of the insertion portion 2 of the hard endoscope 20.

Figure 6A:
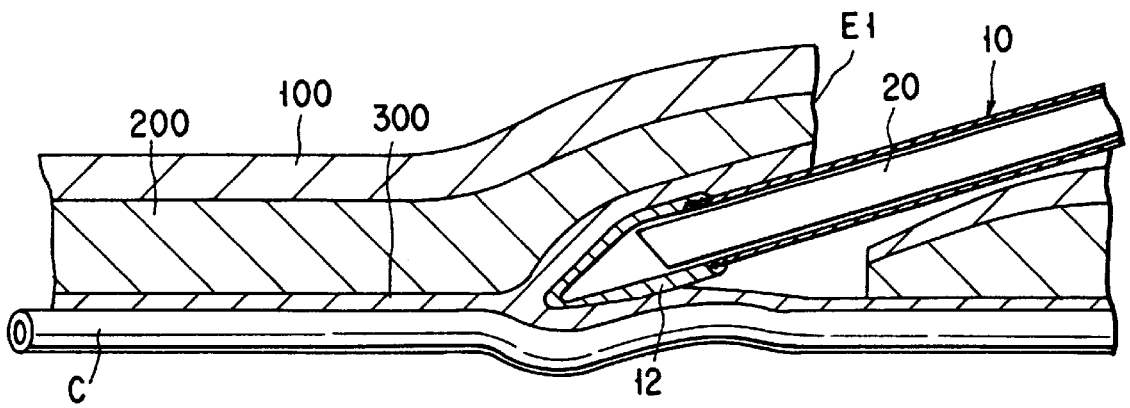
FIG. 6A is a vertical cross sectional view showing a state where an excising operation is performed with the excising member.
Figure 6B:
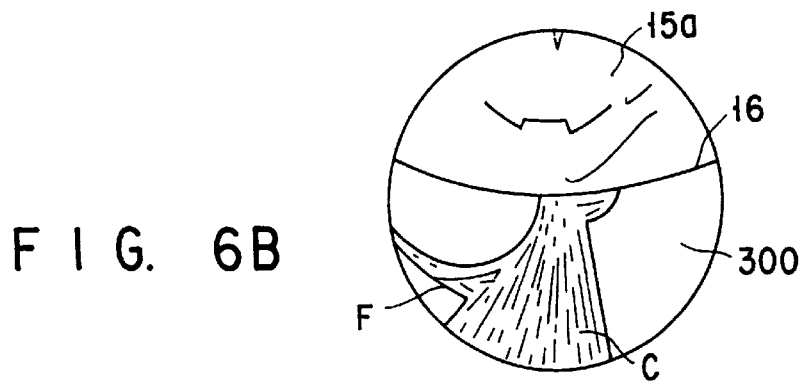
FIG. 6B shows an image observed with the endoscope in the operation state shown in FIG. 6A.

FIG. 6A shows a state where the excising member 10 has been attached to the hard endoscope 20 and inserted into the skin cut portion E1. The leading end 12 of the excising member 10 is, through the skin cut portion E1, inserted into the connective tissue 300 on the blood vessel C or the subcutaneous fat layer 200 near the blood vessel C and existing between the skin 100 and the blood vessel C. An image observed with the hard endoscope 20 is shown in FIG. 6B. As shown in FIG. 6B, the leading end 12 of the excising member 10 and the blood vessel C including the connective tissue 300 on the blood vessel C is included in the visual field of the hard endoscope 20 (symbol F represents a branch of blood vessel C). When the excising member 10 is moved forward in the foregoing state, the blood vessel C is dissected from the connective tissue 300 on the blood vessel C so that the blood vessel C is exposed. Also the branch F existing at an intermediate position of the blood vessel C is exposed. Thus, the blood vessel C and the branch F are included in the visual field of the hard endoscope 20. If the ridge portion 16 between the observation portion 15b and the slope 15a of the leading end 12 of the excising member 10 has an edge, the branch F can be cut unintentionally. However, the structure of this embodiment in which the ridge portion 16 is rounded to have a curvature radius of about 3 mm prevents the branch F from being cut. Since the diameter (φA) of the leading end 12 is a small diameter of about 9 mm, the blood vessel C and the branch F can be protected from being applied with an excessively heavy load when the excising member 10 is inserted along the blood vessel C. Therefore, the excising member 10 can safely be inserted into the subcutaneous portion. Thus, the blood vessel C and the connective tissue 300 on the blood vessel C can be dissected from each other while observing the blood vessel C with the hard endoscope 20.

After the excising member 10 has been inserted along the blood vessel C to cover the overall length of the evulsed region, the position of the leading end 12 of the excising member 10 is confirmed through the skin 100. The skin cut portion E2 is formed just above the leading end 12 of the excising member 10 so that the leading end 12 of the excising member 10 is projected through the skin cut portion E2. Then, the fixing screw 84 of the sheath holder 110 is loosened to remove the hard endoscope 20 from the excising member 10. Then, only the excising member 10 is retained in such a manner that the excising member 10 penetrates the portion from the skin cut portion E1 to the skin cut portion E2.

Figure 7B:
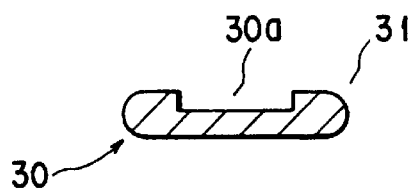
FIG. 7B is a cross sectional view taken along line 7B—7B shown in FIG. 7A.

The tissue protective tool 30 will now be described with reference to FIGS. 7A and 7B. As shown in FIG. 7A, the tissue protective tool 30 comprises an elongated protective tool body 31 formed into a plate-like shape which can be inserted into the subcutaneous tissue; and flanges 32 projecting at the base portion of the protective tool body 31 into the widthwise direction. The protective tool body 31 has a width capable of covering the subcutaneous tissue which is required to be protected. The length of the protective tool body 31 is made to be somewhat longer than that of each of the skin cut portion E1 and skin cut portion E2. The flanges 32 project to have the width with which the flanges 32 can not be inserted into the subcutaneous tissue through the skin cut portion E1. A protective surface of the protective tool body 31 for covering the subcutaneous tissue required to be protected, that is, the lower surface is formed into a smooth flat surface without any projections and pits. A surface opposite to the protective surface, that is, an upper surface has a groove 30a formed to cover the overall length of the upper surface in the axial direction of the protective tool body 31. In order to easily insert the tissue protective tool 30 into the subcutaneous tissue, the leading portion of the tissue protective tool 30 is tapered, the size of which is reduced in the forward direction. In order to protect the tissue from being damaged, the leading end of the protective tool body 31 is formed into a smooth and moderate shape.

FIGS. 8A and 8B show a method of connecting the tissue protective tool 30 and the excising member 10 to each other. The leading portion of the tissue protective tool 30 has a connection hole 31a which can detachably be hooked by the slit 13a of the excising member 10. In the case where the tissue protective tool 30 is used to cover and protect the subcutaneous tissue which is the subject of the protection, the connection hole 31a of the tissue protective tool 30 is connected to the slit 13a of the excising member 10 projecting over the skin cut portion E1. In this state, the leading end 12 of the excising member 10 projecting over the skin cut portion E2 is pulled to pull out the excising member 10 from the subcutaneous tissue. Moreover, the tissue protective tool 30 is pulled into the dissected cavity between the blood vessel C and the connective tissue 300 on the blood vessel C. By making the cross sectional area of the tissue protective tool 30 to be smaller than that of the excising member 10, the tissue protective tool 30 can easily be inserted between the blood vessel C and the connective tissue 300 on the blood vessel C. FIG. 9 shows a state where the tissue protective tool 30 has been, in place of the excising member 10, inserted between the blood vessel C and the connective tissue 300 on the blood vessel C, followed by being retained there. In the foregoing state, the excising member 10 has been removed from the tissue protective tool 30 and the blood vessel C is completely covered by the protective surface of the tissue protective tool 30, from an upper position.

Figure 10B:
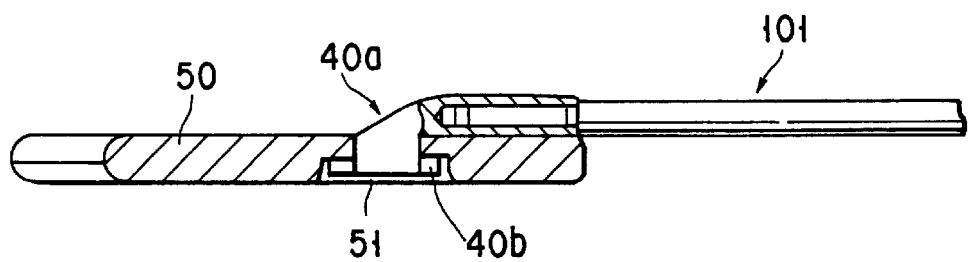
FIG. 10B is a vertical cross sectional view showing the connection portion in a state where the dilator hook has been connected to the cavity forming tool.
Figure 10C:
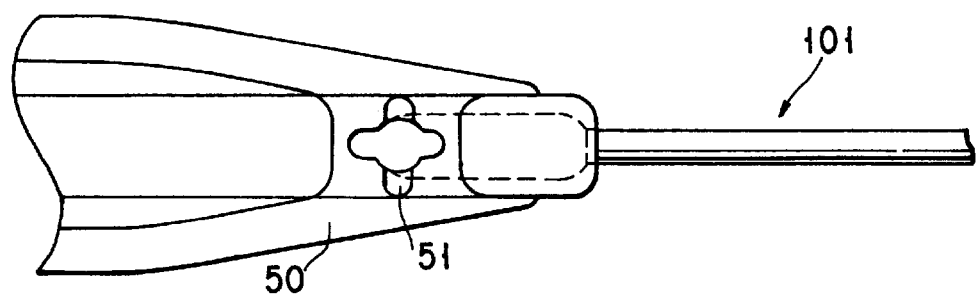
FIG. 10C is a plan view showing the connection portion in a state where the dilator hook has been connected to the cavity forming tool.
Figure 12:
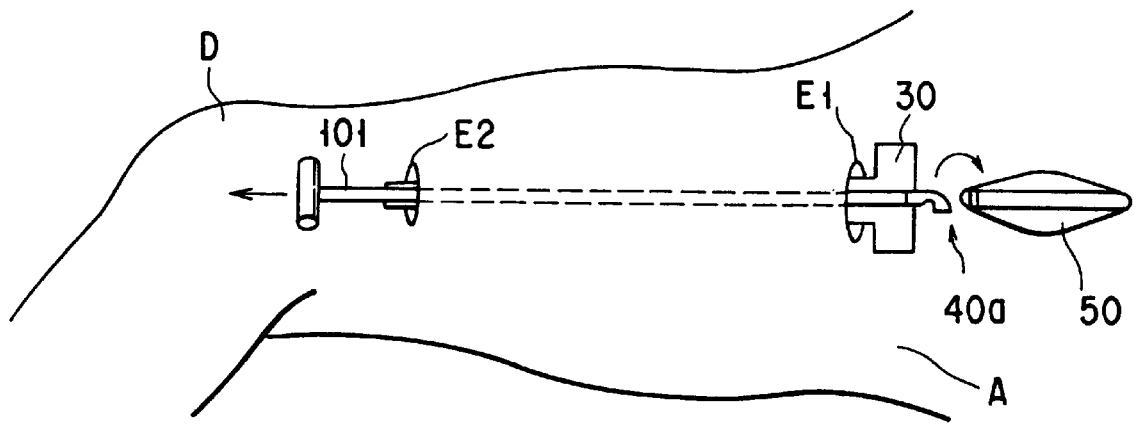
FIG. 12 is a perspective view showing a state where the cavity forming tool is connected to the tissue protective tool inserted between the skin cut portions.

FIGS. 10A to 10C show the dilator hook 101 for pulling the cavity forming tool 50 shown in FIG. 11A into the cavity G. The dilator hook 101 has a leading end 40a formed into a shape inclined towards the forward position. Therefore, when the dilator hook 101 is inserted into the subcutaneous tissue along the groove 30a of the tissue protective tool 30, the leading end 40a cannot be caught by the subcutaneous tissue. The leading end 40a of the dilator hook 101 has a hook 40b to be connected to the cavity forming tool 50. The cavity forming tool 50 has a connection hole 51 to be engaged to the hook 40b of the dilator hook 101. Note that the hook 40b and the connection hole 51 can be connected to each other in only a direction in which the longitudinal axial line of the cavity forming tool 50 has been rotated by an angular degree of about 90° with respect to the longitudinal axial line of the dilator hook 101. In a state where the dilator hook 101 is connected to the cavity forming tool 50 shown in FIGS. 10B and 10C, the dilator hook 101 is, along the groove 30a of the tissue protective tool 30, introduced into the cavity through the skin cut portion E2, as shown in FIG. 12. The leading end 40a is allowed to project through the skin cut portion E1. Then, the smallest cavity forming tool 50a is attached to the leading end leading end 40a of the dilator hook 101. Therefore, when the dilator hook 101 is pulled in the foregoing state, the cavity forming tool 50a is pulled into the dissected space between the blood vessel C and the connective tissue 300 on the blood vessel C. At this time, the cavity forming tool 50 is, as shown in FIG. 2D, pulled in such a manner that the projection 52 formed in the lower surface of the cavity forming tool 50 in the longitudinal direction of the same is guided by the groove 30a of the tissue protective tool 30. As a result, the dissected portion between the blood vessel C and the connective tissue 300 on the blood vessel C is expanded by the expansion portion 38 of the cavity forming tool 50a. Thus, a cavity wider than the cavity formed by the excising member 10 is formed above the blood vessel C, that is, above the tissue protective tool 30. After the minimum cavity forming tool 50a has reached the skin cut portion E2, the cavity forming tool 50a is removed from the dilator hook 101. Then, the cavity forming tool 50b having a second size is attached to the dilator hook 101, followed by being, similarly to the cavity forming tool 50a, inserted through the skin cut portion E1 to the skin cut portion E2. The foregoing operation is performed until the largest cavity forming tool 50d is inserted. After the largest cavity forming tool 50d has formed the cavity G having a predetermined size above the blood vessel C, the cavity G is maintained by a cavity maintaining tool 60 to be described below.

Figure 13:
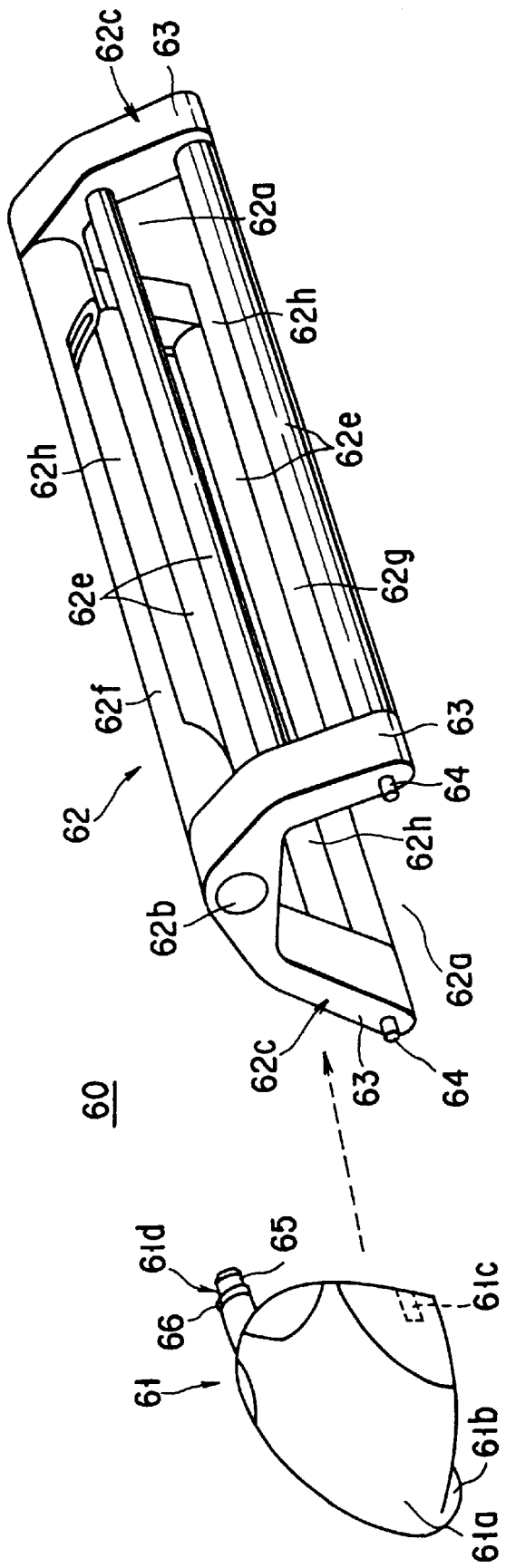
FIG. 13 is a perspective view showing the cavity maintaining tool.

FIG. 13 shows the cavity maintaining tool 60. The cavity maintaining tool 60 comprises an insertion helper 61 and a body 62 which can be exploded into individual parts. Note that the insertion helper 61 and the body 62 are made of a synthetic resin or stainless steel. Shafts 62e, by a number suitable to maintain the cavity, and an endoscope guide tube 62f for holding the endoscope are arranged between bases 62c of the body 62 of the cavity maintaining tool 60. The shafts 62e and the endoscope guide tube 62f are formed into a frame structure running parallel to the axial direction of the body 62. The bases 62c of the body 62 formed in the longitudinal direction are formed into the same arch forms each including openings 62a in the lower portion thereof for the purpose of smoothly inserting the treatment tool. The endoscope guide tube 62f is arranged on the rear portion of the central portion of the bases 62c, while the plural shafts 62e are arranged between legs 63 of the bases 62c. Since the shafts 62e and the endoscope guide tube 62f form a frame structure running parallel to the axial direction of the body 62, a plurality of large horizontal openings 62h are formed in the side portion of the body 62, the horizontal openings 62h being connected to a hollow portion 62g.

Pin-type locating members 64 for locating the insertion helper 61 project over the front wall in the lower portion of the two leg portions 63 of the front base 62c. The two end surfaces, the lower surface and the side surface in the longitudinal direction, which come in contact with the subcutaneous tissue to be protected, of the body 62 are rounded to remove edge portions. The endoscope guide tube 62f of the body 62 has two longitudinal ends which are formed into openings 62b. Moreover, an intermediate portion of the endoscope guide tube 62f is opened to face the hollow portion 62g on the inside of the body 62.

The insertion helper 61 is formed into a semi-conical shape having a rounded leading end. The lower surface of the insertion helper 61 is formed into a flat surface to have a hollow formed in the insertion helper 61. A leading portion 61a of the insertion helper 61 has a guide convex portion 61b so as to be guided to the subject tissue. The guide convex portion 61b is allowed to slightly project over the lower surface of the insertion helper 61. When the cavity maintaining tool 60 is retained in the subject subcutaneous tissue, the guide convex portion 61b is received in the groove 30a of the tissue protective tool 30, which has been inserted. The leading end portion 61a of the insertion helper 61 is received in the groove 30a of the tissue protective tool 30 when combined with the tissue protective tool 30. The insertion helper 61 has locating holes 61c in the lower portion of the trailing end thereof, the locating holes 61c being arranged to receive the locating members 64 of the body 62. The insertion helper 61 has an elastic member 61d in the upper portion of the trailing end thereof, the elastic member 61d being arranged to serve as a connection member to be engaged and secured to the body 62. The elastic member 61d consists of a projection 65 and an O-ring 66 attached around the projection 65. The elastic member 61d is inserted and fastened in the opening of a front opening 62b of the endoscope guide tube 62f so as to secure the insertion helper 61 and the body 62. The front opening 62b of the endoscope guide tube 62f has a groove shape to satisfactorily receive the elastic member 61d in the form of a projection.

As described above, the cavity maintaining tool 60 is structured such that the locating members 64 of the body 62 are received by the locating holes 61c of the insertion helper 61 so as to be engaged to the locating holes 61c. Moreover, the elastic member 61d of the insertion helper 61 is inserted and engaged to the front opening 62b of the endoscope guide tube 62f of the body 62. Thus, the body 62 and the insertion helper 61 are combined to each other. As a result of the foregoing structure, the insertion helper 61 can easily be removed from the body 62 while requiring a single action.

The cavity maintaining tool 60 having the foregoing structure is, along the groove 30a of the tissue protective tool 30, inserted into the cavity formed by the cavity forming tool 50 through the skin cut portion E1. At this time, the cavity maintaining tool 60 can smoothly be inserted into the cavity because the cavity formed by the cavity forming tool 50 is larger than the cross sectional area of the cavity maintaining tool 60 and the insertion helper 61 is tapered forwards. The cavity maintaining tool 60 is inserted until the insertion helper 61 of the cavity maintaining tool 60 projects through the skin cut portion E2. After the insertion helper 61 has projected through the skin cut portion E2, the insertion helper 61 is removed from the body 62.

Figure 14A:
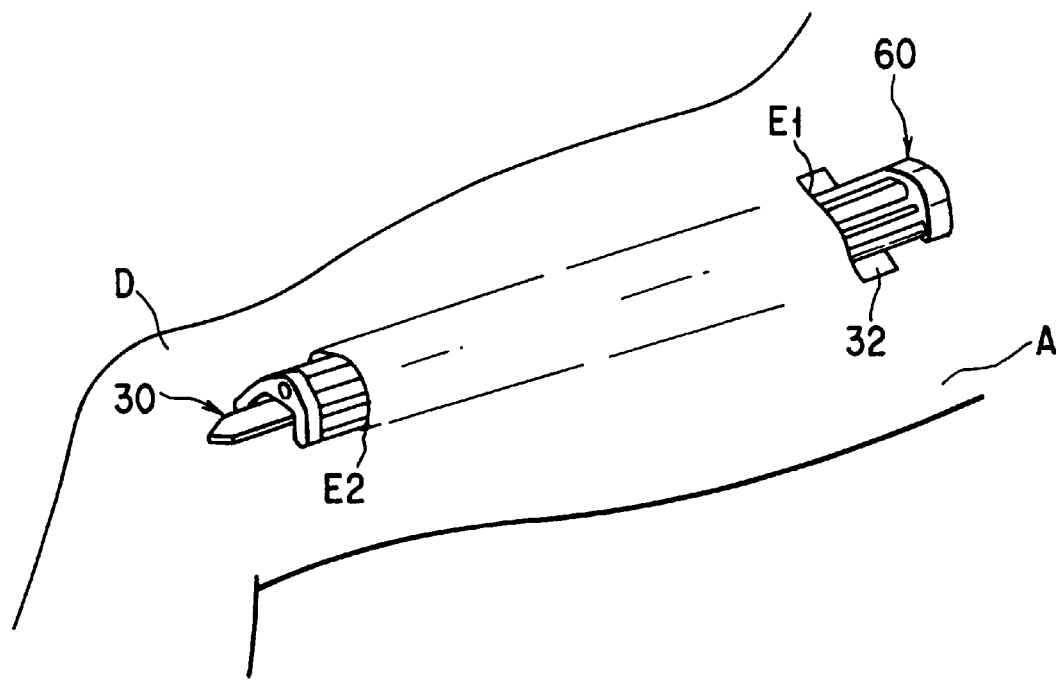
FIG. 14A is a diagram showing a state where the tissue protective tool and the cavity maintaining tool have been inserted into the subcutaneous tissue.
Figure 14B:
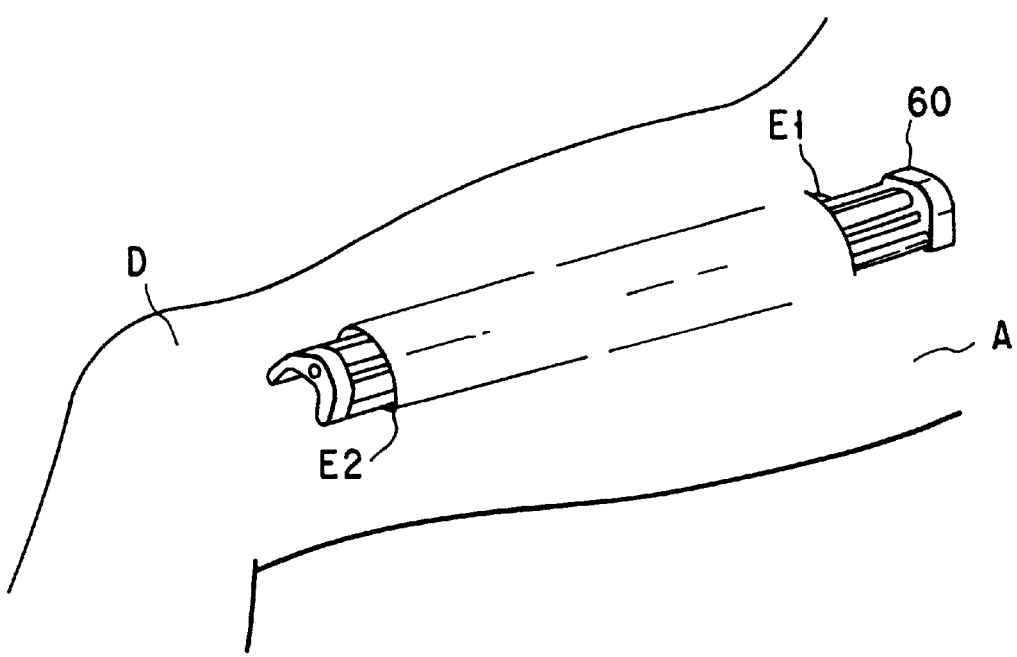
FIG. 14B is a diagram showing a state where the cavity maintaining tool has been inserted into the subcutaneous tissue.

FIG. 14A shows a state where the cavity maintaining tool 60 has been inserted and retained in the cavity. In the foregoing state where the cavity maintaining tool 60 is retained in the cavity, the tissue protective tool 30 is slowly pulled out through the skin cut portion E1. The foregoing state is shown in FIG. 14B. In the state shown in FIG. 14B, the two ends of the cavity maintaining tool 60 project through the skin cut portion E1 and skin cut portion E2. Thus, the cavity G is maintained just above the blood vessel C, which is the saphenous vein.

Figure 15A:
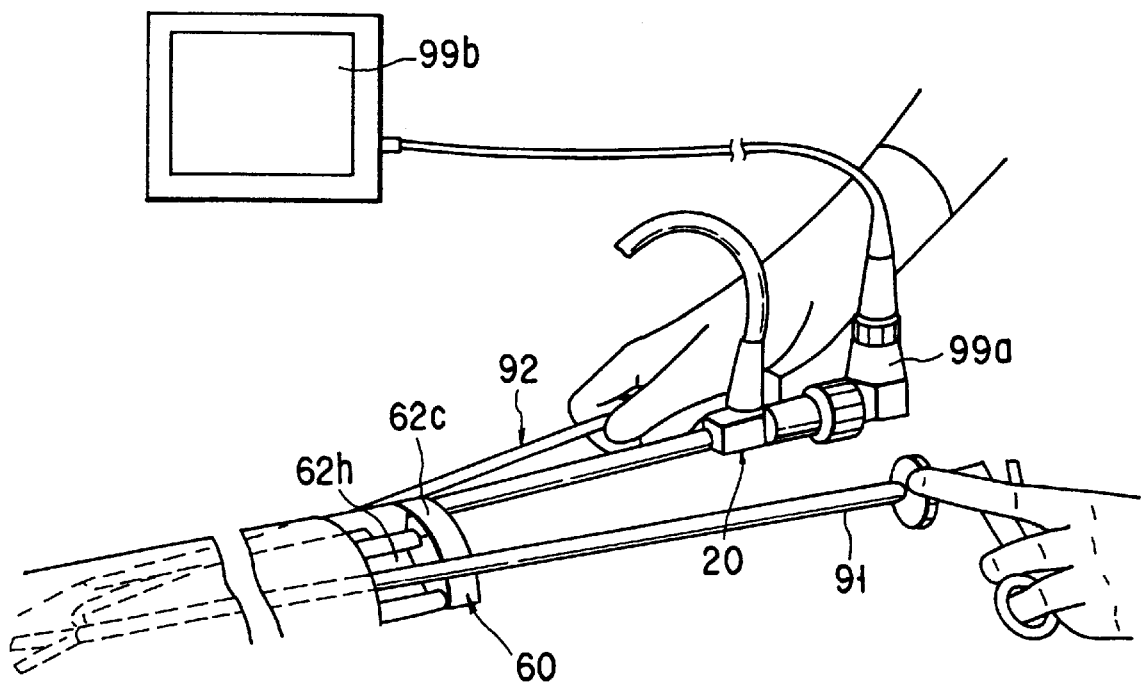
FIG. 15A is a perspective view showing a state where the hard endoscope and a treatment tool have been inserted into the cavity maintaining tool.
Figure 15B:
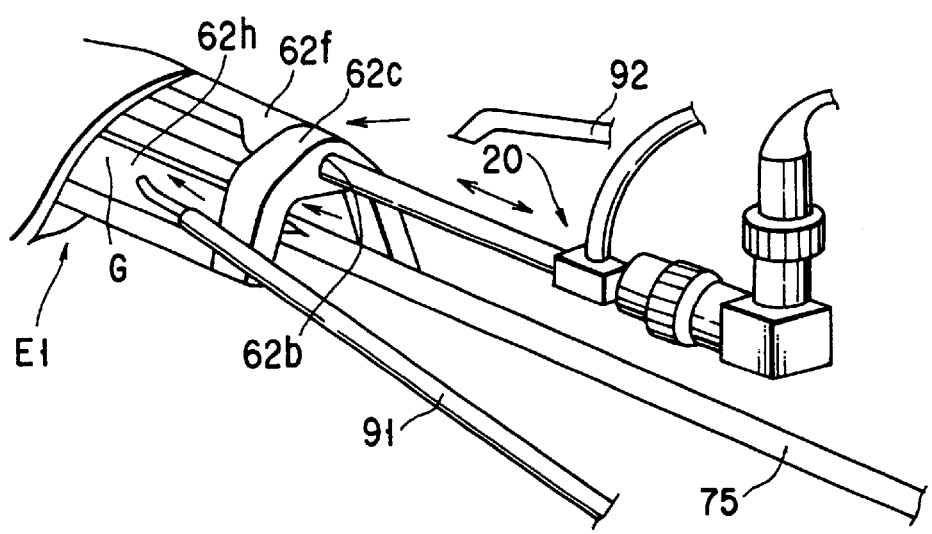
FIG. 15B is a perspective view showing a state where the hard endoscope and the treatment tool have been inserted into the cavity maintaining tool.

In the state shown in FIG. 14B, the hard endoscope 20 is inserted into the cavity G through the opening 62b of the rear bases 62c of the cavity maintaining tool 60, as shown in FIG. 15A and 15B. An endoscope TV camera 99a is connected to the hard endoscope 20 so that an image picked up by the hard endoscope 20 is displayed on a monitor 99b. As a result, the operator is enabled to easily observe the overall region to be treated by sliding the hard endoscope 20. On the other hand, a treatment tool, for example, forceps 91 are inserted into the cavity G through the horizontal openings 62h formed on either side of the cavity maintaining tool 60. Moreover, for example, a hook probe 92 is inserted into the cavity G through the horizontal openings 62h formed on another side surface of the cavity maintaining tool 60.

Figure 16:
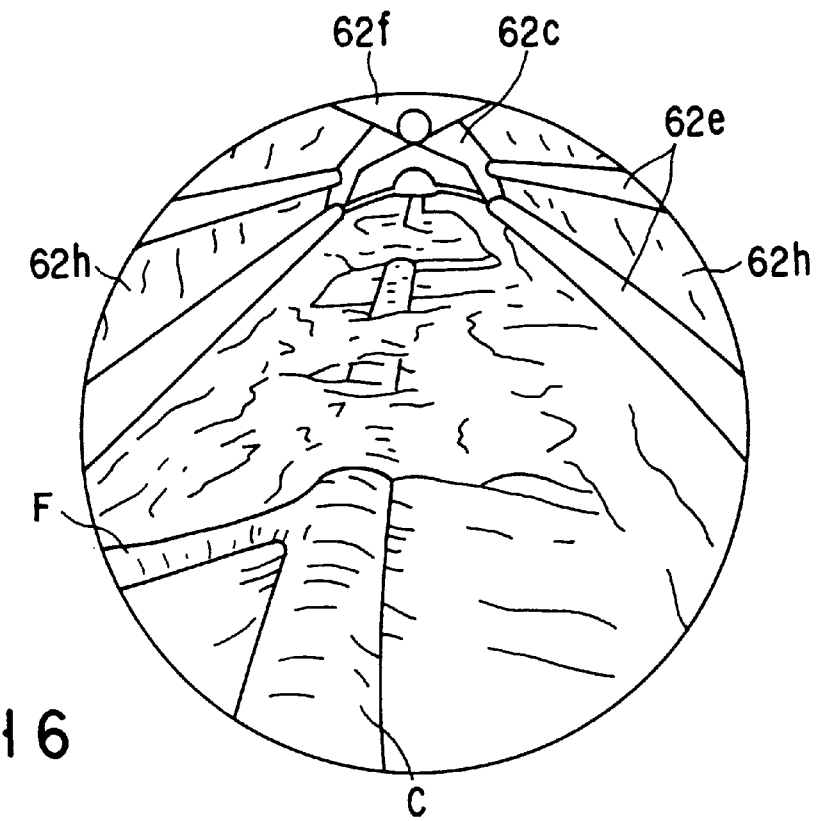
FIG. 16 shows an image observed with the hard endoscope.
Figure 17:
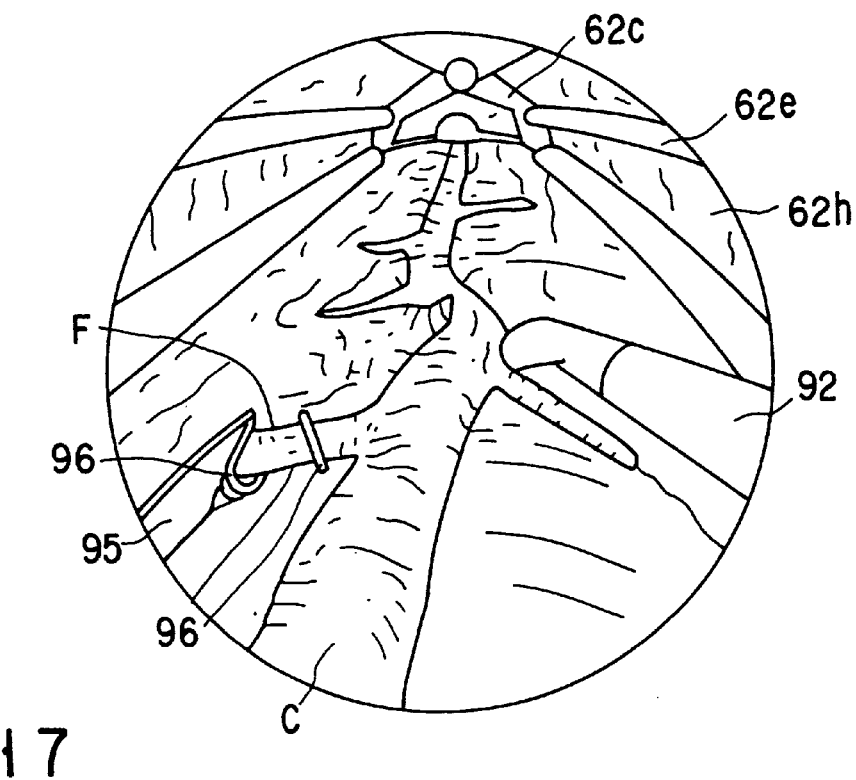
FIG. 17 shows an image observed with the hard endoscope.

As described above, the cavity maintaining tool 60 enables the hard endoscope 20, the forceps 91 and the hook probe 92 to be simultaneously inserted through the rear end of the cavity maintaining tool 60. Therefore, the operator is enabled to dissect the connective tissue 300 on the blood vessel C from the blood vessel C by the hook probe 92 and cut the connective tissue 300 on the blood vessel C with the forceps 91 to separate the connective tissue 300 on the blood vessel C from the blood vessel C while observing the cavity G with the hard endoscope 20. The states of the excising operation and the cutting operations are shown in FIGS. 16 to 19B. FIG. 16 shows an image in the cavity G picked up by the hard endoscope 20. As shown in FIG. 16, the shafts 62e, horizontal openings 62h and bases 62c of the cavity maintaining tool 60, the blood vessel C and the branch F extending into the lateral direction can be observed. FIG. 17 shows a state where a clip 96 is deformed by a clip applier 95 inserted into the cavity G through the horizontal opening 62h and serving as a treatment tool and an intermediate portion of the branch F is held by the clip 96. FIG. 18 shows a state just before an intermediate portion of the branch F between the two clips 96 is cut by the forceps and a state after the same has been cut. The foregoing operations are performed in a portion from the skin cut portion E1 to the skin cut portion E2. After the blood vessel C has been completely separated from the surrounding tissue as a result of the foregoing operation, the blood vessel C is cut at the positions of the skin cut portion E1 and skin cut portion E2 so as to be evulsed from the inside portion of the cavity G. As a result, evulsion of the blood vessel C having a length of, for example, about 25 cm is completed.

If a longer blood vessel is required to be evulsed, a similar operation is performed through the skin cut portion E2 toward the knee. Thus, blood vessel C having a length of 50 cm to 60 cm extending from the skin cut portion E2 toward the inguinal region and the ankle can be evulsed at a time.

FIGS. 19A and 19B show images picked up by the hard endoscope 20 to illustrate the states where the hook probe 92 is used. FIG. 19A shows a state where the hook probe 92 has been inserted through a right-hand portion of the horizontal openings 62h of the cavity maintaining tool 60 and approached from the right portion by a first hook 92a of the hook probe 92. FIG. 19B shows a state where the hook probe 92 has been inserted through a left-hand portion of the horizontal openings 62h of the cavity maintaining tool 60 and approached from the left portion by a second hook 92a of the hook probe 92. Both of FIGS. 19A and 19B show the state where intermediate portions of the blood vessel C are hooked by the first and second hooks 92a and 92b and, thus, the blood vessel C has been raised. In the foregoing operation, the connective tissue 300 on the blood vessel C is cut by the forceps while being dissected from the blood vessel C so as to be separated from the blood vessel C by cutting. In the foregoing operation, the hard endoscope 20 is placed substantially on the upper surface of the cavity maintaining tool 60 so that each treatment tool is inserted through the right and left horizontal openings 62h with respect to the hard endoscope 20. If the hook probe 92 is, in this case, used to dissect the blood vessel C, the insertion operation can smoothly be performed by causing the right hand to hold the hook probe 92 to insert the hook probe 92 through the right horizontal openings 62h in the case where the operator is a right-handed person. In this case, the second hook 92b warped to the right does not hinder the visual field of the hard endoscope 20, thus resulting in a satisfactory effect. If another treatment tool is used, it is preferable that the left hand has the hook probe 92 and the right hand has the treatment tool. In this case, use of the second hook 92c warped to the left results in a satisfactory effect being obtained because the visual field of the hard endoscope 20 is not hindered.

As described above, according to the first embodiment, the blood vessel can be evulsed while protecting the blood vessel from being damaged and without a necessity of greatly incising the skin. Thus, a risk of a complication occurring after the operation can be eliminated and a satisfactory advantage can be realized in terms of improving cosmetic effect.

Among conventional methods of extracting a blood vessel, a method is available which is adaptable to extracting the subcutaneous blood vessel, such as the saphenous vein in the lower extremity, and which comprises the steps of incising the skin along the blood vessel below the skin by using a knife or the like; further incising the panniculus adiposus and the connective tissue on the blood vessel which is the lower layers of the skin to expose the blood vessel having a length intended to be extracted; and cutting the two ends of the exposed blood vessel to extract the same to the outside of the body.

However, since the extracting method of the foregoing type inevitably greatly incises the skin, a too long time is required for the patient to be cured. What is worse, the incised portion is scarred and hardened, thus causing a problem to arise in that the patient has a cramp in the leg when moves the leg and thus the patient feels a pain.

Accordingly, an attempt has been, as disclosed in Japanese Patent Publication No. 4-10328, made such that a portion of the skin is cut by a knife or the like; an endoscope guide tube is inserted into the subcutaneous tissue; and the treatment is performed while observing the subject portion with the endoscope.

When treatment is performed while observing the subject portion with the endoscope, the hook probe 92 according to the foregoing embodiment is suitable to perform the operation. Hitherto, a hook-type probe having a structure as disclosed in U.S. Pat. No. 5,318,582, U.S. Pat. No. 5,346,503 and U.S. Pat. No. 5,356,419 has been employed. The hook type probe has a hook disposed at an end of a shaft thereof, and a handle is provided for another end of the shaft. Thus, tissue can be hooked by the hook at the leading end of the shaft by the operator who holds the handle to remove the tissue and a portion of the tissue can be removed by cutting.

However, the conventional hook-type prove has been arranged to selectively use a variety of probes which are different from one another in only the shapes of the hooks to be attached to the end of the shaft to be adaptable to the situation. Therefore, the probes are required to be sent and received to and from the operator whenever the state of the portion to be treated is changed, thus resulting in a long time being required to complete the operation.

In an example case where the blood vessel is dissected from the surrounding tissue, a method has been generally employed in which holding forceps are used to pick up the surrounding tissue so as to be cut by cutting forceps. However, the foregoing method requires a complicated operation and results in a long time being required to complete the operation.

Accordingly, a hook probe will now be described with which the operations for passing the tool can be decreased and the time required to complete the operation can be shortened.

Figure 20:
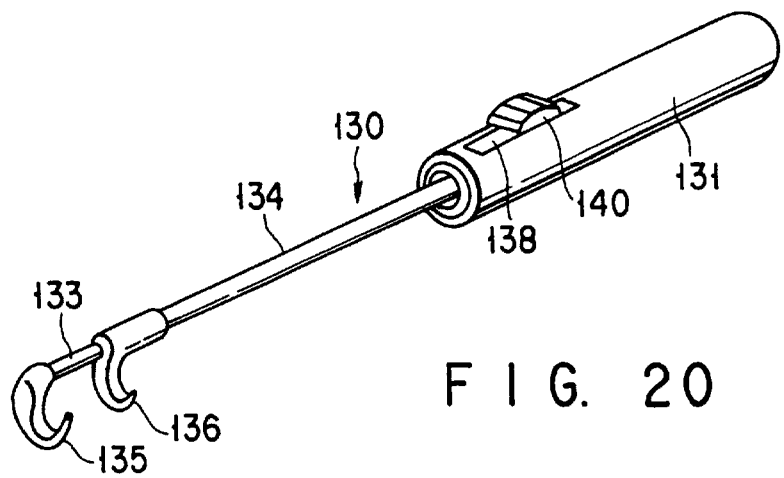
FIG. 20 is a perspective view showing a first example of the hook probe.
Figure 21:
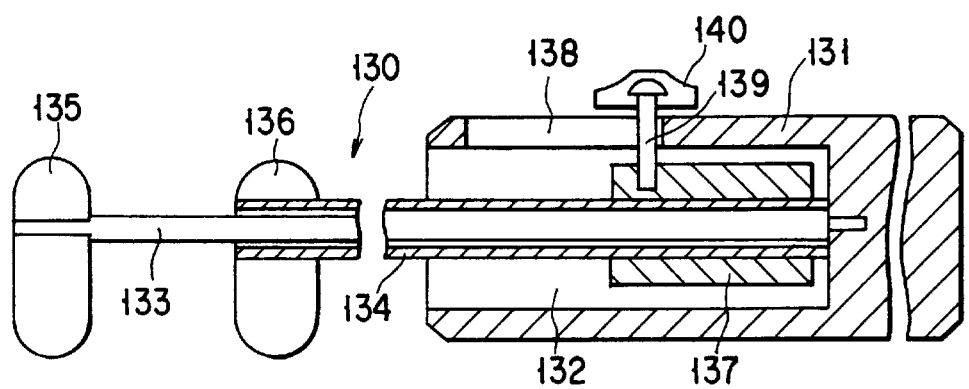
FIG. 21 a vertical cross sectional view showing the hook probe shown in FIG. 20.

FIGS. 20 to 22B show a first example of the hook probe. As shown in FIGS. 20 and 21, a hook probe 130 has an operation portion 131. The operation portion 131 has an internal cavity 132 opened in the leading end portion of the operation portion 131. A shaft 133 is disposed in the central portion of the internal cavity 132, the shaft 133 having the base secured to the operation portion 131 and a leading end which projects forwards over the internal cavity 132. A pipe 134 capable of moving the axial direction is connected to the shaft 133. The shaft 133 has the leading end to which the first hook 135 is secured, while a second hook 136 is secured to the leading end of the pipe 134. The first and second hooks 135 and 136 basically have the same shape each of which warped into a C-shape to project toward the side portions of the shaft 133 and the pipe 134. A fixing member 137 disposed in the internal cavity 132 of the operation portion 131 is attached to the base portion of the pipe 134. A pin 193 penetrating an elongated hole 138, formed in the operation portion 131, projecting outwardly is disposed on the fixing member 137. A operation button 140 is provided for the leading end of the pin 139. Therefore, when the operator move forwards and rearwards the operation button 140 while holding the operation portion 131, the pipe 134 is moved forwards or rearwards so that the first and second hooks 135 and 136 are opened and closed.

Figure 22A:
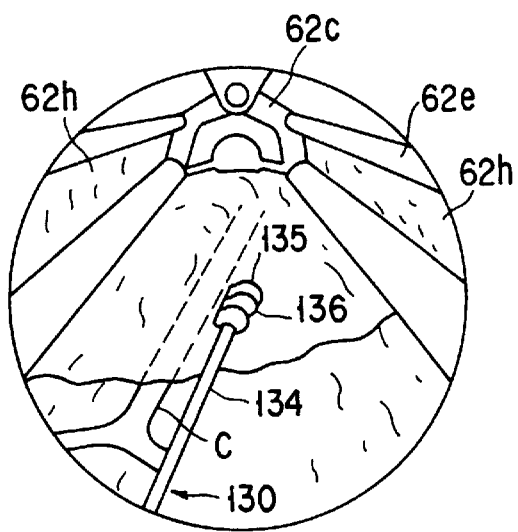
FIG. 22A shows an image observed with the endoscope to illustrate a state where the hook probe shown in FIG. 20 is used.
Figure 22B:
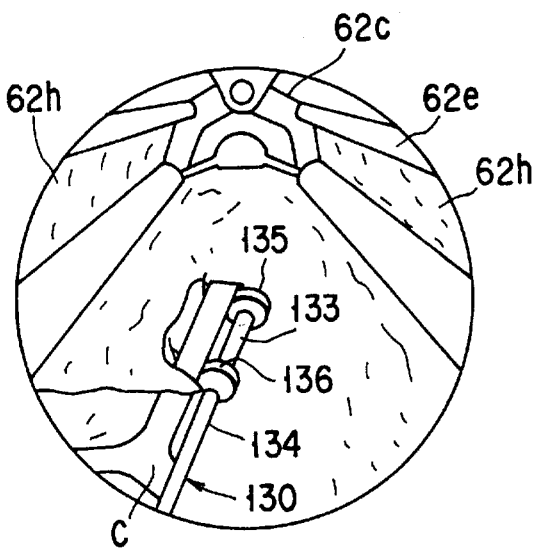
FIG. 22B shows an image observed with the endoscope to illustrate a state where the hook probe shown in FIG. 20 is used.

As can be understood from the images shown in FIGS. 22A and 22B and picked up by the hard endoscope 20, the opening/closing type hook probe 130 is inserted into the cavity G in a state where the first and second hooks 135 and 136 are closed to approach the connective tissue 300 on the blood vessel C. Then, the first and second hooks 135 and 136 are introduced into the portion below the blood vessel C, followed by opening the first and second hooks 135 and 136. Thus, the hook probe 130 is able to tear the connective tissue 300 on the blood vessel C so as to expose the blood vessel C.

As described above, the hook probe 130 enables the operation for excising the blood vessel from the surrounding tissue to be performed in a short time without using a plurality of treatment tools by using only the opening/closing hook probe 130. Although the first example has the structure such that the first hook 135 is fixed and the second hook 136 is made to be movable, a contrary structure may be employed. A structure may be employed in which both of the first and second hooks 135 and 136 are movable. If the outer edges of the first and second hooks 135 and 136 are sharpened, the tissue can easily be cut and opened by the first and second hooks 135 and 136 when the first and second hooks 135 and 136 have been moved into a direction in which they are moved apart from each other (see FIG. 22B).

FIGS. 23A and 23B show a second example of the hook probe. As shown in FIG. 23A, the opening/closing type hook probe 141 according to this example is composed of an operation portion 142, a shaft portion 143 provided for the operation portion 142 and a hook portion 144 formed at the leading end of the shaft portion 143. The operation portion 142 comprises a cylindrical member 147. The cylindrical member 147 has, at the leading end thereof, an opened portion 145 and, at a trailing end thereof, a closed portion 146. The cylindrical member 147 has a side wall in which an elongated hole 148 is formed, the elongated hole 148 being formed in the direction of the longitudinal axis of the cylindrical member 147. The closed portion 146 has a male thread portion 149 on the outer surface thereof and, the closed portion 146 further comprising a female thread portion 150 formed in the axial center portion thereof. A fixing member 152 having a slot 151 is screwed in the female thread portion 150. The outer surface of the base portion of the fixing member 152 is tapered. The fixing member 152 has a hole in the central portion thereof, the hole penetrating the fixing member 152 in the axial direction of the same. The diameter of the hole is reduced at the base end portion of the tapered fixing member 152 so that a stepped portion 153 is formed.

A cap 154 is screwed into the male thread portion 149 of the closed portion 146. A tapered hole 155, to which the base portion of the fixing member 152 is received, is formed in the inner portion of the cap 154. A slider 156 having a through hole 156a formed in the axial direction thereof is inserted into the cylindrical member 147 so as to be movable in the axial direction of the cylindrical member 147. The slider 156 is secured to an operation button 157 which is able to slide in the axial direction of the cylindrical member 147 while being guided by the elongated hole 148. The cylindrical member 147 includes a coil spring 158 at a position between the slider 156 and the closed portion 146. The urging force of the coil spring 158 urges the slider 156 toward the leading end of the cylindrical member 147.

The shaft portion 143 comprises a shaft 160 and a pipe 161 attached on the outside of the shaft 160 so as to be slidable in the axial direction thereof. The shaft 160 has the base portion which penetrates a through hole 156a of the slider 156 and which is secured to the fixing member 152. The base portion of the pipe 161 is secured to the slider 156. Therefore, when the slider 156 is longitudinal moved, the pipe 161 is moved forwards or rearwards.

The hook portion 144 consists of a first hook 162 and a second hook 163. The base portion of the first hook 162 is secured to the leading end of the shaft 160. The base portion of the second hook 163 is secured to the base portion of the pipe 161. As shown in FIG. 23B, the first hook 162 is formed into a semi-circular arc shape and has a sharp portion 162a having a sharp leading end. Similarly to the fixing member 152, the stepped portion 153 is formed into a semicircular arc shape and having a sharp portion 163a having a sharp leading end. The first and second hooks 162 and 163 are projection and pit portions 164 at the base portions thereof so as to be engaged mutually.

As a result of the foregoing structure, when the operator touches the operation button 157 of the operation portion 142 with the finger to rearwards move the operation button 157 against the urging force of the coil spring 158 as indicated by an alternate long and two short dashes line, the slider 156 is pulled into the inner portion of the cylindrical member 147. When the rearward movement of the slider 156, the second hook 163 is moved rearwards and apart from the first hook 162. As a result, the hook portion 144 is opened. When the operator releases the finger in the foregoing state, the slider 156 is moved forwards due to the urging force of the coil spring 158 so that the second hook 163 is brought into contact with the first hook 162 through the pipe 161.

As described above, the hook probe 141 according to this example is initially inserted into the cavity G in the state where the first and second hooks 162 and 163 are opened to be allowed to approach the connective tissue 300 on the blood vessel C. Then, with the hook probe 130, the first and second hooks 135 and 136 are introduced into the portion below the blood vessel C, followed by opening the first and second hooks 135 and 136 so that the connective tissue 300 on the blood vessel C is torn.

As described above, the hook probe 141 enables the operation for excising the blood vessel from the surrounding tissue to be performed in a short time without using a plurality of treatment tools by using only the opening/closing hook probe 141. Although the second example has the structure such that the first hook 162 is fixed and the second hook 163 is made to be movable, a contrary structure may be employed. A structure may be employed in which both of the first and second hooks 162 and 163 are movable. If the outer edges of the first and second hooks 162 and 163 are sharpened, the tissue can easily be cut and opened by the first and second hooks 162 and 163 when the first and second hooks 162 and 163 have been moved into a direction in which they are moved apart from each other.

The opening/closing type hook probe 141 according to this example can be assembled by a user. The assembling operation is performed such that the shaft 160 having the first hook 162 is, from the position adjacent to the second hook 163, inserted into the pipe 161 having the second hook 163. Then, the shaft 160 and the pipe 161 are inserted into the operation portion 142 in a state where the projection and pit portions 164 of the first and second hooks 162 and 163 are aligned to each other. At this time, the coil spring 158 is held between the slider 156 and the closed portion 146, and the shaft portion of the operation button 157 is guided by the elongated hole 148. Then, the base portion of the shaft 160 is allowed to abut against the stepped portion 153 of the fixing member 152. Then, the cap 154 is screwed in the male thread portion 149 of the cylindrical member 147 so that the tapered hole 155 is allowed to abut against the tapered portion of the base portion of the fixing member 152 so that the shaft 160 is clamped and secured.

Since the opening/closing type hook probe 141 can be decomposed as described above, the hook probe 141 can easily be decomposed so as to be washed. Since the projection and pit portions 164 are provided for the first and second hooks 162 and 163 and the abutting stepped portion 153 is provided for the fixing member 152 of the shaft 160, the assembling operation can be performed in the state where the leading ends of the first and second hooks 162 and 163 are aligned to each other. Therefore, the assembling operation can be facilitated. Since the coil spring 158 is attached, the hook portion 144 is closed in a usual state. Thus, the tissue of the organism can be protected from being damaged intentionally by a sharp portion of the nail and the treatment can be performed safely.

FIGS. 24A and 24B show a third example of the hook probe. A hook probe 170 according to this example has the basic structure which is the same as that according to the second example. However, a difference lies from the second example in the coil spring 158 being omitted. As a result of the foregoing structure, no load acts when the hook portion 144 is opened and closed. Thus, the operator is enabled to delicately open/close the hook portion 144. Since the parts to be exploded at the decomposition can be decreased, the assembling operation and washing operation can easily be performed.

Figure 25A:
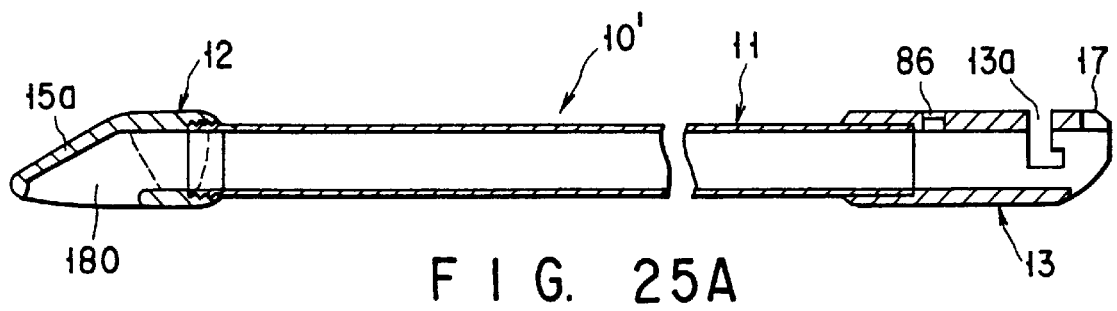
FIG. 25A is a vertical cross sectional view showing a first modification of the excising member shown in FIGS. 4A to 4G.
Figure 25B:
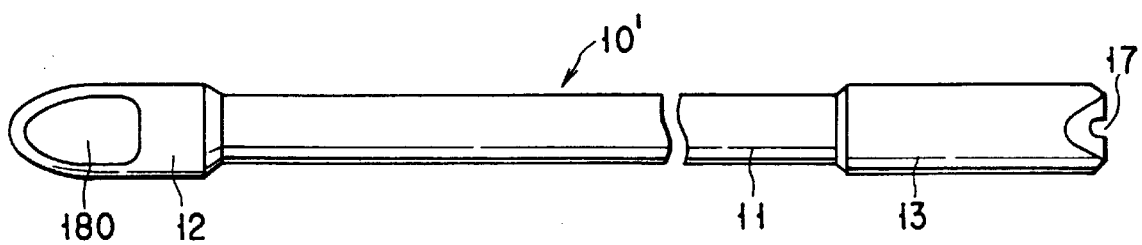
FIG. 25B is a plan view showing the excising member shown in FIG. 25A.
Figure 26A:
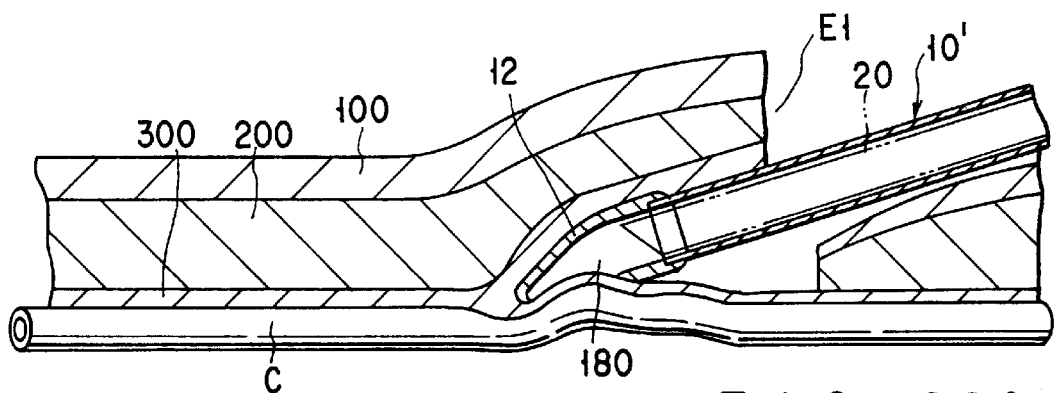
FIG. 26A is a vertical cross sectional view showing a state where an excising operation is performed with the excising member shown in FIG. 25A.
Figure 26B:
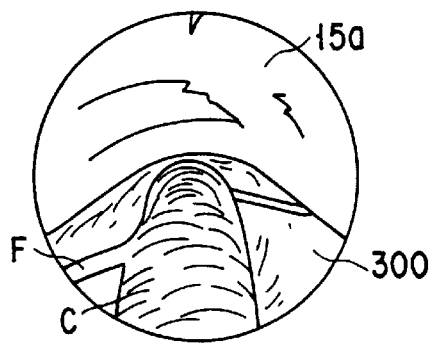
FIG. 26B shows an image observed with the endoscope in the operation state shown in FIG. 26A.

FIGS. 25A and 25B show a first modification of the excising member 10 shown in FIGS. 4A to 4G. The same elements as those of the excising member 10 are given the same reference numerals and they are omitted from description. As shown in FIGS. 25A and 25B, the excising member 10' according to this modification has, at the leading end 12 thereof, an opening 180 permitting observation to be performed with the hard endoscope 20. FIG. 26A shows a state where the excising member 10', to which the hard endoscope 20 has been attached, has been inserted below the skin through the skin cut portion E1. An image picked up by the hard endoscope 20 in the foregoing state of insertion is shown in FIG. 26B.

FIGS. 27A and 27B show a first modification of the tissue protective tool 30 shown in FIG. 7A. As shown in FIG. 7A, a protective tool body 31' of a tissue protective tool 30' according to this modification has a cross sectional shape as shown in FIG. 27B so that the groove 30a is formed by the outer surface of the protective tool body 31'. Since the residual structures are the same as those of the tissue protective tool 30, the same elements are given the same reference numerals and they are omitted from description.

FIGS. 28A to 28C show a second modification of the tissue protective tool 30 and a first modification of the cavity forming tool 50. A tissue protective tool 190 according to this modification comprises a protective tool body 190a, which is a plate-like elongated member so as to be inserted into the subcutaneous tissue; and a flange portion 190b projecting at the base portion of the protective tool body 190a in the widthwise direction. Elongated grooves 191 are formed in the right and left side surfaces of the protective tool body 190a, the elongated grooves 191 being formed in the lengthwise direction of the protective tool body 190a (see FIG. 28C). A connection hole 31a is formed in the leading end portion of the protective tool body 190a, the connection hole 31a being arranged to be caught by the slit 13a of the excising member 10 shown in FIGS. 4A to 4G so as to be detachably connected. The protective tool body 190a has a width capable of covering and protecting the subcutaneous blood vessel to be protected and a length which is somewhat longer than the distance between the skin cut portion E1 and the skin cut portion E2. The flange portion 190b projects to have a width with which the insertion into the subcutaneous tissue through the skin cut portion E1 is inhibited. In order to smoothly insert the tissue protective tool 190 into the subcutaneous tissue, the leading end of the tissue protective tool 190 is tapered in the forward direction. In order to protect the tissue from being damaged, the leading end portion of the tissue protective tool 190 is formed into a smooth and moderate shape. On the other hand, to enable the cavity forming tool 50' to be guided along the tissue protective tool 30 when the cavity forming tool 50' is inserted into the subcutaneous tissue, engaging groove 192 capable of engaging to the elongated grooves 191 of the tissue protective tool 190 is formed in the lower surface of the cavity forming tool 50' (see FIG. 28B). The connection hole 51 to be engaged to the hook 40b of the dilator hook 101 shown in FIG. 10A is formed in the leading end of the cavity forming tool 50'.

As a result of the foregoing structure, the engagement between the elongated grooves 191 and the engaging groove 192 permits the cavity forming tool 50' to be relatively moved with respect to the tissue protective tool 30 in the engaged state so that the cavity forming tool 50' is reliably guided by the tissue protective tool 30.

Figure 29:
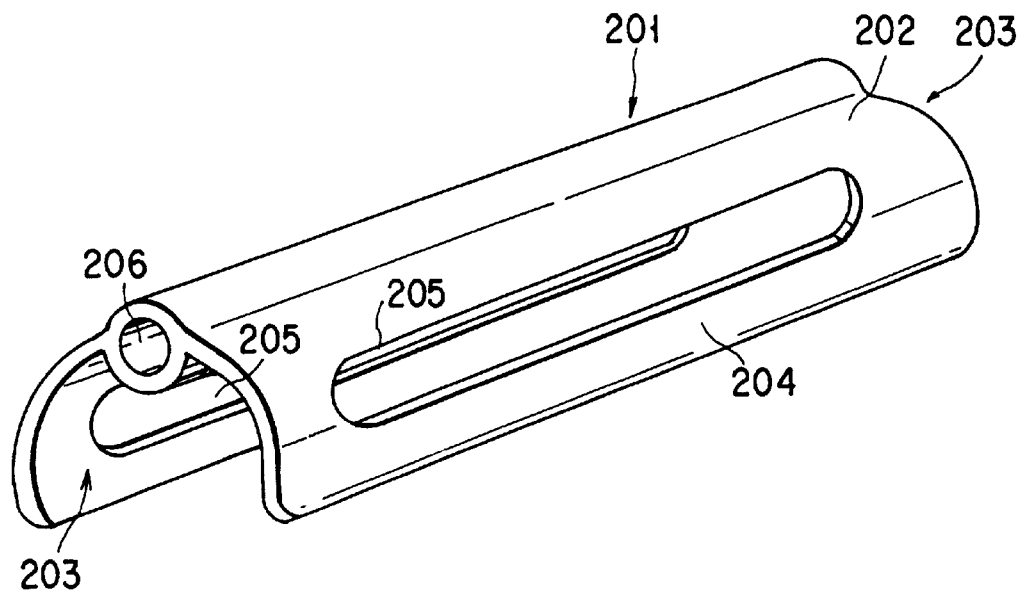
FIG. 29 is a perspective view showing a first modification of the cavity maintaining tool.
Figure 30A:
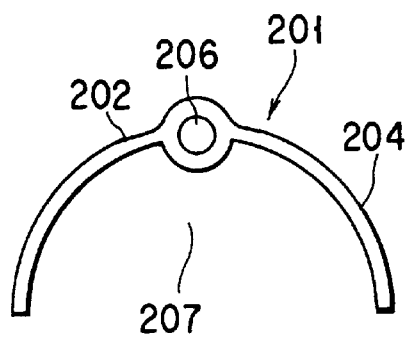
FIG. 30A is a front view showing the cavity maintaining tool shown in FIG. 29.
Figure 30B:
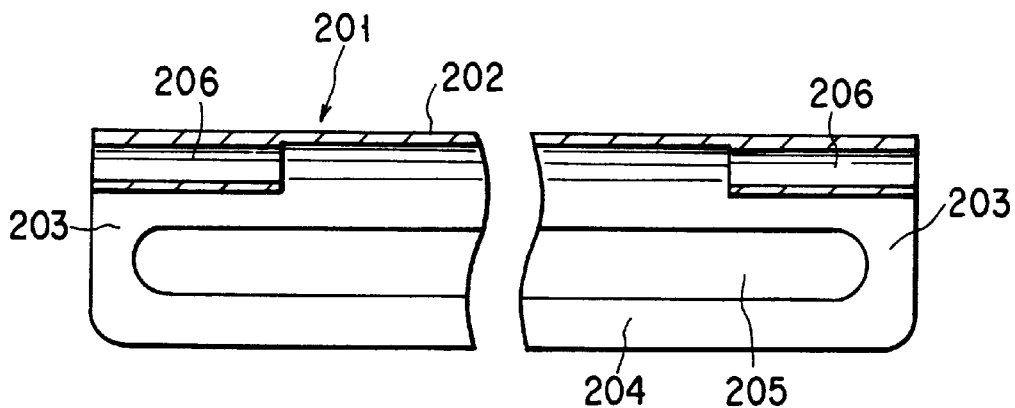
FIG. 30B is a vertical cross sectional view showing the cavity maintaining tool shown in FIG. 29.

FIGS. 29, 30A and 30B show a first modification of the cavity maintaining tool. As shown in FIGS. 29, 30A and 30B, a cavity maintaining tool 201 has a body 202 formed into a semicircular (cylindrical) shape or circular arc shape obtainable by vertically cutting a cylinder into two sections, the body 202 being made of a synthetic resin or stainless steel. The body 202 has, at the two ends in the lengthwise direction, openings 203. A side wall portion 204 of the body 202 has two ends in each of which a lateral hole 205 elongated in the lengthwise direction of the body 202 is formed. The right and left lateral hole 205 is formed symmetrically with respect to the longitudinal axis of the body 202. Moreover, the endoscope guide tube 206 is, together with the body 202, provided for each of the two ends of the body 202. Each of the endoscope guide tube 206 is disposed on a straight line running parallel to the longitudinal axis of the body 202. The portion between the endoscope guide tube 206 are disconnected.

The upper semicircular portion of the cylindrical portion of each of the endoscope guide tubes 206 projects over the side wall portion 204 of the body 202, while the lower semicircular portion projects over the lower portion of the inner portion of the side wall portion 204. By disposing the endoscope guide tube 206 at an intermediate position of the side wall portion 204, in particular, by disposing the same in the central portion, a largest possible hollow portion 207 is maintained in the cavity maintaining tool 201 while preventing excessive projection in the outward direction. The two end surfaces and the lower surface of the body 202 and the inner surface of the lateral hole 205 are rounded so as to protect the tissue in the body cavity from being damaged.

Figure 31A:
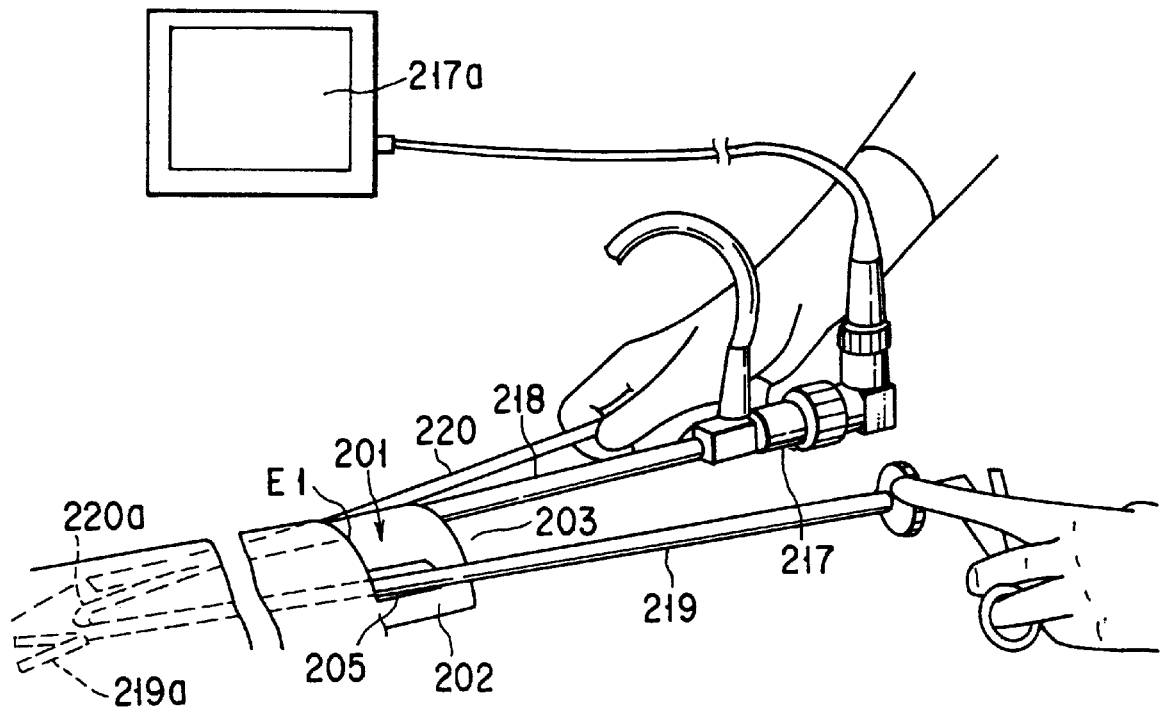
FIG. 31A is a perspective view showing a state where the cavity maintaining tool shown in FIG. 29 is used.
Figure 31B:
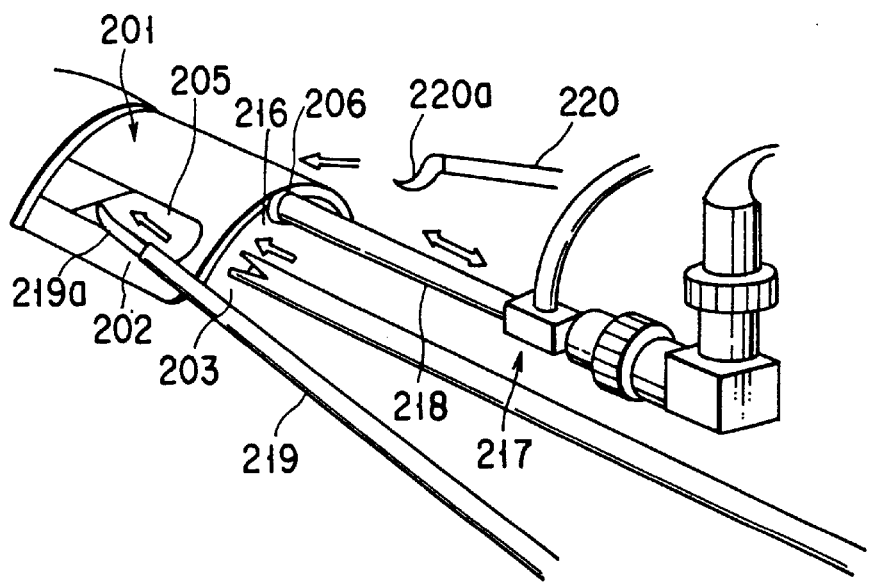
FIG. 31B is a perspective view showing a state where the cavity maintaining tool shown in FIG. 29 is used.

FIGS. 31A and 31B show a case where the cavity maintaining tool 201 is used in an extracting operation in which the same is retained in the subcutaneous tissue to extract the subcutaneous blood vessel, such as the saphenous vein. As a previous operation when the cavity maintaining tool 201 is retained, a space for retaining the cavity maintaining tool 201 is formed in the subcutaneous tissue, for example, as shown in FIG. 32.

Figure 32:
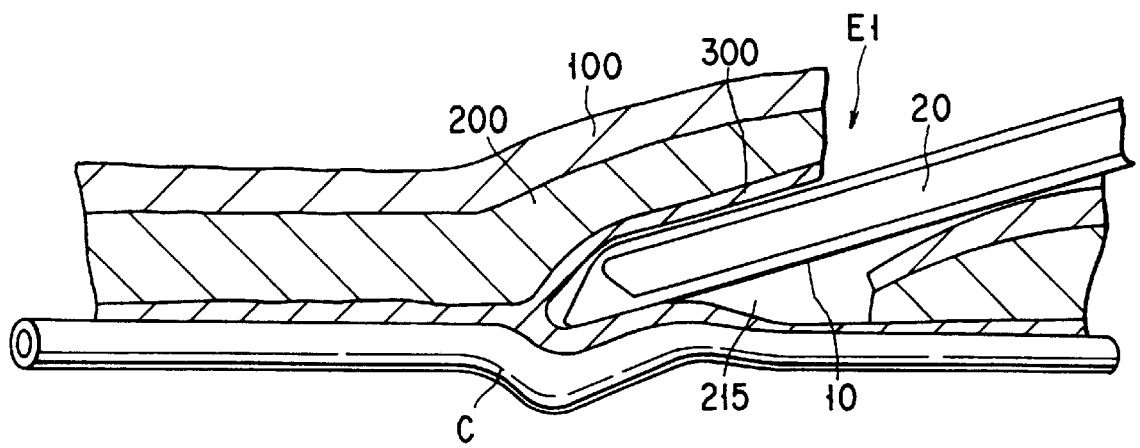
FIG. 32 is cross sectional view showing a state of treatment to be performed before the cavity maintaining tool shown in FIG. 29 is retained below the skin.

Referring to FIG. 32, reference numeral 100 represents the skin, 200 represents the subcutaneous tissue, such as the fat in the lower layer of the skin 100, 300 represents the connective tissue on the blood vessel in the lower layer of the subcutaneous tissue 200, and C represents the blood vessel, such as the saphenous vein. FIG. 32 shows a state where a portion of the skin 100 is cut by a knife, the subcutaneous tissue 200 and the connective tissue 300 on the blood vessel C are cut, the excising member 10 is inserted through the skin cut portion E1, and the retaining space 215 is formed in the body by the excising member 10 while observing the subject portion with the hard endoscope 20.

After the retaining space 215 has been formed in the body, the body 202 of the cavity maintaining tool 201 is inserted through the skin cut portion E1, as shown in FIG. 31A and 31B. In a state where the outer end opening 203 is exposed to the outside of the body, the cavity maintaining tool 201 is retained so that a cavity 216 is maintained below the subcutaneous tissue 200 by the hollow portion 207. Then, an insertion portion 218 of a hard endoscope 217 is inserted into either of the endoscope guide tubes 206 of the body 202, and the leading end of the insertion portion 218 is inserted into the cavity 216. A treatment tool, for example, cutting forceps 219, is inserted from an end of the body 202 through a lateral hole 205 to insert a forceps portion 219a into the cavity 216. Moreover, a treatment tool, for example, a hook probe 220, is inserted through either of the openings 203 of the body 202, to insert a hook portion 220a into the cavity 216.

As described above, the hard endoscope 217, the cutting forceps 219 and the hook probe 220 can simultaneously be inserted into either end of the body 202 of the cavity maintaining tool 201. Moreover, while observing the cavity 216 with the hard endoscope 217, the connective tissue 300 on the blood vessel C can be separated from the blood vessel C and the connective tissue 300 on the blood vessel C can be cut by the cutting forceps 219 so as to separate the connective tissue 300 on the blood vessel C from the blood vessel C.

Figure 33:
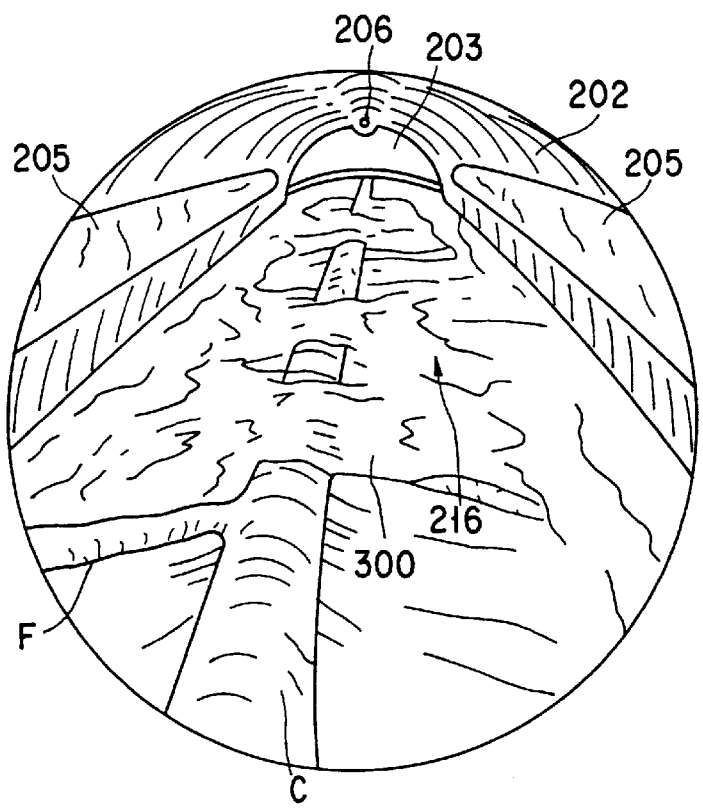
FIG. 33 shows an image observed with the endoscope to illustrate a state in the cavity formed by the cavity maintaining tool shown in FIG. 29.
Figure 36:
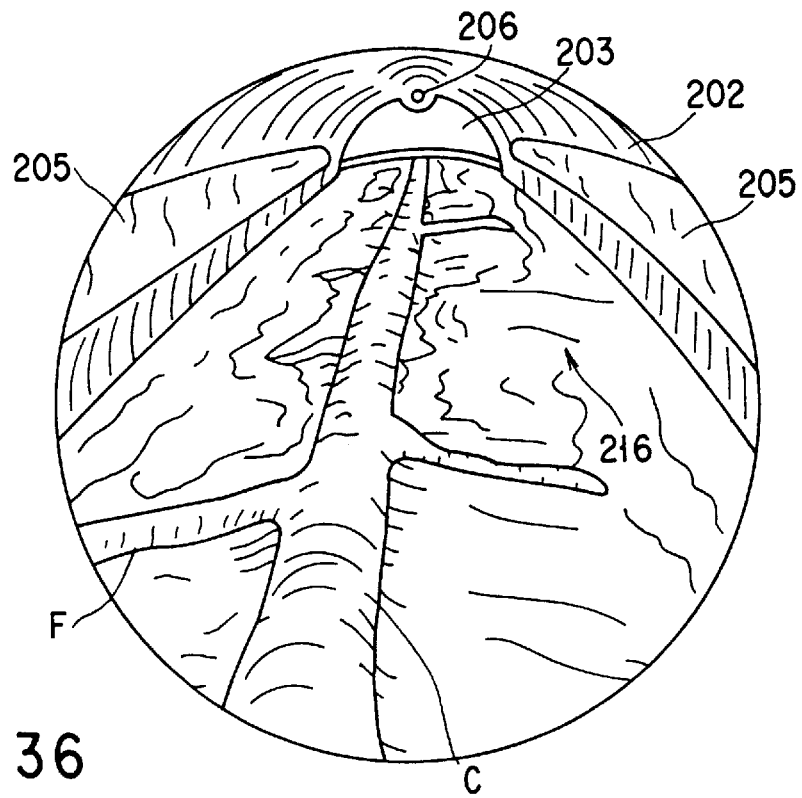
FIG. 36 shows an image observed with the endoscope to illustrate a state in the cavity formed by the cavity maintaining tool shown in FIG. 29.
Figure 37:
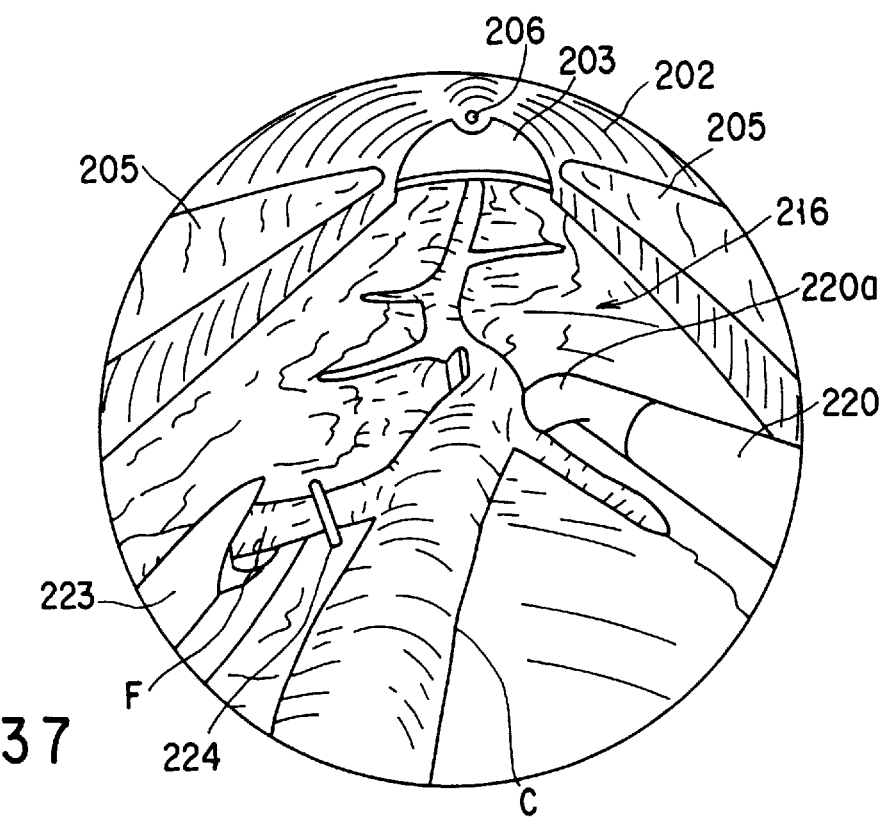
FIG. 37 shows an image observed with the endoscope to illustrate a state in the cavity formed by the cavity maintaining tool shown in FIG. 29.

FIG. 33 shows an image of the inside portion of the cavity 216 picked up by the hard endoscope 217 to be displayed on a monitor 217a. As shown in FIG. 33, the inner wall of the body 202, the opening 203 and the lateral hole 205 of the cavity maintaining tool 201, the connective tissue 300 on the blood vessel C, the blood vessel C and the branch F extending from an intermediate position of the blood vessel C into the horizontal direction can easily be observed. FIG. 34 shows a state where the cutting forceps 219 has been inserted into the guide groove 222 of the scissors guide 221 to cause the cutting forceps 219 to slide in the guide groove 222 so that the cutting forceps 219 is enabled to easily approach the connective tissue 300 on the blood vessel C. FIG. 35 shows a state immediately before the connective tissue 300 on the blood vessel C is cut by the cutting forceps 219. FIG. 36 shows a state where the connective tissue 300 on the blood vessel C has been cut by the cutting forceps 219 and, thus, the blood vessel C and the branch F have been exposed. FIG. 37 shows a state where a clip 224 is deformed by a clip prier 223, which is a treatment tool and an intermediate position of the branch F is held. FIG. 38 shows a state immediately before an intermediate position of the branch F held by the two clips 224 is cut by the cutting forceps 219 and a state after the same has been cut. As described above, the cavity maintaining tool 201 can easily be used in a variety of states of usage.

FIG. 39 shows a second modification of the cavity maintaining tool. The same elements as those of the first modification are given the same reference numerals and they are omitted from detailed description. A cavity maintaining tool 225 according to this modification has a similar shape as that according to the first modification. A body 226 has a semicircular (cylindrical) shape or circular arc shape obtainable by vertically cutting a cylinder into two sections, the body 206 being made of a synthetic resin or stainless steel. The body 206 has, at the two ends in the lengthwise direction, openings 227. The lower portions of the two ends of a side wall portion 228 of the body 226 have elongated horizontal holes 229 formed in the lengthwise direction of the body 226, the horizontal holes 229 being in the form of cut portions. The right and left horizontal holes 229 are formed symmetrically with respect to the lengthwise direction axial line of the body 226. Also the cavity maintaining tool 225 can be used similar to the cavity maintaining tool 201 according to the first modification.

Figure 40:
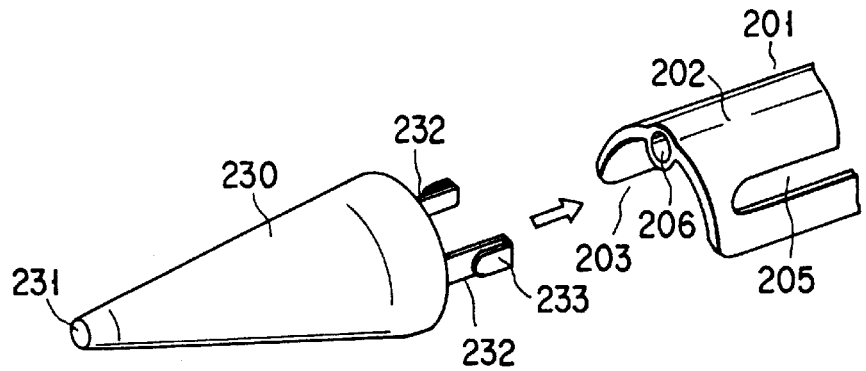
FIG. 40 is a perspective view showing a cavity maintaining tool and an insertion helper according to a third modification.
Figure 41:
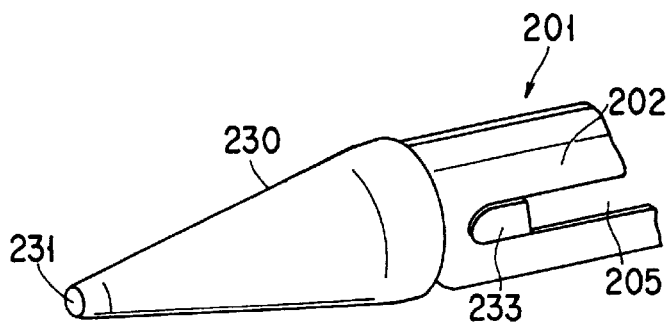
FIG. 41 is a perspective view showing a state where the insertion helper has been attached to the cavity maintaining tool shown in FIG. 40.

FIG. 40 and 41 show a third modification of the cavity maintaining tool. Note that the same elements as those of the first modification are given the same reference numerals and they are omitted from illustration. The cavity maintaining tool 201 according to this modification is used together with an insertion helper 230. The insertion helper 230 has a conical cylinder shape, only the lower portion thereof is flattened or in the form obtainable by vertically cutting a conical cylinder and employing only the upper portion. A leading end 231 of the insertion helper 230 is rounded to protect the tissue from being damaged. The base portion of the insertion helper 230 has substantially same curvature radius as that of the body 202 of the cavity maintaining tool 201 so that no step is formed when connected.

A pair of connection members 232 positioned to correspond to the lateral hole 205 of the body 202 of the cavity maintaining tool 201, projecting rearwards and having elasticity are provided for the base portion of the insertion helper 230. The leading end of the projecting portion of the connection member 232 has an engaging projection 233 in the form of a bent hook to be engaged to the leading end of the lateral hole 205 of the body 202 of the cavity maintaining tool 201.

When the insertion helper 230 having the foregoing structure is placed to face the end of the body 202 of the cavity maintaining tool 201 and then the leading end of the projecting portion of each of the connection members 232 is inserted into the body 202, the elasticity of the connection members 232 causes the engaging projection 233 to be inserted into the lateral hole 205 of the body 202. Thus, the insertion helper 230 is connected to the body 202 by a single action. Therefore, when the cavity maintaining tool 201 is inserted into the retaining space 215 in the subcutaneous tissue 200, the subcutaneous tissue 200 can be expanded by the tapered surface of the insertion helper 230 at the time of insertion. Thus, the cavity maintaining tool 201 can easily be inserted.

Figure 42A:
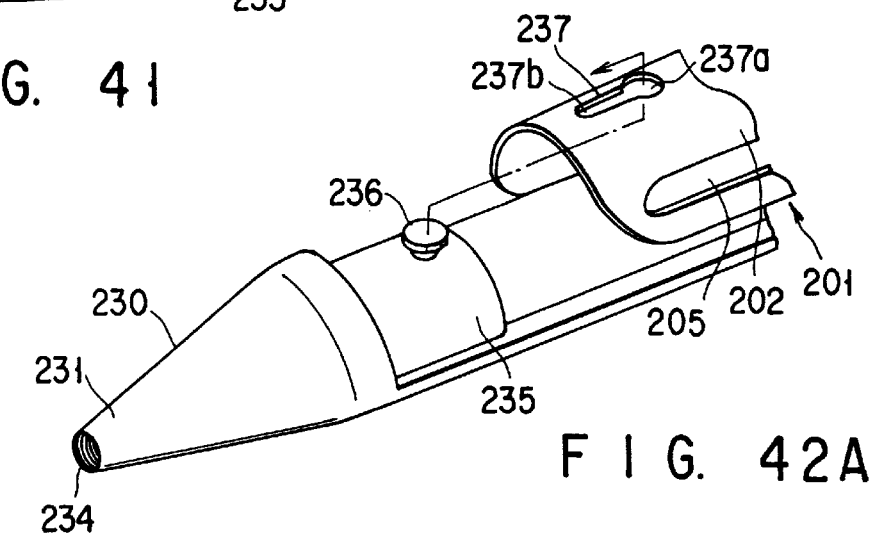
FIG. 42A is a perspective view showing a cavity maintaining tool and an insertion helper according to a fourth modification.
Figure 42B:
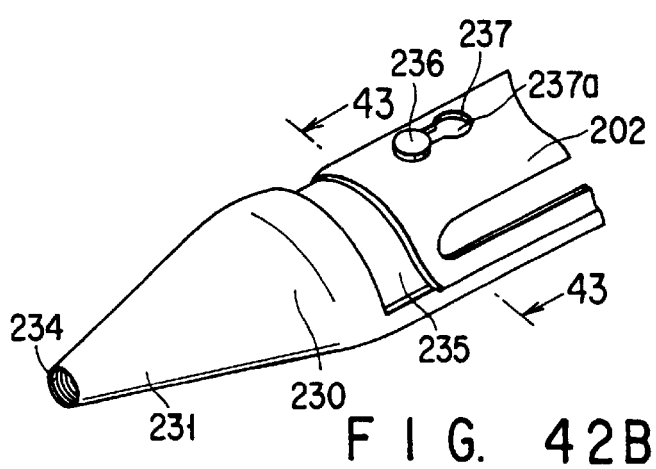
FIG. 42B is a perspective view showing a state where the insertion helper has been attached to the cavity maintaining tool shown in FIG. 42A.
Figure 43:
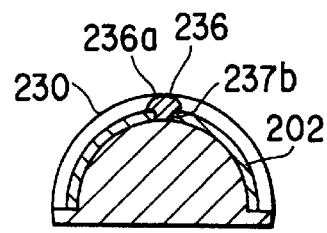
FIG. 43 is a cross sectional view taken along line 43—43 shown in FIG. 42B.

FIGS. 42A, 42B and 43 show a fourth modification of the cavity maintaining tool. Note that the same elements as those of the first and third modifications are given the same reference numerals and they are omitted from description. The cavity maintaining tool 201 according to this modification is used together with the insertion helper 230. A thread hole 234 for connecting a traction member (not shown) is formed in a leading end 231 of the insertion helper 230. As shown in FIG. 43, the base portion of the insertion helper 230 has a diameter slightly larger than that of the body 202 of the cavity maintaining tool 201. The base portion has a semicircular connection member 235 projecting rearwards. A connection pin 236 having a head portion 236a, the height of which is the same or lower than the upper surface of the base portion of the insertion helper 230 is allowed to project over the upper surface of the connection member 235.

On the other hand, an engaging hole 237 to be engaged to the connection pin 236 is formed in the upper surface of the body 202 of the cavity maintaining tool 201. The engaging hole 237 is composed of a large-diameter portion 237a to be freely engaged to the head portion 236a of the connection pin 236 and a small-diameter portion 237b to be closely engaged to the shaft portion of the connection pin 236, the large-diameter portion 237a and the small-diameter portion 237b being formed continuously in the longitudinal direction. The large-diameter portion 237a is disposed in the rear of the small-diameter portion 237b.

The insertion helper 230 having the foregoing structure is located to face the end of the body 202 of the cavity maintaining tool 201, and the connection member 235 is inserted into the opening 203 of the body 202. Then, the head portion 236a of the connection pin 236 is freely inserted into the large-diameter portion 237a of the engaging hole 237. When the insertion helper 230 is moved toward the leading end 231 in the foregoing state, the connection pin 236 is closed engaged to the small-diameter portion 237b of the engaging hole 237 so that the insertion helper 230 is connected to the body 202 by a single action.

By using the insertion helper 230, when the cavity maintaining tool 201 is inserted into the retaining space 215 of the subcutaneous tissue 200, it can be inserted while expanding the subcutaneous tissue 200 by the tapered surface of the insertion helper 230. As a result, the cavity maintaining tool 201 can easily be inserted.

Figure 44:
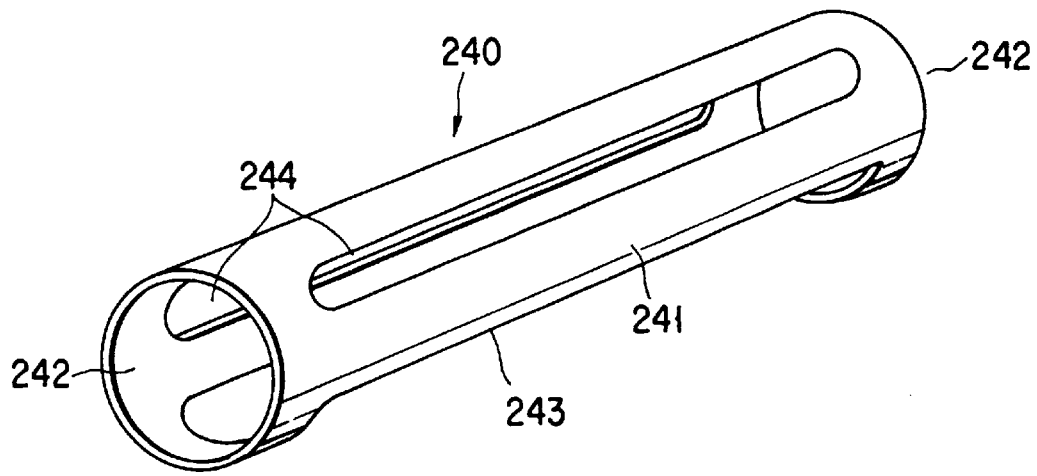
FIG. 44 is a perspective view showing a fifth modification of the cavity maintaining tool.

FIG. 44 shows a fifth modification of the cavity maintaining tool. Referring to FIG. 44, reference numeral 240 represents cavity maintaining tool. The cavity maintaining tool 240 has a body 241 formed into a cylindrical shape. The body 241 has the two ends each having an opening 242. An opening portion 243 in the form of a wide and elongated hole is formed in the lower portion of the body 241 in the lengthwise direction of the body 241. On the other hand, a pair of horizontal holes 244 are formed in the peripheral wall in the upper portion of the body 241, the horizontal holes 244 being formed in the lengthwise direction of the body 241. Also the cavity maintaining tool 240 can be used similarly to the cavity maintaining tool according to the foregoing modifications.

Figure 45A:
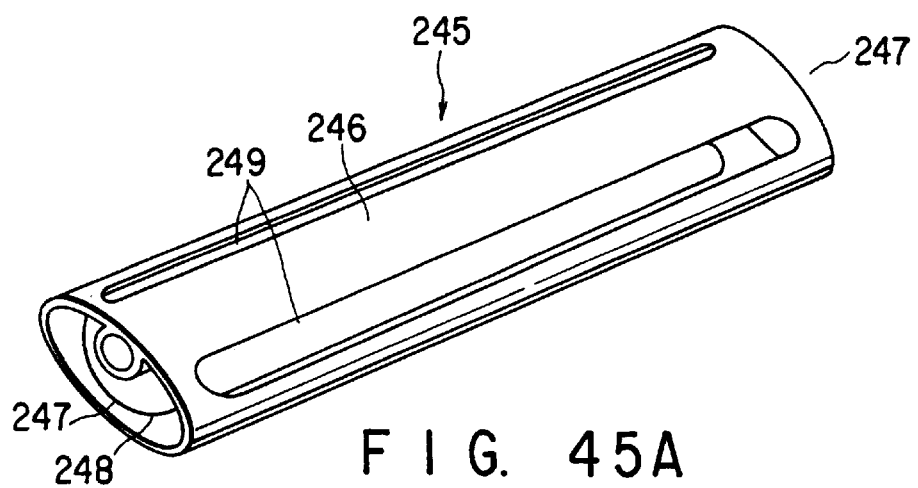
FIG. 45A is a perspective view showing a cavity maintaining tool according to a sixth modification when viewed from an upper position.
Figure 45B:
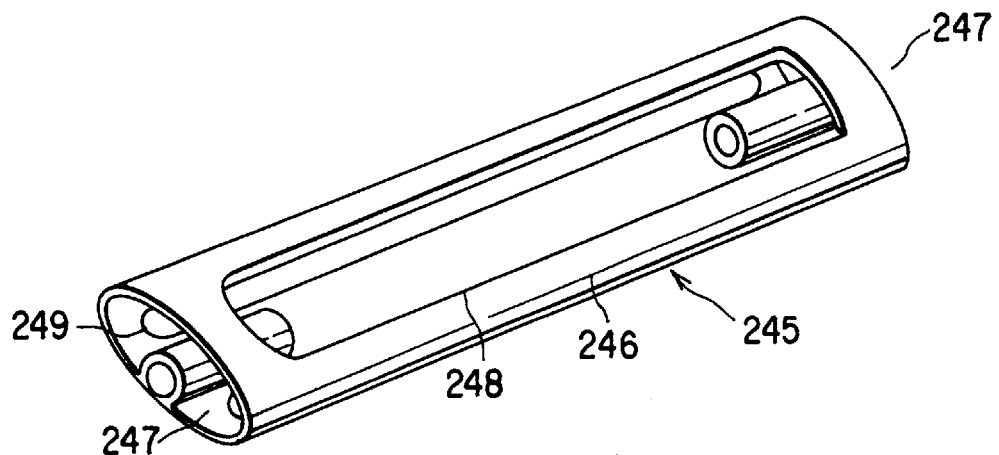
FIG. 45B is a perspective view showing the cavity maintaining tool shown in FIG. 45A when viewed from a lower position.

FIGS. 45A and 45B show a sixth modification of the cavity maintaining tool. Referring to FIGS. 45A and 45B, reference numeral 245 represents a cavity maintaining tool. A body 246 of the cavity maintaining tool 245 is formed into a flat cylindrical shape having two ends in which openings 247 are formed. An opening portion 248 in the form of a wide elongated hole is formed in the lower portion of the body 246, the opening portion 248 being formed in the lengthwise direction of the body 246. Also the cavity maintaining tool 245 can be used similarly to the cavity maintaining tool according to each of the foregoing modifications.

FIGS. 46A and 46B show a seventh modification of the cavity maintaining tool. Referring to FIGS. 46A and 46B, reference numeral 250 represents a cavity maintaining tool. A body 251 of the cavity maintaining tool 250 is formed into a semicircular (cylindrical) shape which is the upper half of two sections formed by vertically cutting a cylinder. The body 251 has an opening at each of the two ends thereof. Moreover, a cut portion 253 is formed in the upper wall at each of the two ends of the body 251. The cut portion 253 expands the degree of opening of the opening 252 to enable a treatment tool 254 to easily be inserted and operated. A pair of leg portions 255 formed by the cut portion 253 extend outwards in the axial direction of the body 251 to press tissue 256 so that a treatment tool 254 is easily inserted and operated. Reference numeral 257 represents an endoscope guide tube similar to that according to the foregoing modifications.

FIG. 47 shows an eighth modification of the cavity maintaining tool. Referring to FIG. 47, reference numeral 258 represents a cavity maintaining tool. A body 259 of the cavity maintaining tool 258 is formed into a semicircular (cylindrical) shape which is the upper half of two sections formed by vertically cutting a cylinder. The body 259 has the two ends in which openings 260 are formed by expanding the outer wall of the body 259. The opening 260 has a satisfactorily large size to easily insert and operate the treatment tool 254.

FIGS. 48A and 48B show a ninth modification of the cavity maintaining tool. Referring to FIGS. 48A and 48B, reference numeral 261 represents a cavity maintaining tool. A body 262 of the cavity maintaining tool 261 is formed into a semicircular (cylindrical) shape which is the upper half of two sections formed by vertically cutting a cylinder. Moreover, openings 263 are formed in the two ends of the body 262. Two horizontal holes 264 are formed on the two side walls of the body 262, the horizontal holes 264 being formed in the lengthwise direction of the body 262. The horizontal holes 264 are covered with a semicircular (cylindrical) cover 265 projecting toward the outside of the body 262. An end of the cover 265 is opened so that the horizontal hole 264 is opened, while another end is closed. Thus, a tapered shape is formed from the opened portion toward the closed portion to guide the treatment tool 219. As shown in FIG. 48B, for example, the cutting forceps 219 can be inserted through the horizontal hole 264 and the insertion portion 218 of the hard endoscope 217 can be inserted into the endoscope guide tube 206. As a result, treatment can be performed while observing the inside portion of the cavity 216.

Figure 49:
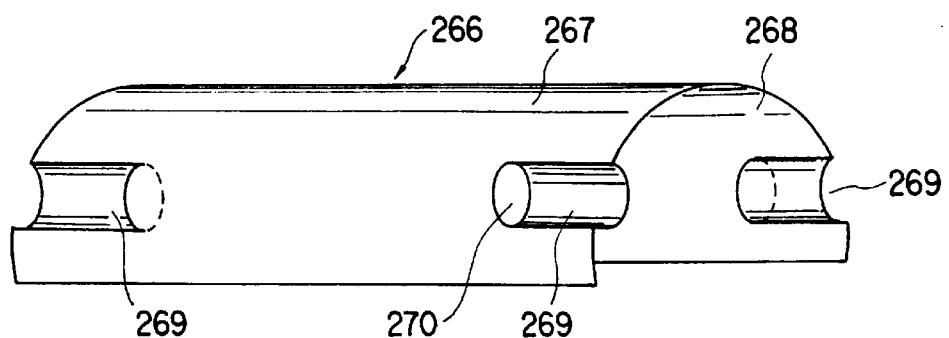
FIG. 49 is a perspective view showing a tenth modification of the cavity maintaining tool.

FIG. 49 shows a tenth modification of the cavity maintaining tool. Referring to FIG. 49, reference numeral 266 represents a cavity maintaining tool. A body 267 of the cavity maintaining tool 266 is formed into a semi-cylindrical shape obtained by vertically cutting a cylinder. Moreover, an opening 268 is formed in each of the two ends of the body 267. The opening 268 may be formed by opening the outer wall of the body 267. By inwardly deforming each of the two side walls at the two ends of the body 267 into a semicircular shape, a circular-arc guide groove 269 is formed on the outer wall of each of the two side walls. Moreover, a horizontal hole 270 connected to the inner portion of the body 267 is formed at an end of the guide groove 269. Therefore, a treatment tool (not shown) can be inserted into the body 267 through the horizontal hole 270 while being guided by the guide groove 269.

Figure 50:
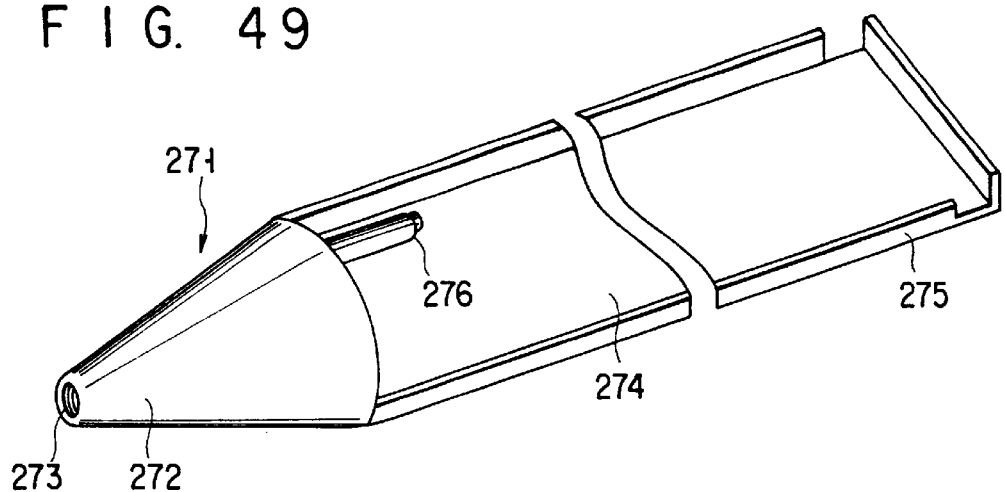
FIG. 50 is a perspective view showing an insertion helper to be used together with a cavity maintaining tool according to an eleventh modification.

FIGS. 50 to 54 show an eleventh modification of the cavity maintaining tool. A cavity maintaining tool 201 according to this modification is used together with an insertion helper 271. As shown in FIGS. 50, 51A and 51B, a leading end portion 272 of the insertion helper 271 has a thread hole 273 to which a traction member (not shown) is connected. Moreover, a rectangular retainer plate 274, on which the hard endoscope body 202 of the cavity maintaining tool 201 is placed, is fixed to the base portion of the insertion helper 271. A raised and bent edge portion 275 to be engaged to the lower edge of the body 202 of the cavity maintaining tool 201 is formed in the peripheral portion of the retaining plate 274. Moreover, a connection pin 276 is formed to project over the base portion of the insertion helper 271, the connection pin 276 being arranged to be inserted into the endoscope guide tube 206 of the cavity maintaining tool 201.

Figure 51A:
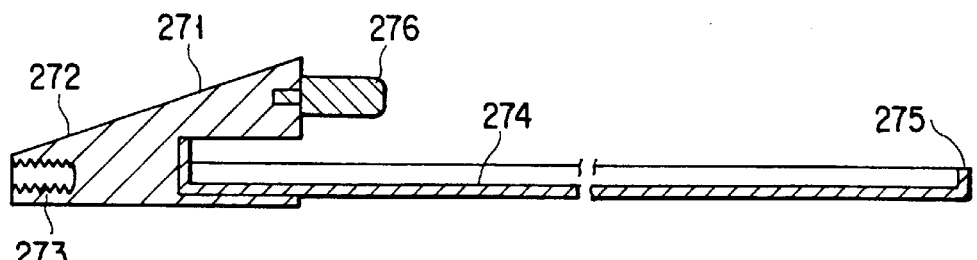
FIG. 51A is a vertical cross sectional view showing the insertion helper shown in FIG. 50.
Figure 51B:
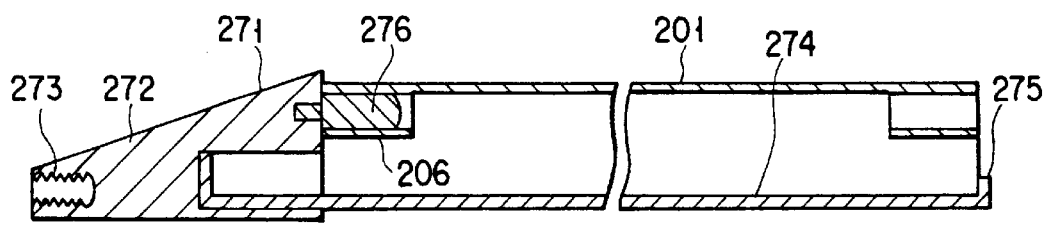
FIG. 51B is a vertical cross sectional view showing a state where the cavity maintaining tool according to the eleventh modification has been attached to the insertion helper shown in FIG. 50.

With the insertion helper 271 having the foregoing structure, when the endoscope guide tube 206 of the cavity maintaining tool 201 is, as shown in FIG. 51B, inserted into the connection pin 276 and the cavity maintaining tool 201 is placed on the retaining plate 274, the cavity maintaining tool 201 can be connected to the insertion helper 271 with a single action. When the cavity maintaining tool 201 is inserted into the retaining space 215 of the subcutaneous tissue 200, it can be inserted while expanding the subcutaneous tissue 200 by the tapered surface of the insertion helper 271. Thus, the insertion of the cavity maintaining tool 201 can be facilitated.

Figure 52:
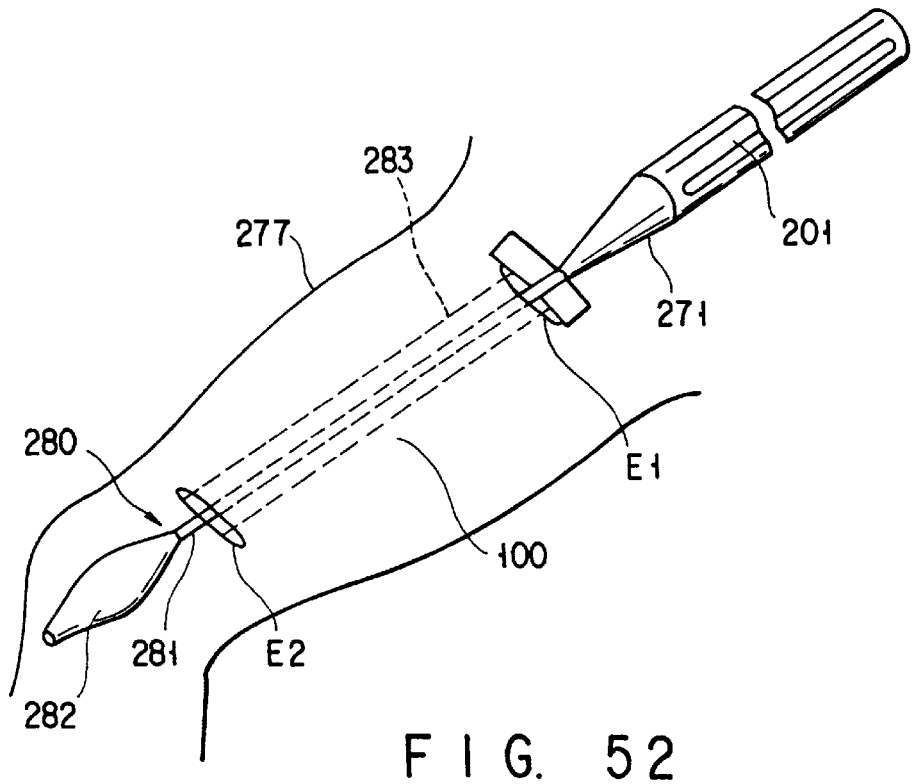
FIG. 52 is a perspective view showing a state where the cavity maintaining tool according to the eleventh modification is used.
Figure 53:
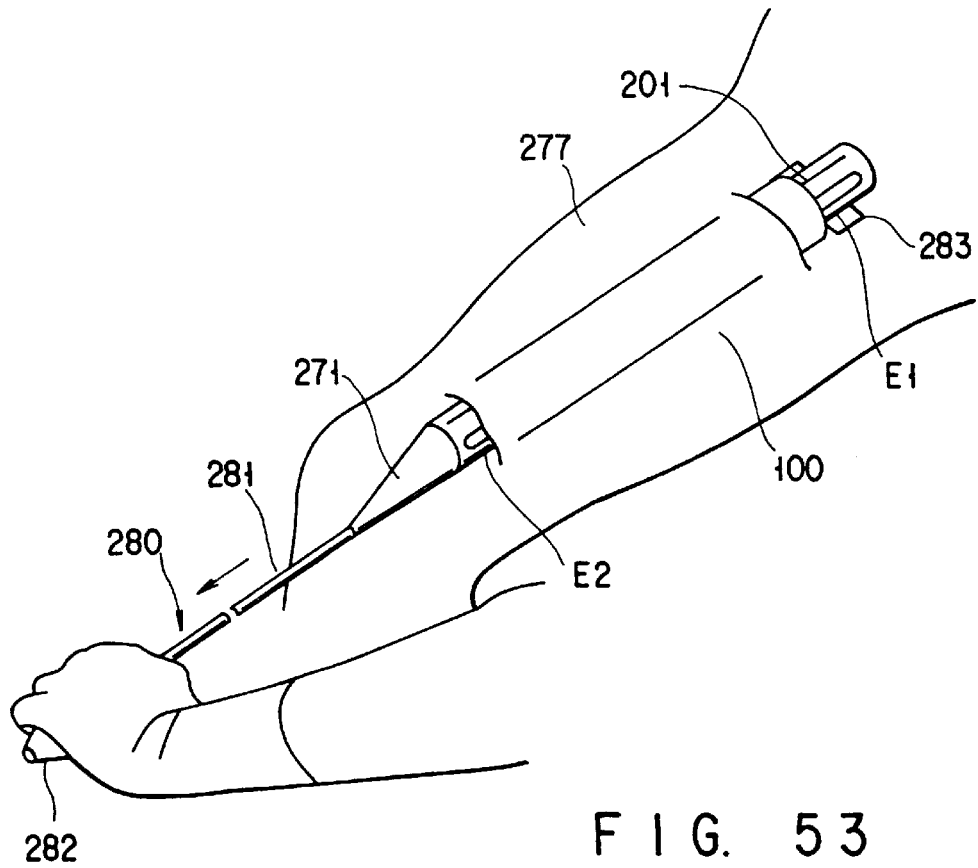
FIG. 53 is a perspective view showing a state where the cavity maintaining tool according to the eleventh modification is used.
Figures 54, 55, 56A, 56B, 57:
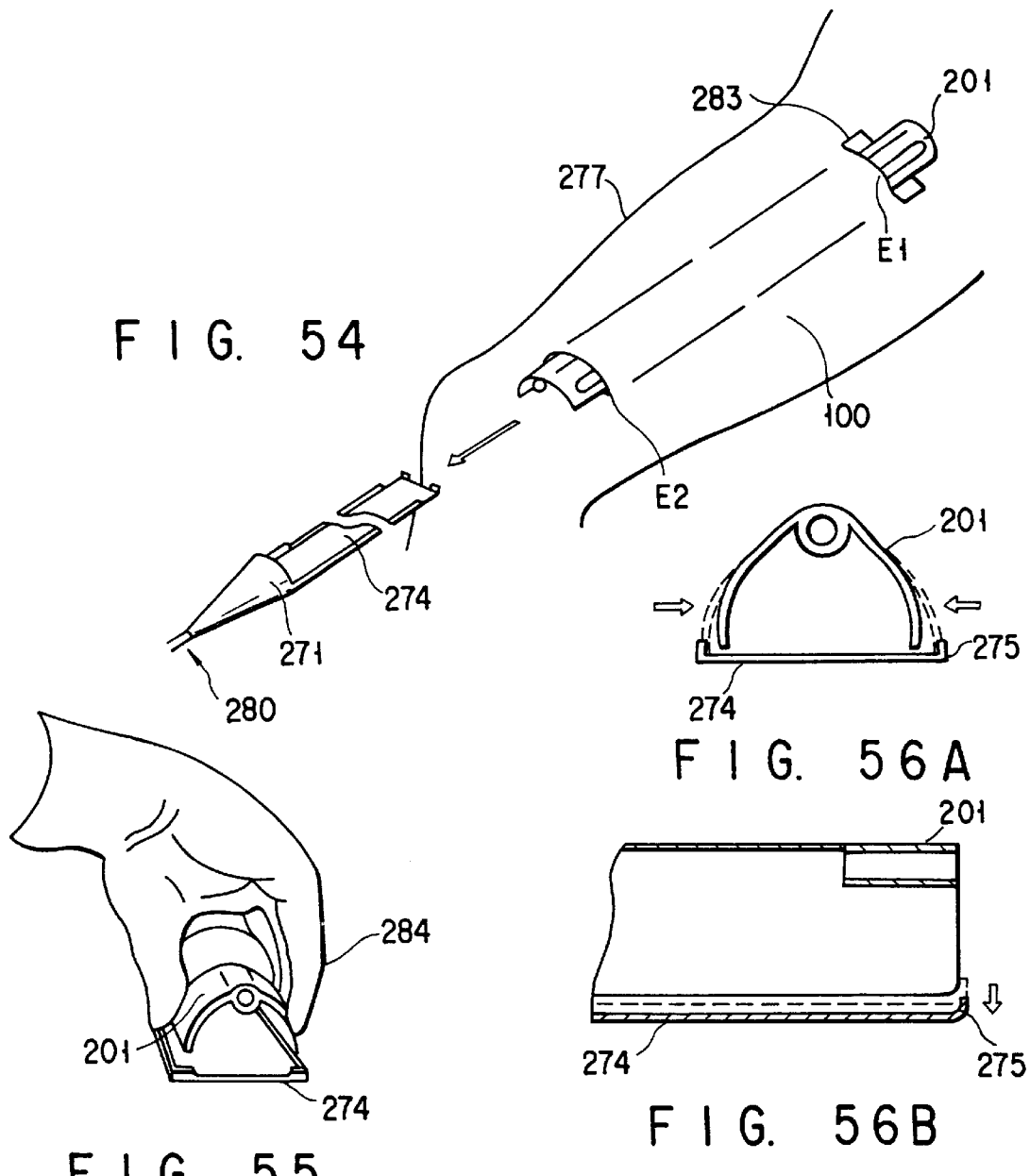
FIG. 54 is a perspective view showing a state where the cavity maintaining tool according to the eleventh modification is used.
FIG. 55 is a perspective view showing a modification of the attaching/detaching means according to the eleventh modification.
FIG. 56A is a front view showing the attaching/detaching means shown in FIG. 55.
FIG. 56B is a side view showing the attaching/detaching means shown in FIG. 55.
FIG. 57 is a perspective view showing a state where the cavity maintaining tool according to a twelfth modification is used.

FIGS. 52 to 54 show an operation for inserting the cavity maintaining tool 201 into the retaining space 215 of the subcutaneous tissue 200 by using the insertion helper 271 according to this modification. Reference numeral 277 represents a lower extremity, and E1 and E2 represent skin cut portions formed by cutting the skin 100 by a knife or the like. A expander 280, serving as a traction member, is connected to the thread hole 273 of the insertion helper 271. The expander 280 is composed of a shaft 281 and a flat expansion portion 282 formed at an end of the shaft 281. Reference numeral 283 represents a protector previously set in the retaining space 215 of the subcutaneous tissue 200 in order to guide the insertion helper 271 and the cavity maintaining tool 201.

The expansion portion 282 of the expander 280 is, as a leading end of the insertion operation, introduced into the retaining space 215 of the subcutaneous tissue 200 through skin cut portion E1 which is one of the skin cut portions E1 and E2. On the other hand, the expansion portion 282 is ejected through the other skin cut portion E2. In this state, the operator holds the expansion portion 282 as a handle and pulls in a direction indicated by an arrow so that the expansion portion 282 is inserted while expanding the subcutaneous tissue 200 by the tapered surface of the insertion helper 271. Then, the cavity maintaining tool 201 is inserted into the retaining space 215 of the subcutaneous tissue 200, and then the two ends of the cavity maintaining tool 201 are retained while being exposed through the skin cut portions E1 and E2. After the two ends have been exposed, the insertion helper 271 and the cavity maintaining tool 201 are separated from each other.

FIGS. 55, 56A and 56B show an example of a structure which is different from the eleventh modification in a means for attaching/detaching the cavity maintaining tool 201 to and from the insertion helper 271. That is, when the operator holds the two side walls of the body 202 of the cavity maintaining tool 201 with fingers 284 to elastically and inwards deform the body 202 to suspend the engagement of the body 202 with the raised portion 275 of the insertion helper 271, followed by downwards pushing the retaining plate 274 of the insertion helper 271, the insertion helper 271 and the cavity maintaining tool 201 can be separated from each other.

Figure 58:
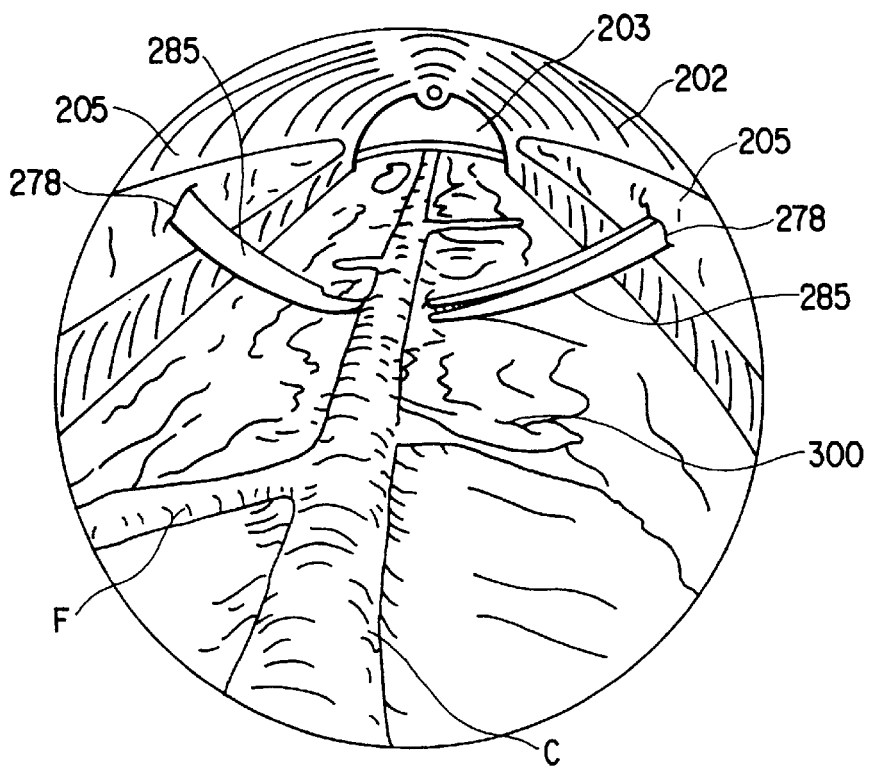
FIG. 58 shows an image observed with the endoscope in a state where the cavity maintaining tool according to the twelfth modification is used.
Figure 59:
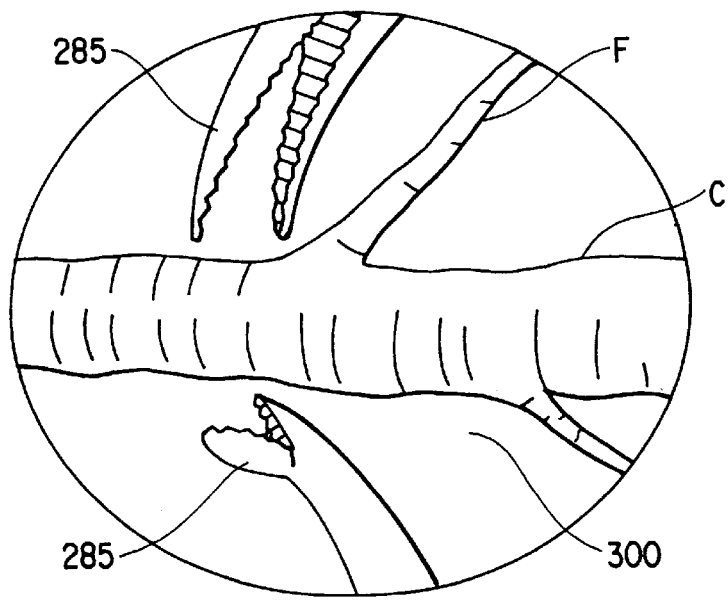
FIG. 59 shows an image observed with the endoscope in a state where the cavity maintaining tool according to the twelfth modification is used.

FIGS. 57 to 59 show a twelfth modification of the cavity maintaining tool. FIG. 57 shows a state where forceps 285 for a surgical operation are inserted into the subcutaneous tissue 200 through the lateral hole 205 of the cavity maintaining tool 201 retained in the subcutaneous tissue 200. The hard endoscope 217 is inserted through the opening 203, which is one of two openings of the cavity maintaining tool 201. Moreover, the skin 100 opposite to the lateral hole 205 of the cavity maintaining tool 201 is cut by a knife or the like. The forceps 285 for a surgical operation are inserted into the cavity 216 through a formed skin cut portion 278. FIG. 58 shows an image of the inside portion of the cavity 216. The forceps 285 for a surgical operation, the inner wall of the body 202 of the cavity maintaining tool 201, the opening 203, the lateral hole 205, the connective tissue 300 on the blood vessel C, the blood vessel C and the branch F extending at an intermediate position of the blood vessel C toward a horizontal direction can be observed. FIG. 59 shows a closed up image of a forceps portion 285a of the forceps 285 for a surgical operation and the blood vessel C photographed by a squint type hard endoscope. A clear image of detailed portions can be captured.

FIGS. 60A to 60C show a thirteenth modification of the cavity maintaining tool. FIG. 60A shows a cavity maintaining tool 286 in an assembled state. The cavity maintaining tool 286 can be decomposed into a plurality of members, as shown in FIGS. 60B and 60C. That is, the cavity maintaining tool 286 is composed of a cavity maintaining tool 286, the body 288 and the handle portion 289 so that decomposition of the foregoing elements is enabled. The body 288 of the cavity maintaining tool 286 has shafts 291 provided by a number suitable to maintain the cavity; and an endoscope guide tube 292 for holding the scope. The shafts 291 and the endoscope guide tube 292 are arranged between bases 290 disposed at the two longitudinal ends of the body 288. The shafts 291 and the endoscope guide tube 292 are formed into a frame structure running parallel to the axis direction of the body 288.

The bases 290 disposed at the two longitudinal ends of the body 288 are in the same arch shape and have an opening 293 for enabling the treatment tool to be smoothly inserted. The endoscope guide tube 292 is arranged between the two bases 290 at a position on the rear of the central portion of the bases 290. The plural shafts 291 are arranged between legs 294 of the bases 290. Since the shafts 291 and the endoscope guide tube 292 are formed in the frame shape running parallel to the axial direction of the body 288, a plurality of lateral holes 205 are greatly opened in the side portion of the body 288, the lateral holes 205 being connected to the hollow portion 296 in the body 288.

A pin-type locating member 295 is formed to project over the front wall in the lower portion of each of the two leg portions 294 of the bases 290, the locating member 295 being provided for position location with respect to the insertion helper 287. The two end surfaces, the lower surface and the side surfaces, which come in contact with the subject subcutaneous tissue, of the body 288 are rounded without any edge. Each member of the cavity maintaining tool 286 is made of a synthetic resin or stainless steel. The endoscope guide tube 292 of the body 288 has, similarly to that of the first modification, a hole portion 292a having two ends which are opened in the longitudinal direction. The intermediate portion of the endoscope guide tube 292 is opened in a hollow portion 296 in the body 288.

The handle portion 289 is made of a straight rod member having a base portion on which a large-diameter handle portion 297. The handle portion 289 has a securing male thread portion 298 at the leading end thereof. The handle portion 289 is inserted into the endoscope guide tube 292 of the body 288. The male thread portion 298 of the insertion helper 287 is screwed in the female portion 299 formed in the rear end surface of the insertion helper 287. Moreover, the body 288 is held and secured between the rear end surface of the insertion helper 287 and the handle portion 297. By removing the handle portion 289, the insertion helper 287, the body 288 and the handle portion 289 can be decomposed.

The insertion helper 287 is formed into a semi-conical shape having a rounded leading end. The surface of the lower end portion of the insertion helper 287 is formed into a flat shape to form a hollow portion therein. A leading end 287a of the insertion helper 287 has a guide projection 287b. The guide projection 287b projects slightly over the lower surface of the insertion helper 287. Thus, when the cavity maintaining tool 286 is retained in the subject subcutaneous tissue, the guide projection 287b is received by a guide groove 301a of an elongated tissue protector 301, which has been previously inserted. The leading end 287a of the insertion helper 287 is, when combined with the tissue protector 301, received in the guide groove 301a of the tissue protector 301. The insertion helper 287 has, at the rear end thereof, a locating hole 302 which receives the locating member 295 of the body 288. At the leading end of the tissue protector 301, a hooking hole 301b is formed. The tissue protector 301 has, at the rear end thereof, a flap 301c extending to the right and left.

The operation of the cavity maintaining tool 286 will now be described. As shown in FIG. 60A, the cavity maintaining tool 286 is fixedly assembled as described above, such that the handle portion 289 is inserted into the endoscope guide tube 292 of the body 288, the male thread portion 298 of the handle portion 289 is screwed in the female portion 299 formed in the rear end surface of the insertion helper 287, and the body 288 is held between the rear end surface of the insertion helper 287 and the handle portion 297. The tissue protector 301 for protecting the subject tissue from being damaged is inserted through either of cut portions previously formed for retaining the cavity maintaining tool 286 to be apart from each other. The tissue protector 301 is retained in the cavity such that it is pulled to be moved forwards from the forward cut portion by hooking hole 301b to the slit 13a of the excising member 10 and pulling the excising member 10, as shown in FIG. 8A and FIG. 8B. The tissue protector 301 is retained just above the blood vessel to be evulsed.

The guide projection 287b of the insertion helper 287 is received in the guide groove 301a of the tissue protector 301 as described above. Then, the tapered surface of the insertion helper 287 expands the subcutaneous tissue so that insertion is performed. Since the cavity maintaining tool 286 has round portion on the side surface in the lengthwise direction which comes in contact with the subject tissue, the tissue in the body cavity can be protected from being damaged. Since the leading end 287a of the insertion helper 287 is received in the guide groove 301a when combined with the tissue protector 301, the relatively sharp leading end 287a does not damage the subject tissue when the cavity maintaining tool 286 is retained in the subject tissue. As a result insertion to the position below the skin can easily be performed along the subject tissue. After insertion has been performed, the insertion helper 287 is taken out through the front cut portion, while the tissue protector 301 and the handle portion 289 are taken out through the rear cut portion so as to be removed from the body 288. Thus, the retained body 288 results in a satisfactorily large cavity to be maintained in the portion below the skin.

If a method in which the front cut portion is not formed is employed, the insertion helper 287 may be retained and the tissue protector 301 is pulled toward the operator so as to be removed. Since the body 288 is in the form of the frame structure, the treatment tool can be inserted through the lateral holes 205 opened greatly simultaneously with insertion of the endoscope through the leg portions 294 at the two ends through the endoscope guide tube 292. Thus, the operation can be performed further easily as compared with the foregoing modifications. The cavity maintaining tool according to first to twelfth modifications is formed into a cylindrical shape or the like having the lateral holes 205 which opens the side portion. Although a satisfactory effect can be obtained, the thirteenth modification employing the frame structure positively and greatly opens the lateral holes 205 of the body 288. Thus, the treatment tool can be operated further smoothly in the cavity. Since the frame structure is employed, the cavity can be maintained while opening the lateral holes 205. Moreover, the strength of the body 288 can be improved.

Figure 61A:
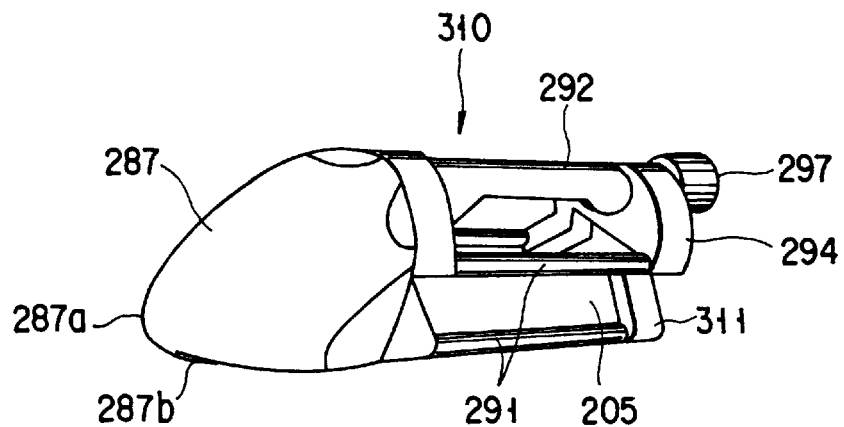
FIG. 61A is an assembled perspective view showing a cavity maintaining tool according to a fourteenth modification.
Figure 61B:
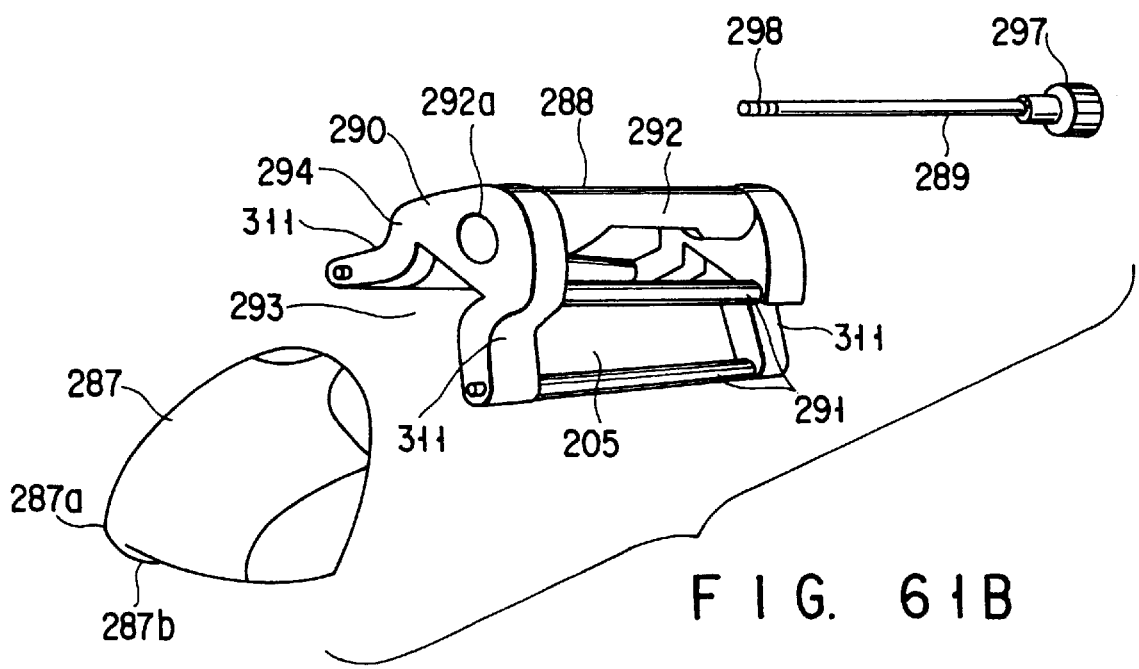
FIG. 61B is an exploded perspective view showing the cavity maintaining tool according to the fourteenth modification.

FIGS. 61A and 61B show a fourteenth modification of the cavity maintaining tool. Note that the same elements as those of the thirteenth modification are given the same reference numerals, and they are omitted from description. A cavity maintaining tool 310 is composed of the insertion helper 287, the body 288 and the handle portion 289. In particular, the leg portions 294 of the bases 290 of the body 288 are provided with a groove portion 311 and a hole portion 292a of the endoscope guide tube 292. The insertion helper 287, the body 288 and the handle portion 289 of the cavity maintaining tool 310 are assembled and secured similarly to the foregoing method. By inserting the body 288 along the subject tissue and by removing the insertion helper 287 and the handle portion 289, the body 288 is able to maintain a satisfactory large cavity. Since the body 288 has the frame structure, the treatment tool can be inserted through the lateral holes 205 in the side surface simultaneously with the insertion of the endoscope through the hole portion 292a of the endoscope guide tube 292. Thus, the operation can be performed further smoothly. Since the groove portion 311 is formed in the base 290, the treatment tool can further smoothly be inserted through the groove portion 311.

Figure 62C:
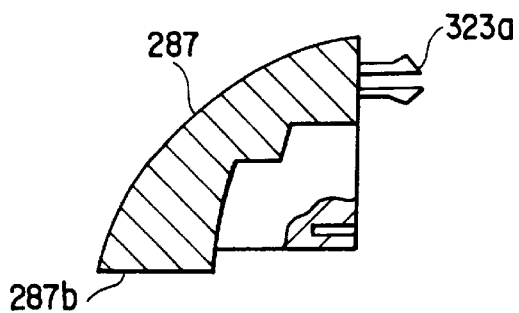
FIG. 62C shows a first example of a connection means for connecting an insertion helper and the body, forming the cavity maintaining tool according to the fifteenth modification, to each other.
Figure 62D:
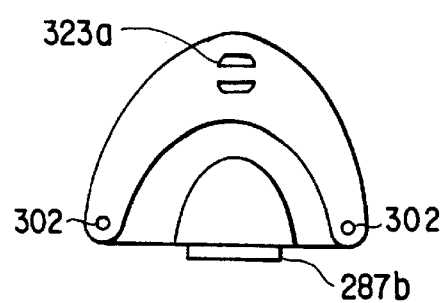
FIG. 62D is a front view showing the insertion helper shown in FIG. 62C.
Figure 62E:
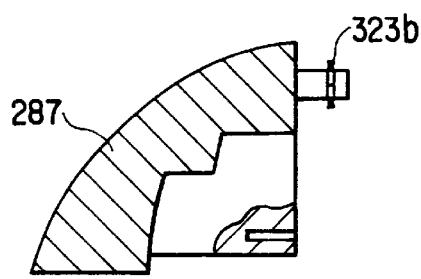
FIG. 62E shows a second example of the connection means for connecting the insertion helper and the body, forming the cavity maintaining tool according to the fifteenth modification, to each other.

FIGS. 62A to 62G show a fifteenth modification of the cavity maintaining tool. The same elements as those of the thirteenth modification are given the same reference numerals and they are omitted from the description. A cavity maintaining tool 320 is composed of the insertion helper 287 and the body 288. Each of bases 321 formed in the front and rear portions of the body 288 is in the form of an H-shape having large groove portions 322 in the right and left side portions, as shown in FIGS. 62A and 62B. The insertion helper 287 has a guide projection 287b. Moreover, an elastic member 323 serving as a connection member so as to be engaged and secured to the body 288 is formed to project over the rear end of the insertion helper 287. The elastic member 323 may be, for example, an engaging claw as shown in FIG. 62C, an O-ring 323b as shown in FIG. 62D or a C-ring 323c as shown in FIG. 62E. The elastic member 323 is inserted into a hole portion 292a in the front portion of the endoscope guide tube 292 of the body 288 so as to secure the insertion helper 287 and the body 288.

Figure 62F:
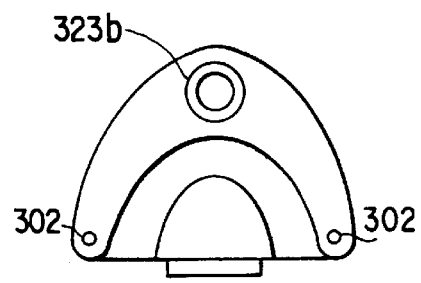
FIG. 62F is a front view showing the insertion helper shown in FIG. 62E.
Figure 62G:
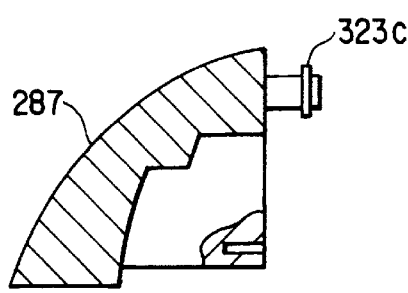
FIG. 62G shows a third example of the connection means for connecting the insertion helper and the body, forming the cavity maintaining tool according to the fifteenth modification, to each other.
Figure 62H:
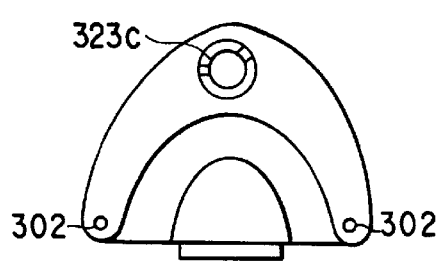
FIG. 62H is a front view showing the insertion helper shown in FIG. 62G.
Figure 62I:
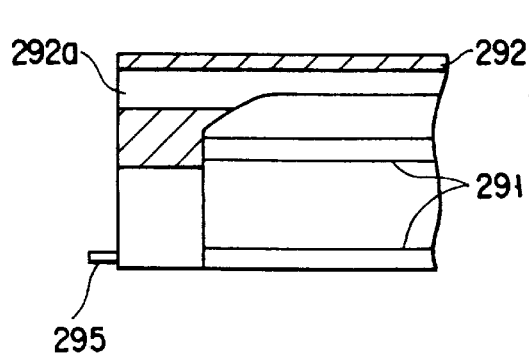
FIG. 62I shows a first example of an opening of an endoscope guide tube provided for the body of the cavity maintaining tool according to the fifteenth modification.
Figure 62J:
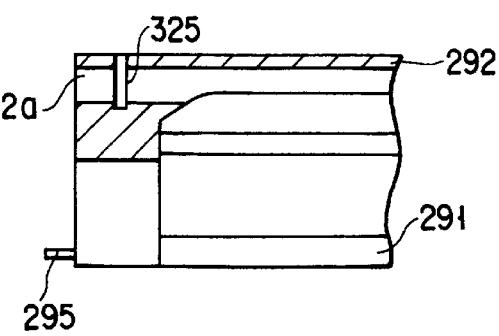
FIG. 62J shows a second example of the opening of the endoscope guide tube provided for the body of the cavity maintaining tool according to the fifteenth modification.

The front hole portion 292a of the endoscope guide tube 292 is formed into a cylindrical shape having no groove as shown in FIG. 62F or provided with a groove 325 capable of satisfactorily receiving the projection shape of the elastic member 323. The locating member 295 of the body 288 of the cavity maintaining tool 320 is received by and engaged to the locating hole 302 of the insertion helper 287 and the elastic member 323 of the insertion helper 287 is inserted into the front hole portion 292a of the endoscope guide tube 292. Thus, the body 288 and the insertion helper 287 can be assembled as shown in FIG. 62A. As a result, insertion to the position below the skin can be performed along the subject tissue. Since the insertion helper 287 can easily be removed from the body 288 by a single action, the body 288 is able to maintain a satisfactorily large cavity under the skin. Since the frame structure is formed, when the endoscope has been inserted by the endoscope guide tube 292, the treatment tool can simultaneously be inserted. Thus, the operation can further smoothly be performed. Since the structure is different from the thirteenth modification such that the base is formed into the H-shape and the groove portion 322 is formed, the treatment tool can further smoothly be inserted.

FIGS. 63A and 63B show sixteenth modification of the cavity maintaining tool. The same elements as those of the thirteenth modification are given the same reference numerals and they are omitted from the description. A cavity maintaining tool 330 is composed of an insertion helper 287, a body 288 and a handle portion 289. An air suction pipe 331 is arranged between front and rear bases 332 of the body 288 individually from the endoscope guide tube 292 and the shafts 291. The air suction pipe 331 is disposed at a relatively upper position to run parallel to the endoscope guide tube 292 and the shafts 291 while being apart from the same. The air suction pipe 331 has a multiplicity of suction holes 331a in the wall thereof. The front and rear bases 332 have grooves 334. An opening 335 is formed on the inside of the base 332.

An air suction tube 336 connected to the air suction pipe 331 is connected to the base 332. The air suction tube 336 is detachably connected. The air suction tube 336 may be connected to the rear base 332 or may be connected to either of the bases 332. Similarly to the thirteenth modification, the cavity maintaining tool 330 can be assembled such that the locating member 295 of the body 288 is received by the locating hole 302 of the insertion helper 287; and the handle portion 289 is used to connect and secure the insertion helper 287 and the body 288 to each other. The cavity maintaining tool 330 can be used similarly to the thirteenth modification. After it has been retained, air suction in the cavity can be performed through the air suction pipe 331.

According to the sixteenth modification, insertion to the position below the skin along the subject tissue can be performed. By removing the insertion helper 287 and the male thread portion 298, the body 288 is able to satisfactorily large cavity below the skin. Since the body 288 has the frame structure, the treatment tool can be inserted through the rear opening 335 of the body 288 and the lateral hole in the side surface simultaneously with insertion of the endoscope through the endoscope guide tube 292. Thus, the operation can further smoothly be performed. Since the groove portion 334 is formed in the base 332, the treatment tool can further smoothly be inserted. Since the air suction tube 336 is connected to the air suction pipe 331, air in the cavity can be sucked so that fogging of the visual field of the endoscope is prevented or overcome.

FIGS. 64A and 64B show a seventeenth modification of the cavity maintaining tool. This modification has common elements as those of the thirteenth to sixteenth modifications. The same elements are given the same reference numerals and they are omitted from the description. A cavity maintaining tool 340 is composed of the insertion helper 287 having the elastic member 323 and the body 288. The handle portion 289 is omitted in this modification. The shafts 291 of the body 288 also serves as the air suction pipe 331 so that the shafts 291 and the air suction pipe 331 are not provided individually. Similarly to the thirteenth modification, each of the front and rear bases 321 is formed into an H-shape to form the large groove portions 322 in the right and left outer portions. Connection ports 342 individually connected to the air suction pipe 331 also serving as the shafts 291 are formed in the bases 321. A suction tube 341 is detachably connected to either of the connection port 342. A portion or the overall portion of each air suction pipe 331 may be connected in the base 321 to connect one suction tube 341 to a plurality of the air suction pipes 331.

The cavity maintaining tool 340 is structured due to the following securing operation. The locating member 295 of the body 288 determines the position of the insertion helper 287, and the elastic member 323, which is the connection member, is inserted into the opening hole portion 292a of the body 288 so that the insertion helper 287 and the body 288 are engaged and secured to each other. Similarly to the foregoing modification, insertion along the subject tissue into a position below the skin is performed so that the body 288 is retained in the cavity. Air in the cavity can be sucked through the shafts 291 also serving as the air suction pipe 331 after the body 288 has been retained. The insertion helper 287 can easily be removed from the body 288 by a single action. Thus, the body 288 is able to maintain a satisfactorily large cavity below the skin. Since the body 288 has the frame structure, the treatment tool can be inserted through the lateral hole portion of the body 288 simultaneously with the insertion of the endoscope through the endoscope guide tube 292. Thus, the operation can further smoothly be performed. In a manner different from the thirteenth embodiment, each base 321 is formed into the H-shape to have the groove portion 322 so that the treatment tool is further smoothly inserted. By connecting the suction tube 341 to either of the shafts 291 also serving as the air suction pipe 331, air in the cavity can be sucked to prevent and overcome foregoing of the visual field of the endoscope.

Figure 65A:
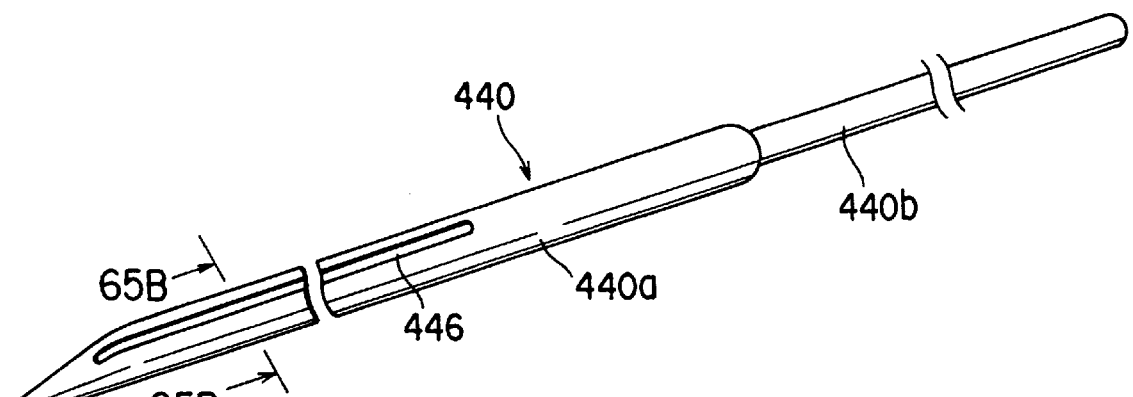
FIG. 65A is a perspective view showing a first example of a guide member for protecting the subcutaneous tissue while guiding pincers.
Figure 65B:
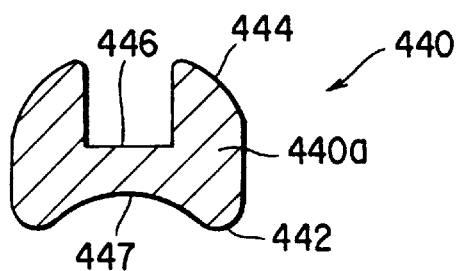
FIG. 65B is a cross sectional view taken along line 65B—65B shown in FIG. 65A.
Figure 65C:
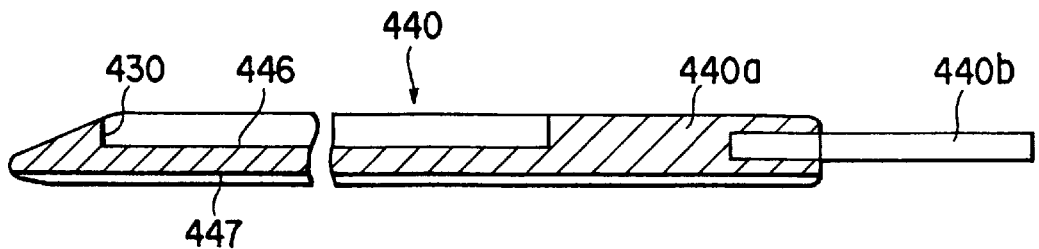
FIG. 65C is a side cross sectional view showing the guide member shown in FIG. 65A.

FIGS. 65A and 65B show a first example of a guide member for protecting the subcutaneous tissue while guiding the forceps 91 (219) according to the first embodiment and the modifications. As shown in FIG. 65A, a guide member 440 according to this example is formed into an elongated rod-like shape so as to be inserted into the subcutaneous tissue. The guide member 440 has a body 440a having a width and length with which at least a portion of the subcutaneous tissue to be protected is covered and protected. An operation rod 440b having a diameter smaller than that of the body 440a is connected to the base portion of the body 440a. As shown in FIG. 65B, the body 440a of the guide member 440 has a substantially flat cross sectional shape. A protective surface 442 of the body 440a which is brought into contact with the subcutaneous tissue to be protected has an accommodation groove 447 for accommodating and protecting the subcutaneous tissue, the accommodation groove 447 being formed for the overall length of the protective surface 442. A guide surface 444 opposite to the protective surface 442 has a guide groove 446 for guiding the treatment tool, the guide groove 446 being formed in the lengthwise direction of the guide surface 444. The two ends of the guide groove 446 are closed by walls. In particular, a groove wall 430 adjacent to the leading end restrict projection of the treatment tool toward the leading end, the treatment tool being guided along the guide groove 446. The guide groove 446 may be formed for the overall length of the body 440a. To easily insert the body 440a into the subcutaneous tissue and to easily separate the subcutaneous tissue, to be protected, from other subcutaneous tissue, the leading end of the body 440*a* is tapered in the forward direction. To protect the tissue from being damaged, the leading end portion of the body 440*a* is formed into a smooth and moderate shape.

Figure 66A:
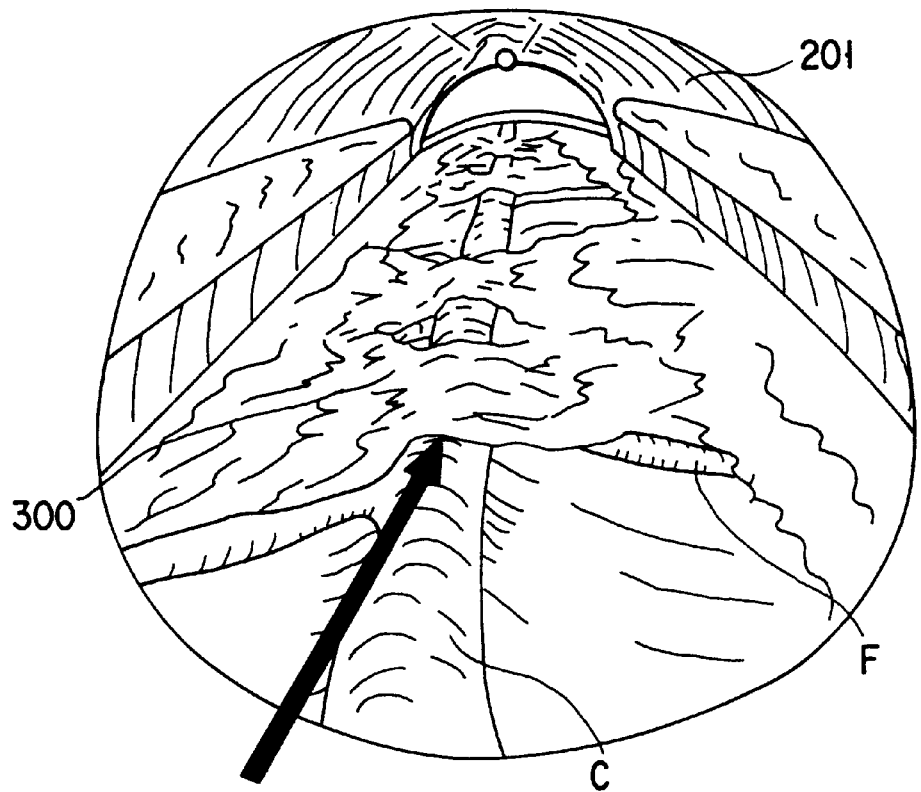
FIG. 66A is a diagram showing a state where the guide member shown in FIG. 65A has been inserted between the saphenous vein and the connective tissue.
Figure 66B:
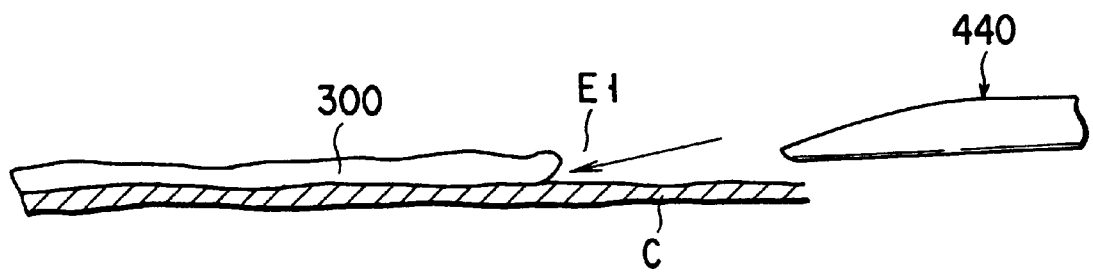

A case where an operation for extracting the saphenous vein by using the guide member 440 having the foregoing structure with the endoscope will now be described with reference to FIGS. 66A to 68B. Initially, an operation similar to the first embodiment and modifications is performed so that a cavity having a predetermined size is formed above the saphenous vein C. The cavity is maintained by the doom type cavity maintaining tool 201 shown in FIG. 29. The foregoing state is shown in FIG. 66A. In the space maintained by the cavity maintaining tool 201, the saphenous vein C is exposed while being partially covered by the connective tissue 300 on the blood vessel C. The reason for this is that the excising member 10 sometimes passes through the connective tissue 300 on the blood vessel C when the excising operation using the excising member 10 is performed. Note that symbol F represents a branch from the saphenous vein C.

In the foregoing state, an operation for excising the connective tissue 300 on the blood vessel C, which is a membrane tissue, from the saphenous vein C is required. Accordingly, the guide member 440 is introduced into the space maintained by the cavity maintaining tool 201 through the skin cut portion E1. Then, the guide member 440 is pushed forwards toward a space between the connective tissue 300 on the blood vessel C, which has not been dissected, and the saphenous vein C, as indicated by an arrow (see FIG. 66B). Note that the foregoing operation is performed through the endoscope (not shown) which has been introduced into the cavity maintaining tool 201. As shown in FIG. 67A, the guide member 440 is inserted between the connective tissue 300 on the blood vessel C, which has not been dissected, and the saphenous vein C so that the connective tissue 300 on the blood vessel C and the saphenous vein C are dissected from each other. At this time, the guide member 440 is inserted to cause the saphenous vein C to be placed along the accommodation groove 447. FIG. 67B shows the vertical cross section realized in the foregoing state. FIG. 67C shows a horizontal cross section. At this time, the blade of the forceps 91 (219) is inserted along the guide groove 446.

Figure 68A:
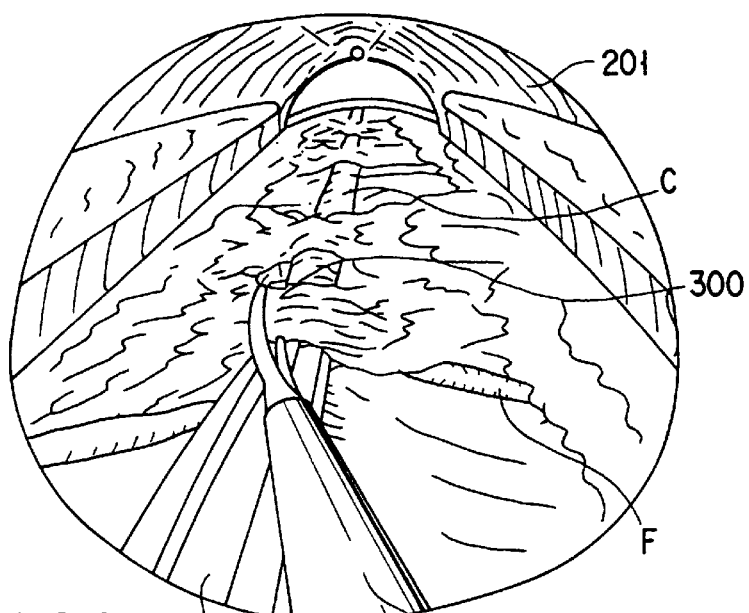
Figure 68B:
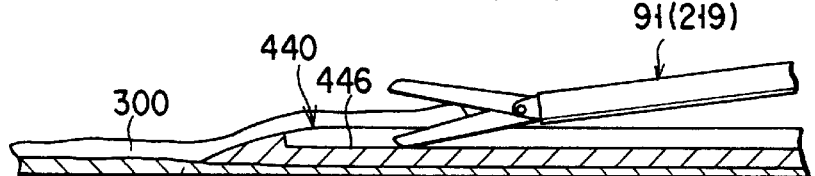

After the tissue C and 300 have been dissected to a certain extent by the guide member 440, the blades of the forceps 91 (219) are moved forwards along the guide groove 446 so as to place the connective tissue 300 on the blood vessel C between the upper blade and the lower blade, as shown in FIGS. 68A and 68B. In the foregoing state, the connective tissue 300 on the blood vessel C is cut. The foregoing operation is repeated until the overall body of the saphenous vein C is exposed.

Figure 69A:
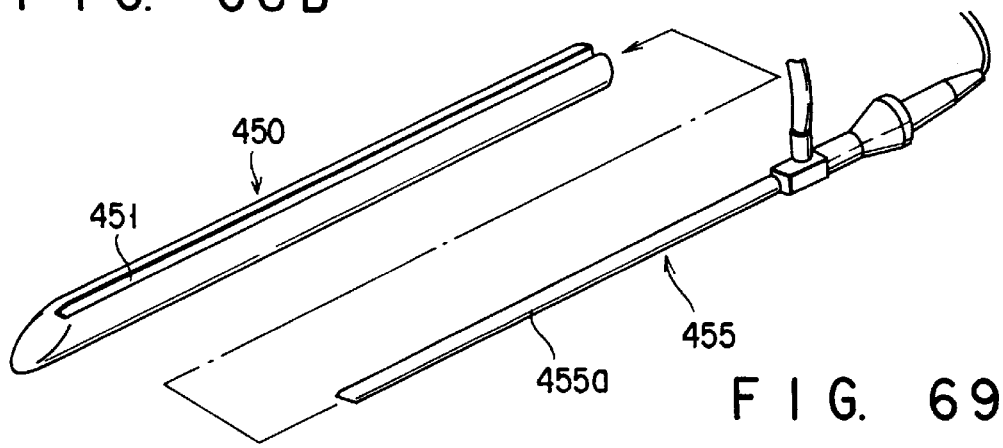
Figures 69B, 69C:
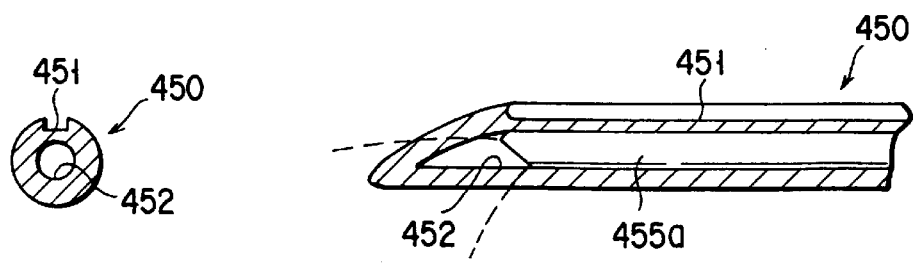

FIGS. 69A to 69C show a second example of the guide member for protecting the subcutaneous tissue while guiding the forceps 91 (219). A guide member 450 according to this example is formed into an elongated tubular member. As illustrated, the guide member 450 has a hole 452 into which an insertion portion 455*a* of the endoscope 455 can be inserted. The leading end of the hole 452 is closed, while the base portion of the hole 452 is opened. The guide member 450 is fully made of transparent material to permit observation with the endoscope 455 inserted into the hole 452. The guide member 450 has a guide groove 451 capable of guiding a treatment tool or the like, the guide groove 451 being formed for the overall length of the guide member 450. The leading end of the guide member 450 is tapered in the forward direction to be easily inserted into the subcutaneous tissue and to easily dissect the subcutaneous tissue, to be protected, from the other subcutaneous tissue. To protect the tissue from being damaged, the leading portion of the guide member 450 is formed into a smooth and moderate shape.

The guide member 450 having the foregoing structure enables treatment to be performed in such a manner that the insertion portion 455*a* of the endoscope 455 is inserted into the hole 452 through the opening in the base portion to observe the portion to be treated. For example, while guiding the forceps along the guide groove 451 and performing treatment, the state can be observed through the endoscope 455. Since the guide member 450 prevent contact between the treatment tool and the subcutaneous tissue to be protected, that is, the guide member 450 protects the subcutaneous tissue positioned below the guide member 450, the subcutaneous tissue can be protected from being damaged during the operation, such as the excising operation.

FIGS. 70 to 72B show a third example of the guide member for protecting the subcutaneous tissue while guiding the forceps 91 (219). As shown in FIG. 70, a guide member 460 according to this example is formed into an elongated tubular member. As illustrated, the guide member 460 has a hole 462 into which a treatment tool 465, such as forceps, can be inserted. The leading end of the hole 462 is closed, while the base portion of the hole 462 is opened. The opening 461 has a size with which interference with, for example, interference of the movement of a forceps portion 466 of the treatment tool 465 is prevented. The leading end of the guide member 460 is tapered in the forward direction to be easily inserted into the subcutaneous tissue and to easily dissect the subcutaneous tissue, to be protected, from the other subcutaneous tissue. To protect the tissue from being damaged, the leading portion of the guide member 460 is formed into a smooth and moderate shape.

When the guide member 460 having the foregoing structure is used, for example, the treatment tool 465 is inserted into the hole 462 through the opening in the base portion of the guide member 460 so that the forceps portion 466 is placed in the opening 461, as shown in FIGS. 71A to 71C. As shown in FIGS. 72A and 72B, the guide member 460 is inserted between, for example, the saphenous vein C and the connective tissue 300 on the blood vessel C to perform excision in a state where a pair of blades 466*a* and 466*b* are opened. After the excision has been performed to a certain extent, the connective tissue 300 on the blood vessel C is cut by the blades 466*a* and 466*b*. As described above, the guide member 460 according to the third example has the arrangement such that the treatment tool 465 is accommodated in the hole 462 and only the forceps portion 466 directly relating to the treatment is exposed through the opening 461. Therefore, contact between the tissue, to be protected, and the treatment tool 465 can reliably be prevented as compared with the case where the treatment tool is guided along the guide groove.

FIGS. 73 and 74 show a second modification of the excising member. The excising member according to the second modification has the functions of the excising member 10 and the cavity forming tool 50 according to the first embodiment. As shown in FIG. 73, an excising member 500 according to this modification has a pipe member 514, which is an insertion portion, a leading end 526 formed at the leading end of the pipe member 514 and made of a transparent resin material and a rear end member 522 formed at the base portion of the pipe member 514. A balloon 516 is attached to the pipe member 514 to cover the overall length of the pipe member 514. The balloon 516 has securing regions 518 formed at the leading end and the trailing end thereof with which the balloon 516 is closed secured to the pipe member 514. Note that the other portions of the balloon 516 are not secured to the pipe member 514. An outer sheath 512 is attached on the outside of the balloon 516 to be detachable with respect to the excising member 500. As a result, the balloon 516 is, in a contracted state, accommodated in the outer sheath 512. The outer diameter of the outer sheath 512 is made to be smaller than that of the leading end 526 of the excising member 500. The base portion of the outer sheath 512 is screwed in the thread portion 520 of the rear end member 522 in such a manner that the outer sheath 512 covers from the rear end portion of the excising member 500 so that the outer sheath 512 is attached and secured to the excising member 500. In the foregoing case, the leading end of the outer sheath 512 is engaged to a rear end portion 526a of the leading end 526 having an outer diameter somewhat smaller than the inner diameter of the outer sheath 512.

As the material of the balloon 516, an extension material, such as silicon rubber and latex, for use as a balloon for an endoscope; or a non-extension material, such as polyethylene terephthalate, polyamide or olefin plastic, for use as a balloon dilator. In the foregoing case, the balloon 516 is previously formed into a required shape and folded and accommodated in the outer sheath 512.

The pipe member 514 of the excising member 500 is provided with one or more communication holes 510 communicated with the inside portion of the balloon 516. The rear end member 522 of the excising member 500 has, similarly to the excising member 10 shown in FIGS. 4A and 4B, an L-shape slit 13a capable of hooking the tissue protective tool 30 shown in FIG. 7A and a rotation-stopping groove 17 to which the control pin 87 of the sheath holder 110 shown in FIGS. 5A and 5B is engaged.

When the balloon 516 is expanded, the outer sheath 512 is removed from the excising member 500, and then an inflation adapter 532 is, as shown in FIG. 74, connected to the rear end member 522 of the excising member 500. In this case, the inflation adapter 532 is screwed in the thread portion 520 of the rear end member 522. An O-ring 530 for keeping air tightness is interposed between the inflation adapter 532 and the rear end member 522. Then, a fluid supply means, such as a syringe (not shown) is connected to a Luer mouth piece 532a at the base portion of the inflation adapter 532. In this state, for example, air is supplied to the inner space of the excising member 500 from the fluid supply means. Supplied air is introduced into the balloon 516 through the communication hole 510 of the pipe member 514 to expand the balloon 516. Therefore, the excising member 500 having the foregoing structure is able to expand the excision cavity and form a working space permitting treatment to be performed as well as excising the subcutaneous tissue without excessive force for the tissue by expanding the balloon 516.

FIG. 75 shows another structure for expanding the cavity by the balloon 516. As illustrated, the folded balloon 516 is accommodated in a balloon cover 545. The outer diameter of the balloon cover 545 is made to be smaller than the maximum outer diameter of the excising member 10 shown in FIGS. 4A and 4B. An engaging groove 540 capable of engaging to the L-shape slit 13a of the excising member 10 is formed in the leading end of the balloon cover 545.

To expand the balloon 516, the engaging groove 540 of the balloon cover 545 is hooked by the L-shape slit 13a at the rear end of the excising member 10 inserted and retained below the skin. In this state, the balloon cover 545 is inserted into the position below the skin while performing traction of the excising member 10. After the balloon cover 545 has been completely inserted below the skin, only the balloon cover 545 is removed from the position below the skin while holding the rear end of the balloon 516 exposing to the outside through the skin cut portion. In this state, air is supplied to the balloon 516 through the air tube 546 so that the balloon 516 retained in the position below the skin is expanded. Thus, the subcutaneous tissue is dissected and the excision cavity can be expanded.

The first embodiment is considerably low invasive as compared with the related art described at the beginning of the specification. However, the skin is inevitably cut for about 4 cmand an excision cavity having a similar size must be formed below the skin. Thus, according to a second embodiment, to be described below, there is provided a system for evulsing subcutaneous tissue which is lower invasive as compared with the first embodiment.

When the blood vessel is evulsed in the second embodiment, for example, when the blood vessel in the lower extremity is evulsed, the skin cut portion E1 is, by a knife or the like, formed in the inguinal region A of the thigh at a position just above the blood vessel C, such as the saphenous vein, intended to be extracted and extending from the inguinal region A of the thigh to the knee D, similarly to the first embodiment and as shown in FIG. 1. In the skin cut portion E1, the blood vessel C is exposed by forceps or the like. Then, the tissue just above the blood vessel C is dissected by a similar forceps or the like for a distance which can be observed by the naked eye through the skin cut portion E1.

Then, the hard endoscope 20 is inserted and secured to the excising member 10 (refer to FIGS. 4A and 4B) according to the first embodiment. In the forgoing insertion and secured state, the leading end 12 of the excising member 10 is inserted through the skin cut portion E1 in the inguinal region A toward the knee D to move along the upper portion of the blood vessel C (see FIGS. 6A and 6B). Since the leading end 12 of the excising member 10 is made of a transparent material, the blood vessel C and the branch F can be observation clearly by the hard endoscope 20. The insertion of the excising member 10 is gradually performed in such a manner that the excising member 10 is moved forwards and rearwards for a short distance while observing the movement of the blood vessel C through the hard endoscope 20. When the excising member 10 has been inserted along the blood vessel C to a position near the knee D, the skin just above the leading end 12 of the excising member 10 is slightly cut. Then, the leading end 12 of the excising member 10 is ejected through the skin cut portion E2.

Then, while leaving the excising member 10 in the body, the hard endoscope 20 is drawn from the excising member 10, and then a tissue protective tool 30 is attached to the side portion of the excising member 10 adjacent to the operator, which is positioned near the skin cut portion E1 in the inguinal region A. Then, the excising member 10 is pulled out through the skin cut portion skin cut portion E2, and the tissue protective tool 30 is introduced into the cavity G dissected by the excising member 10. Note that the tissue protective tool 30 can be inserted without a heavy load because the widthwise cross sectional area of the tissue protective tool 30 is substantially the same as the widthwise cross sectional area of the excising member 10. The tissue protective tool 30 is separated from the excising member 10 after the end portion of the excising member 10 adjacent to the operator's hand has been pulled out through the skin cut portion E2, the tissue protective tool 30 being then retained in the cavity G (see FIG. 9).

Then, as shown in FIG. 76, the excising member 10 to which the hard endoscope 20 is again attached, is inserted through the skin cut portion E1 along the groove 30a in the upper surface of the tissue protective tool 30 to be allowed to penetrate to reach the skin cut portion E2, followed by being pulled out. Thus, the cavity G is slightly expanded. Then, a second dissector 10A shown in FIG. 77 is inserted through the skin cut portion E1 to the skin cut portion E2 along the groove 30a in the upper surface of the tissue protective tool 30, followed by pulling out the second dissector 10A. The leading portion 12A of the second dissector 10A has the widthwise cross sectional area larger than that of the leading end 12 of the excising member 10, as shown in FIG. 78. That is to say, the circumferential length of the leading end portion 12A is longer than the circumferential length of the leading portion 12. The leading portion 12A is made of a transparent material and having a shape like the leading end 12 of the excising member 10. Therefore, when the second dissector 10A has been inserted through the skin cut portion E1 and allowed to penetrate to reach the skin cut portion E2, followed by pulling out the second dissector 10A, the dissected cavity G is further expanded to a size into which the cavity maintaining tool 60A can be inserted. That is to say, the second dissector 10A serves as the cavity forming tool.

FIG. 79 shows a cavity maintaining tool 672 according to this embodiment. As illustrated, the cavity maintaining tool 672 is composed of an outer tube 672A, and two inner tubes 672B and 672C which can be inserted into the outer tube 672A. The outer tube 672A is formed into a cylindrical shape having two opened ends. The outer tube 672A has a cut having a predetermined depth for, substantially, the overall length except the two ends thereof. Thus, a side port 673 opened side is formed. It is preferable that the outer diameter of the outer tube 672A is about 10 mm to about 20 mm. The hard endoscope 20 can be inserted into the first inner tube 672B of the cavity maintaining tool 672. The hard endoscope 20 is secured to the inner tube 672B by a fixing screw 674 disposed in the portion of the inner tube 672B adjacent to the operator in a state where the hard endoscope 20 has been inserted into the inner tube 672B. A treatment tool for treating the blood vessel C and to be described later can be inserted the inner tube 672C of the cavity maintaining tool 672. To protect the tissue from being damaged, the portions of the two openings of the outer tube 672A and inner tubes 672B and 672C have no edges.

FIG. 80 shows an insertion helper 675 detachably attached to the outer tube 672A to guide and facilitate insertion of the outer tube 672A. As illustrated, the insertion helper 675 is composed of a leading portion 675a having a tapered leading end; and a support portion 675b detachably attached to the leading portion 675a by means of threads. The support portion 675b is composed of an elongated 676 and a near-side portion 677 formed in the end portion of the shaft portion 676. A state where the insertion helper 675 is attached to the outer tube 672A is shown in FIG. 81. The procedure will now be described. For example, the shaft portion 676 of the insertion helper 675 is inserted into the outer tube 672A, and then the leading portion 675a is screwed in the thread portion of the shaft portion 676 projecting through an opening of the outer tube 672A in a state where the near-side portion 677 is brought into contact with the end surface of each opening of the outer tube 672A.

Then, the end surface of the leading portion 675a adjacent to the operator is brought into the end surface of the other opening of the outer tube 672A. As a result, the contact state of the leading portion 675a is maintained by the support portion 675b so that the insertion helper 675 is attached to the outer tube 672A while holding the outer tube 672A. The outer tube outer tube 672A, to which the insertion helper 675 has been attached, is inserted and retained in the cavity G expanded by the second dissector 10A. When the outer tube 672A is inserted into the internal cavity G under the skin, the leading portion 675a of the insertion helper 675 attached to the outer tube 672A is, along the groove 30a of the tissue protective tool 30, inserted and allowed to penetrate from the skin cut portion E1 to the skin cut portion E2. Then, the insertion helper 675 is removed from the outer tube 672A after the penetration. The foregoing state is shown in FIG. 82.

After the foregoing operation has been completed, the first and second inner tubes 672B and 672C are inserted into the outer tube 672A. Then, the tissue protective tool 30 is pulled out from the cavity G. The foregoing state is shown in FIG. 83. The cross sections of the foregoing state are shown in FIGS. 84A to 84C. As shown in FIGS. 84A to 84C, in the state where the cavity maintaining tool 672 is retained under the skin along the blood vessel C, the tissue is raised (forcibly moved) by the outer tube 672A, and the blood vessel C and the connective tissue 300 on the blood vessel C are pushed downwards (forcibly moved) by the first and second inner tubes 672B and 672C. Thus, a treatment space (cavity) G for separating the blood vessel C from the connective tissue 300 on the blood vessel C is maintained.

In the states shown in FIGS. 84A to 84C, the hard endoscope 20 is inserted into the inner tube 672B, as shown in FIG. 85A. To obtain excellent visual field for the hard endoscope 20, it is preferable that the leading end of the hard endoscope 20 is positioned near the leading end of the first inner tube 672B in a state where the objective lens of the hard endoscope 20 is not in contact with the tissue. That is, it is preferable that the length of the first inner tube 672B is set to permit the hard endoscope 20 to be inserted and secured to the first inner tube 672B in the foregoing state. An image picked up by the hard endoscope 20 in the foregoing preferred state is shown in FIG. 85B. As illustrated, the blood vessel C and the branch F can be clearly observed. Moreover, the second inner tube 672C can be observed at a distant position.

By moving the first inner tube 672B in the outer tube 672A in the state shown in FIG. 85A, a cavity G under the skin from the skin cut portion E1 to the skin cut portion E2 can be observed. By changing the distance from the first inner tube 672B to the second inner tube inner tube 672C, the size of the treatment (cavity) G can be adjusted. FIG. 86A shows a state where the opening/closing type hook probe 130 shown in FIG. 20 has been inserted into the treatment (cavity) G through the second inner tube 672C to dissect the blood vessel C from the connective tissue 300 on the blood vessel C. An image picked up by the hard endoscope 20 at this time is shown in FIG. 86B. As can be understood from FIG. 86B, movement of the opening/closing type hook probe 130 to the right results in the opening/closing type hook probe 130 being moved to the left in the image picked up by the endoscope 20 because the opening/closing type hook probe 130 and the hard endoscope 20 are inserted from the opposite positions of the outer tube 672A. Therefore, the opening/closing type hook probe 130 cannot easily be operated.

Accordingly, this embodiment uses an endoscope system 700 shown in FIG. 87. In the endoscope system 700, an image picked up by the hard endoscope 20 is, through a video adapter 701 having an optical system bent perpendicularly, transmitted to a TV camera 702 including an image pickup device (not shown) so that the optical signal is converted into an electric signal and then transmitted to a CCU (Camera Control Unit) 703. A signal from the CCU 703 is transmitted to an image inverting unit 704 so as to be converted into an image, the right-hand portion and the left-hand portion are inverted, followed by being transmitted to the monitor 705. Therefore, the operator is able to observe an image which coincides with the direction of the actual movement of the treatment tool.

In the case where the blood vessel C is dissected from the connective tissue 300 by the opening/closing type hook probe 130, the front hooks 135 and 136 of the opening/closing type hook probe 130 are closed while observing the image which coincides with the actual movement of the treatment tool. In the foregoing state, the leading hooks 135 and 136 are inserted into the surrounding tissue 300, followed by moving under the blood vessel C to penetrate to reach the opposite portion (see FIG. 86B). In the foregoing state, the hooks 135 and 136 are gradually opened so as to dissect the blood vessel C from the surrounding tissue 300. The state where the blood vessel C has been dissected from the surrounding tissue 300 is shown in FIG. 88A. The foregoing operation is performed for the length of the blood vessel C intended to be evulsed. In this case, an excising forceps for a body cavity mirror (not shown) may be used, if necessary.

After the blood vessel C has been dissected for the length to be evulsed (for example, about 25 cm), clips 96 are attached to two portions of the branch F (see FIG. 88B), and then the branch F between the clips 96 is cut by the forceps (see FIG. 88C). The operation of cutting the branch F is performed for the length of the blood vessel C intended to be evulsed so that the blood vessel C is evulsed to the outside of the body. If a longer blood vessel is required to be evulsed, a similar operation is required to be performed repeatedly. In this case, the blood vessel C from the inguinal region A to the ankle can be evulsed.

As described above, according to this embodiment, the blood vessel can easily be evulsed from a very small skin cut portion without damage of the blood vessel. This embodiment enables nerve below the skin to be evulsed, as well as the blood vessel.

FIGS. 89, 90A and 90B show a first modification of the second embodiment. The first modification is deformation of the cavity maintaining tool 672 according to the second embodiment. The residual structures and operation are the same as those of the second embodiment. As shown in FIG. 89, the cavity maintaining tool 680 according to this modification is formed into a cylindrical shape. The side surface of the central portion of the cavity maintaining tool 680 is cut to have a predetermined depth. Thus, a side port 681 opened in the side portion to form the treatment space (cavity) G is formed. The method of inserting and retaining the cavity maintaining tool 680 in the cavity under the skin and the endoscope system for obtaining an inverted image are the same as those according to the second embodiment.

FIG. 90A shows a state where the cavity maintaining tool 680 is retained in the cavity under the skin. FIG. 90B shows an image picked up by the hard endoscope 20 inserted into the cavity maintaining tool 680. By moving the side port 681 of the cavity maintaining tool 680 from skin cut portion E1 to skin cut portion E2, the overall body of the blood vessel C can be observed and treated. Note that the method of separating the blood vessel C from the surrounding tissue 300 is the same as that according to the second embodiment.

FIGS. 91A and 91B show a second modification of the second embodiment. This modification is a modification of the cavity maintaining tool 680 according to the first modification. The other structures and operations are the same as those of the first modification. As illustrated, a cavity maintaining tool 690 according to this modification is compose of a cylindrical body 690a and extension portions 690b respectively detachable to the two ends of the body 690a by screws. The side surface of the central of the body 690a is cut to have a predetermined depth so that a side port 691 opened to the side portion so as to form the treatment space (cavity) G is formed. Therefore, the cavity maintaining tool 690 according to this modification has a similar shape as the cavity maintaining tool 680 according to the first modification in a state where the body 690a and the extension portions 690b.

The cavity maintaining tool 680 according to the first modification has a relatively long overall length, while the cavity maintaining tool 690 according to the second modification is enabled to have the overall length which can be adjusted to correspond to the length of the treatment region due to employment of a separation type structure. Thus, the operation can smoothly be performed. If a plurality of extension portions 690b having various lengths are prepared, they can selectively be employed having an optimum length to be adaptable to the length of the employed treatment tool. Thus, the operation can further smoothly be performed.

FIGS. 92 to 99B show a third modification of the second embodiment. This modification is a modification of the cavity maintaining tool 672 according to the second embodiment. Therefore, the same element as those according to the second embodiment are given the same reference numerals and they are omitted from illustration. As shown in FIG. 92, an outer tube 672A of a cavity maintaining tool 672' according to this modification has cut portions 810 in the cylindrical portions 801 at the two ends across the side port 673. The cut portions 810 are formed for the overall length of the cylindrical portions 801. As shown in FIG. 93, a projection 804 having a recess 803 in the central portion thereof is formed in the leading end of each of the first and second inner tubes 672B and 672C. FIG. 94 shows a state where the insertion helper 675 shown in FIG. 80 is attached to the outer tube 672A of the cavity maintaining tool 672'. FIG. 95 shows a state where the leading portion 675a of the insertion helper 675 has been inserted along the groove 30a of the tissue protective tool 30 to penetrate from skin cut portion E1 to skin cut portion E2, and then the insertion helper 675 has been removed from the outer tube 672A. FIG. 96 shows a state where the first inner tube 672B and the second inner tube 672C of the cavity maintaining tool 672' according to this modification have been inserted into the outer tube 672A in the state shown in FIG. 95 and the tissue protective tool 30 has been pulled out from the cavity G. Cross sectional views in the foregoing state are shown in FIGS. 97A to 97C. In this embodiment, insertion of the first and second inner tubes 672B and 672C of the cavity maintaining tool 672' according to this modification into the outer tube 672A is performed in a state where the projections 804 of the first and second inner tubes 672B and 672C have been inserted into cut portions 810 of the outer tube 672A. In the foregoing case, the recess 803 of the projection 804 is moved along the blood vessel C. As shown in FIGS. 97A to 97C, in a state where the cavity maintaining tool 672' is retained under the skin along the blood vessel C, the tissue is slightly raised (forcibly moved) by the outer tube 672A and the blood vessel C and the surrounding tissue 300 are pushed downwards (forcibly moved) by the first and second inner tubes 672B and 672C. As a result, a treatment space (cavity) G permitting treatment for separating the blood vessel C from the surrounding tissue 300 is maintained. In particular, the projections 804 of the first and second inner tubes 672B and 672C hold the two ends (tissue on the two sides) of the blood vessel C at the central recesses 803.

A state where the hard endoscope 20 has been inserted into the first inner tube 672B in the state shown in FIGS. 97A to 97C is shown in FIG. 98A. An image picked by the hard endoscope 20 at this time is shown in FIG. 98B. FIG. 99A shows a state where the opening/closing type hook probe 130 shown in FIG. 20 has been inserted into a treatment space (cavity) G through the second inner tube 672C to dissect the blood vessel C from the surrounding tissue 300. An image picked up by the endoscope 20 at this time is shown in FIG. 99B. As can be understood from FIG. 99B, since the recess 803 of the projection 804 of the first and second first inner tubes 672B and 672C hold two ends (tissue on the two sides) of the blood vessel C, the blood vessel C is allowed to project over the surrounding tissue. Thus, the leading hooks 135 and 136 can easily be introduced into the surrounding tissue 300 to move under the blood vessel C.

FIGS. 100, 101A and 101B show a fourth modification of the second embodiment. A cavity maintaining tool 680' according to this modification has recess portions 820 in the lower portion adjacent to the side port 681 of the cavity maintaining tool 680 according to the first modification to be place along the blood vessel C and to raise the blood vessel C from the surrounding tissue. The residual structures and operations are the same as those of the first modification.

FIGS. 102A and 102B show a fifth modification of the second embodiment. A cavity maintaining tool 690' according to this modification has recess portions 820 in the lower portion adjacent to the side port 681 of the cavity maintaining tool 680 according to the first modification to be place along the blood vessel C and to raise the blood vessel C from the surrounding tissue. The residual structures and operations are the same as those of the first modification.

FIGS. 103A, 103B, 104A and 104B show a modification of the excising member 10 and the sheath holder 110 according to the first embodiment. As shown in FIGS. 103A and 103B, the rotation-stopping groove 17 to be engaged to the control pin 87 of the sheath holder 110B shown in FIGS. 104A and 104B is disposed in the lower portion of the base portion of the large-diameter pipe 13 of the excising member 10B. Therefore, when the excising member 10B has been attached to the hard endoscope 20, the position of the excising member 10 in the direction of rotation can automatically be determined. Moreover, the large-diameter pipe 13 has the slit 13a for hooking the tissue protective tool 30 shown in FIG. 7A. A state where the sheath holder 110B and the excising member 10B have been attached to the hard endoscope 20 is shown in FIGS. 104A and 104B. The attaching method in this case is the same as that according to the first embodiment.

FIGS. 105A to 105C show a modification of the cavity maintaining tool 60 according to the first embodiment. As illustrated, the rear end 61a of the cavity maintaining tool 60 has the openings 62a and the arch-shape bases 62c having an opening 62b for an endoscope, into which the hard endoscope 20 is inserted. The leading end 61b has a leading end 62d in the form obtained by dividing a conical cylinder in the radial direction. A guide projection 60a is formed in the lower surface of the leading portion 62d so as to be received by the groove 30a of the tissue protective tool 30. Four hard shafts 62e and the endoscope guide tube 62f which can be inserted into the hard endoscope 20 are disposed between the bases 62c and the leading portion 62d. Therefore, a side opening 62g is formed for the overall length of the cavity maintaining tool 60 by the shafts 62e, the base 62c and the leading portion 62d.

FIGS. 106 to 113 show an endoscope hood serving as an excising member adaptable to the system for evulsing subcutaneous tissue according to the present invention. FIGS. 106 to 107E show a first embodiment of the endoscope hood. FIG. 106 shows a schematic structure of a sheath 901 having a transparent hood, which is the endoscope hood according to this embodiment and a hard endoscope 902 to be inserted into the sheath 901. The sheath 901 having a transparent hood has a double cylinder consisting of an inner cylinder 903 and an outer cylinder 904 disposed around the inner cylinder 903. The inner cylinder 903 is made to be longer the outer cylinder 904. The two ends of the inner cylinder 903 extend to the outsides of the two ends of the outer cylinder 904. The inner cylinder 903 has, at the leading end thereof, a transparent hood (body) 905, while the inner cylinder 903 has, at the rear end thereof, an endoscope fixing portion 906. The inner diameter of the inner cylinder 903 is determined to permit the endoscope 902 to be inserted. The transparent hood 905 has a fixed hood 907 to be secured to the leading end of the inner cylinder 903 and having a cylindrical shape and a movable hood 908. The fixed hood 907 and the movable hood 908 are made of transparent material (light transmissive material), such as a resin, such as acrylic resin, polycarbonate or polysulfone; or glass. In a state where the hard endoscope 902 has been inserted into the inner cylinder 903, an image can be observed with the hard endoscope 902 through the wall of the transparent hood 905.

The cylindrical fixed hood 907 has a cut portion 909 in the lower portion of the leading end thereof. The movable hood 908 has an engaging portion 910 having a shape corresponding to the cut portion 909 of the cylindrical fixed hood 907. The base portion of the movable hood 908 is rotatively connected to the fixed hood 907 by a hinge 911 comprising a rotational pin. A rod connection portion 912 projects over the outer surface of the movable hood 908. The leading end of the operation rod 913 for opening/closing the movable hood 908 is attached to the rod connection portion 912 by a fixing pin 914. Moreover, the base portion of the operation rod 913 is secured to the outer surface of the leading end of the outer cylinder 904.

A wedge-like pushing portion 915 is, as shown in FIG. 107A, formed at the leading end of the movable hood 908. A first electrode 917 is attached to an edge portion 916 at the leading end of the pushing portion 915. In the vicinity of the first electrode 917, a second electrode 918 is attached. The width of the first electrode 917 is smaller than the diameter of the transparent hood 905. The surface area of the first electrode 917 is smaller than that of the second electrode 918. A bipolar incising and coagulation means for incising and coagulating an organic tissue by allowing high-frequency cauterization current between the first electrode 917 and the second electrode 918 is formed.

A cord 919 connected to the two electrodes 917 and 918 is allowed to pass between the inner cylinder 903 and the outer cylinder 904, followed by being deduced to the outside through a cord insertion hole 920 formed in the outer surface at the rear end of the outer cylinder 904. Then, the cord 919 is connected to a power supply unit (not shown) for supplying the cauterization current. A flange portion 921 is, as shown in FIG. 107C, formed in the inner end portion of an engaging portion 910 of the movable hood 908 to be engaged to a cut portion 909 of the fixed hood 908. For example, a rubber member, such as silicon rubber or a sealing means 922 applied with grease or the like is provided for the flange portion 921. When the movable hood 908 is engaged in a state the cut portion 909 of the fixed hood 908 is closed, air tightness between the fixed hood 908 and the movable hood 908 can be maintained by the sealing means 922.

An inner cylinder connection portion 923 to cover the rear end of the inner cylinder 903 is provided for the endoscope fixing portion 906. A tube-like sealing member 924 is provided on the inner surface of the rear end of the inner cylinder connection portion 923. Moreover, a projection 925 is allowed to project over the outer surface of the rear end of the inner cylinder connection portion 923 in a direction perpendicular to the axial direction of the inner cylinder 903. A screw member 926 of the sealing member 924 is attached to the projection 925. After the hard endoscope 902 has been inserted into the inner cylinder 903, the screw member 926 is tightened so that the sealing member 924 is clamped and secured to the outer surface of the hard endoscope 902. Thus, the hard endoscope 902 is hermetically secured. An air supply port 927 communicated with the inner space of the inner cylinder 903 is allowed to project over the outer surface of the leading end of the inner cylinder connection portion 923. Moreover, an inner cylinder fixing portion 928 is formed at the rear end of the outer cylinder 904. The inner cylinder fixing portion 928 has an outer cylinder connection portion 929 for covering the rear end of the outer cylinder 904. A tubular sealing member 930 made of rubber or the like is provided on the inner surface of the rear end of the outer cylinder connection portion 929. A projection 931 is allowed to project over the outer surface of the rear end of the inner cylinder fixing portion 928 in a direction perpendicular to the axial direction of the outer cylinder 904. A screw member 932 for clamping the sealing member 930 is attached to the projection 931. After the inner cylinder 903 has been inserted into the outer cylinder 904, the screw member 932 is clamped so that the sealing member 930 is clamped and secured to the outer surface of the inner cylinder 903 so that the inner cylinder 903 is hermetically secured. By rotating the screw member 932 in a direction opposite to the clamping direction to loosen clamping of the sealing member 930 to the outer surface of the inner cylinder 903, the sealing member 930 of the outer cylinder 904 can be slid along the inner cylinder 903. As a result, the position at which the outer cylinder 904 is fixed to the inner cylinder 903 can arbitrarily adjusted in the axial direction of the inner cylinder 903. A conical airtight member 933 is formed on the outer surface of the outer cylinder 904. An annular sealing member 934 capable of hermetically sliding on the outer surface of the outer cylinder 904 is disposed at the rear end of the airtight member 933. The sealing member 934 is secured to the rear end of the airtight member 933 in a state where it is held between a fixing member 935, to be screw-fixed to the rear end of the airtight member 933, and the airtight member 933. Moreover, a pair of suture receiving portions 936 are formed on the outer surface of the rear end of the airtight member 933.

The operation of the foregoing structure will now be described. A procedure will now be described in which the hard endoscope 902 is, from the skin of a patient, inserted into organic tissue X in the body through the muscular tunics to observe and treat the spine, as shown in FIGS. 107B and 107C. Initially, the hard endoscope 902 is inserted into the sheath 901 having a transparent hood, and then the screw member 926 is clamped and secured. Then, a small cut portion, that is, a skin cut portion, having a size which permits the sheath 901 having a transparent hood to be inserted, is formed in the skin of the patient so as to expose the muscular tunics in the body. In this state, the sheath 901 having a transparent hood is pushed in while aligning the edge portion 916 of the transparent hood 905 through the cut portion in the skin of the patient, the muscular tissue is dissected. Thus, as shown in FIG. 107B, the leading end of the sheath 901 having a transparent hood is inserted into the organic tissue X in the body. Since the state of the organic tissue X can be observed at this time through the transparent wall of the transparent hood 905 with the hard endoscope 902 in the sheath 901, the excision operation can be performed safely while confirming the position of the blood vessel and the like. FIG. 107D shows an image of the organic tissue X observed through the transparent wall of the transparent hood 905 with the hard endoscope 902 during the operation of inserting the sheath 901 having a transparent hood.

If the leading end of the transparent hood 905 comes in contact with the fasciae or hard tissue during the operation of inserting the leading end of the sheath 901 having a transparent hood, the high-frequency cauterization current is allowed to flow through the first electrode 917 and the second electrode 918. The current is allowed to flow by the bipolar method to the first and second electrodes 917 and 918. Since the current is allowed to flow through the two electrodes 917 and 918, the operation can be performed safely. Since the surface area of the first electrode 917 is smaller than that of the second electrode 918, density of the current per unit area is raised. Therefore, the organic tissue X can be cauterized concentrically in the portion adjacent to the first electrode 917. Thus, the organic tissue X can be incised and coagulated so that even the fasciae and hard organic tissue are dissected. Since the first electrode 917 is disposed adjacent to the leading end of the movable hood 908 and the edge portion 916, the cauterized portion of the organic tissue X can easily be dissected by the edge portion 916. Therefore, the excising operation can further easily be performed. Since the width of the first electrode 917 is made to be smaller than the diameter of the transparent hood 905, an experiment resulted in that the wedge-like pushing portion 915 of the sheath 901 having a transparent hood having a diameter of ten-odd mm can be inserted into the body if a cut portion having a size of about 3 mm is formed in the skin of the patient in the case of the muscular tunics. Therefore, the sheath 901 having a transparent hood can be inserted into the body while necessitating a smaller incision and coagulation of the organic tissue X of the patient. Moreover, during the operation of inserting the sheath 901 having a transparent hood into the body, the state of the incision and coagulation of the organic tissue X can be confirmed with the hard endoscope 902 through the transparent wall of the transparent hood 905. Thereof, the operation can safely be performed.

Even if bleeding takes place, it can be stopped by abutting the first electrode 917 and the second electrode 918 at the leading end of the transparent hood 905 against the bleeding portion. Therefore, another tool for stopping bleeding is not required. Thus, the operation of excising the organic tissue X can smoothly be performed. In the state where the engaging portion 910 of the movable hood 908 has been engaged to the cut portion 909 of the fixed hood 907, the sealing means 922 provided for the flange portion 921 at the inner end of the engaging portion 910 of the movable hood 908 prevents introduction of blood into the transparent hood 905 through the joint portion between the fixed hood 907 and the movable hood 908. Therefore, contamination of the hard endoscope 902 in the sheath 901 having a transparent hood can be prevented. When the sheath 901 having a transparent hood has reached the spine Y, the airtight member 933 is slide along the outer surface of the outer cylinder 904 toward the leading end to bring the same into contact with the portion around the small cut portion in the skin. In the foregoing state, a suture is used to suture the skin from the suture receiving portion 936 and the skin, and then the airtight member 933 is secured to the skin.

Then, the outer cylinder 904 is moved with respect to the inner cylinder 903. At this time, the operation rod 913 is pulled rearwards due to the movement of the outer cylinder 904. Therefore, the movable hood 908 is rotated relative to the hinge 911 so that the movable hood 908 is opened downwards with respect to the fixed hood 907. In this state, $CO_2$ gas or the like is supplied into the body from the air supply port 927 of the sheath 901 having a transparent hood at a position near the operator through the inner cylinder 903. As a result, the portion, which has been dissected due to the opening of the movable hood 908, is further opened due to the supply of the gas. Thus, space S in the body required to perform the observation and treatment of the spine Y is maintained, as shown in FIG. 107C. Since the movable hood 908 has been opened downwards with respect to the fixed hood 907 at this time, the spine Y can directly be observed with the hard endoscope 902 in the sheath 901 without transmission through the transparent wall of the transparent hood 905. Therefore, a clear visual field can be obtained with the hard endoscope 902. FIG. 107E shows an image of the spine Y which has been directly observed with the hard endoscope 902 in the sheath 901 having a transparent hood without transmission through the transparent wall of the transparent hood 905.

In a case where the organic tissue X in the body is observed with the hard endoscope 902 in the sheath 901 having a transparent hood through the transparent wall of the transparent hood 905, organic tissue X in closely contact with the transparent hood 905 can be observed clearly. However, the visual field of the organic tissue X apart from the transparent hood 905 is unsatisfactory to easily observe the organic tissue X. Therefore, the structure of this embodiment in which the movable hood 908 is opened downwards with respect to the fixed hood 907 enables the organic tissue X, intended to be observed, to be directly observed with the hard endoscope 902. Thus, the organic tissue X can be observed and treated satisfactorily. In a case where the fogging of the surface of the glass of the observation optical system of the endoscope 902 and the visual field of the hard endoscope 902 has become unsatisfactory, $CO_2$ gas or the like is supplied in a state where the movable hood 908 of the transparent hood 905 is slightly opened. Thus, fogging of the surface of the glass of the observation optical system can effectively be overcome. A fact has been known that dry gas is sprayed against the surface of the glass of the observation optical system at the leading end of the hard endoscope 902 to prevent fogging. However, this embodiment has the structure such that the portion around the leading end of the hard endoscope 902 is surrounded by the transparent hood 905 enables the surface of the glass of the observation optical system at the leading end of the endoscope 902 to be efficiently exposed to dry gas only by supplying a little quantity of dry gas into a small space formed in the transparent hood 905. Therefore, fogging can further effectively be overcome and prevented.

Thus, the foregoing structure attains the following advantages. That is, since the bipolar type first electrode 917 and the second electrode 918 forming the incising and coagulating means are provided for the edge portion 916 of the movable hood 908 of the transparent hood 905, the organic tissue X can be incised and coagulated by allowing the high-frequency cauterization current to flow between the first electrode 917 and the second electrode 918 during the operation of inserting the hard endoscope 902 into the body. Therefore, the organic tissue X can efficiently be dissected. Since the surface area of the first electrode 917 is made to be smaller than the second electrode 918 to raise the density of the current per unit area, the organic tissue X can be cauterized concentrically in the portion near the first electrode 917. Therefore, the organic tissue X can efficiently be dissected while necessitating only a small incision and coagulation ranges.

Since the organic tissue X can directly be observed with the eye with the hard endoscope 902 in the sheath 901 having a transparent hood through the transparent wall of the transparent hood 905 when the operation of excising the organic tissue X is performed, the operation of excising the organic tissue X and the operation of stopping bleeding can safely and easily be performed. Since the movable hood 908 is opened downwards with respect to the fixed hood 907 after the organic tissue X has been dissected, the organic tissue X intended to be observed can be observed directly with the hard endoscope 902. Therefore, the organic tissue X can directly be observed with the hard endoscope 902 in the sheath 901 having a transparent hood without transmission through the transparent wall of the transparent hood 905. Therefore, a clear visual field can be obtained through the hard endoscope 902. Since $CO_2$ gas or the like is supplied into the body through the inner cylinder 903 in a state where the movable hood 908 has been opened with respect to the fixed hood 907, the dissected portion can further be expanded due to the supply of the gas. Therefore, the space S in the body required to observe and treat the spine Y can satisfactorily be maintained. Since the $CO_2$ gas is supplied into the body through the inner cylinder 903, fogging of the surface of the glass of the observation optical system of the hard endoscope 902 can be overcome and prevented.

Although this embodiment has the structure such that the bipolar type first electrode 917 and the second electrode 918 forming the incising and coagulating means are provided for the edge portion 916 of the movable hood 908 of the transparent hood 905, the incising and coagulating means may be formed by a monopolar type structure including one unified electrode while having a similar structure. Although this embodiment has the structure such that the bipolar type first electrode 917 and the second electrode 918 are directly secured to the surface of the movable hood 908 of the transparent hood 905, a heat insulating material member made of fluorine resin or ceramic may be disposed between the movable hood 908 and the electrodes 917 and 918. If the transparent heating insulating material member made of the fluorine resin is employed, the visual field of the hard endoscope 902 cannot be deteriorated. In place of the electrodes 917 and 918, an antenna for generating microwaves may be employed to obtain a similar effect.

FIG. 108A shows a second embodiment of the endoscope hood. A transparent sheath 951, which is an endoscope hood, has a sheath body 952 in the form of a cylindrical shape having a closed leading end formed into a conical shape and made of a transparent material. A heat generating means (incising and coagulating means) 953 is attached to the leading end of the sheath body 952. As the heat generating means 953, a structure is employed in which a heater for generating heat when an electric current is allowed to flow is coated with, for example, a fluorine resin to prevent burning. The heat generating means 953 is, through a lead wire 954 disposed on the outer surface of the sheath body 952, connected to a connector 955 for establishing the connection with the power source. The lead wire 954 may be embedded in the outer surface of the sheath body 952 or disposed in the sheath body 952. Therefore, the foregoing structure enables the organic tissue to be dissected by pushing in the sheath body 952 in a state where the leading end of the sheath body 952 of the transparent sheath 951 is in contact with the organic tissue. By allowing electric current to flow to the heat generating means 953 at the leading end of the sheath body 952, the organic tissue can be cauterized or stopping of bleeding can be stopped. Although the second embodiment has the structure such that the heat generating means 953 is directly secured to the surface of the sheath body 952 of the transparent sheath 951, a heat insulating material member, made of a fluorine resin or ceramic may be inserted between the sheath body 952 and the heat generating means 953. If the transparent heat insulating material, such as the fluorine resin, is employed, an excellent visual field of the endoscope 902 can be obtained.

FIG. 108B shows a third embodiment of the endoscope hood. A transparent sheath, which is the endoscope hood, according to this embodiment is a supersonic sheath 961 capable of incising and coagulating an organic tissue. The supersonic sheath (incising and coagulating means) 961 is provided with an elongated pipe-like probe 963 into which an endoscope 962 can be inserted. A supersonic oscillator 964 is connected to the base portion of the probe 963. The supersonic oscillator 964 has an endoscope insertion hole 965 into which the endoscope 962 can be inserted. A transparent hood (hood body) 966 is attached to the leading end of the probe 963. Therefore, in the foregoing structure, supersonic oscillations generated by the supersonic oscillator 964 are transmitted to the transparent hood 966 through the probe 963. Thus, the organic tissue, with which the transparent hood 966 is in contact can be incised and coagulated.

FIG. 108C shows a fourth embodiment of the endoscope hood. This embodiment is a modification of the third embodiment. That is, this embodiment has the structure such that a cut portion 971 cut diagonally with respect to the axial line of a probe 963 according to this embodiment is formed at the leading end of the probe 963. Moreover, a transparent member (hood body) 972, which is an endoscope hood, is disposed on the inside of the cut portion 971 at the leading end of the probe 963. Therefore, the foregoing structure enables the organic tissue to be directly incised and coagulated by the probe 963. Therefore, the supersonic oscillation can efficiently be transmitted to the organic tissue. Note that the transmission efficiency of the supersonic oscillation is considerably affected by the material of the probe 963. Therefore, in the case where the probe 963 is direction brought into the organic tissue as is performed in this embodiment, excision and stopping of bleeding can effectively be performed as compared with the structure of, for example, the supersonic sheath 961 according to the third embodiment in which the supersonic oscillation from the probe 963 is transmitted to the organic tissue through the transparent hood 966.

FIG. 109 shows a fifth embodiment of the endoscope hood. A transparent sheath 981, which is the endoscope hood according to this embodiment, has a sheath body 982 provided with an endoscope insertion hole 983 having a closed leading end and an endoscope insertion hole 983 having two opened ends. The endoscope 985 is inserted into the endoscope insertion hole 983 and a supersonic probe (incising and coagulating means) 986 is inserted into the treatment tool hole 984. Therefore, the foregoing structure enables the organic tissue to be directly be incised and coagulated by the supersonic probe 986. Therefore, the supersonic oscillation can efficiently be transmitted to the organic tissue.

FIGS. 110A to 110D show a sixth embodiment of the endoscope hood. The endoscope hood according to this embodiment is a transparent sheath 993 in the form of a double cylinder consisting of an outer sheath 991 made of a transparent material and a transparent inner sheath 992 inserted into the outer sheath 991. The outer sheath 991 has, at the leading end thereof, a pushing portion 994 in the shape of a closed wedge. Moreover, a graven-line portion 995 extending in the axial direction of the outer sheath 991 is formed on the outer surface of the leading end of the outer sheath 991, as shown in FIG. 110C. The leading end of the inner sheath 992 is held in a state where the same has been inserted to a position near the pushing portion 994 of the outer sheath 991. An endoscope 996 can be inserted into the inner sheath 992. Therefore, in a state of the foregoing structure in which the leading end of the inner sheath 992 is, as shown in FIG. 110B, held while being inserted to a position near the pushing portion 994 of the outer sheath 991, the endoscope 996 is inserted into the inner sheath 992. Thus, state of the organic tissue can be observed with the endoscope 996 in the transparent sheath 993 through the transparent wall of the pushing portion 994 of the outer sheath 991. Since the graven-line portion 995 at the leading end of the outer sheath 991 has not been broken, the inside portion of the outer sheath 991 can be maintained to a water-tight state. Therefore, water introduction into the outer sheath 991 can be prevented. When the inner sheath 992 is slid forwards with respect to the outer sheath 991, the graven-line portion 995 of the outer sheath 991 is broken so that the inner sheath 992 is allowed to project, as shown in FIG. 110D. Therefore, in the foregoing case, the organic tissue can directly be observed with the endoscope 996 in the transparent sheath 993 without transmission of the transparent wall of the pushing portion 994 of the outer sheath 991. Thereof, a clear visual field can be obtained with the endoscope 996. By somewhat pulling inward the leading end of the endoscope 996 toward the inside portion of the inner sheath 992 from the leading end of the inner sheath 992, contamination of the endoscope 996 due to contact with the organic tissue can be prevented even if the outer sheath 991 has been opened. In place of the graven-line portion 995 formed in the outer sheath 991, slits may be formed in the outer surface of the outer sheath 991; and the slit portion is sealed by a sealing agent such as rubber or an adhesive agent to obtain a similar effect.

FIGS. 111A, 111B and 112 show a seventh embodiment of the endoscope hood. The endoscope hood according to this embodiment is a transparent sheath 1001 suitable to insert a diagonal-view or side-view type endoscope. The sheath body 1002 of the transparent sheath 1001 has a lower opening 1003 in the opening portion in the lower surface thereof. Moreover, a transparent shutter member 1004 is attached to the lower opening 1003 in such a manner that the shutter member 1004 can be opened and closed. A shutter guide groove 1005 is, as shown in FIG. 7, formed in the surface of the lower opening 1003. The shutter member 1004 is received in the shutter guide groove 1005. Note that a water sealing member, such as rubber or grease, maintains water sealing between the shutter guide groove 1005 and the shutter member 1004. A leading end of an operation rod 1006 is secured to the shutter member 1004. The base portion of the operation rod 1006 is connected to an operation ring 1007 slidably disposed on the outer surface of the sheath body 1002 of the transparent sheath 1001. By rearwards sliding the operation ring 1007, the shutter member 1004 is, as shown in FIG. 111B, rearwards slid so that the lower opening 1003 of the sheath body 1002 is opened.

Therefore, in a state of this embodiment, as shown in FIG. 11A, in which the lower opening 1003 of the sheath body 1002 of the transparent sheath 1001 is closed by the shutter member 1004, the diagonal-view type or side-view type endoscope is inserted. Thus, state of the organic tissue can be observed through the transparent wall of the shutter member 1004 with the diagonal-view type or side-view type endoscope. Since the space between the shutter guide groove 1005 and the shutter member 1004 is sealed against water by the sealing member against water, such as rubber or grease, the inside portion of the sheath body 1002 can be sealed against water. Thus, introduction of liquid into the sheath body 1002 can be prevented. By rearwards sliding the operation ring 1007 to rearwards slide the shutter member 1004 as shown in FIG. 111B, the lower opening 1003 of the sheath body 1002 is opened. Therefore, in the foregoing case, the organic tissue can directly be observed through the lower opening 1003 of the sheath body 1002 by the diagonal-view type or side-view type endoscope in the transparent sheath 1001 without transmission through the transparent wall of the shutter member 1004. Thus, a clear visual field can be obtained with the diagonal-view type or side-view type endoscope diagonal-view type or side-view type endoscope. Since the leading end of the diagonal-view type or side-view type endoscope is accommodated in the sheath body 1002 at this time, the leading end of the diagonal-view type or side-view type endoscope does not project over the sheath body 1002. Therefore, contamination due to contact of the diagonal-view type or side-view type endoscope with the organic tissue can be prevented during the period in which the shutter member 1004 is opened.

FIGS. 113A and 113B show an eighth embodiment of the endoscope hood. A sheath 1010, which is the endoscope hood according to this embodiment, is made of a transparent material and has a wedge-like leading end. The sheath 1010 has an opening 1011. An endoscope 1012 is a diagonal-view type endoscope. As shown in FIG. 113A, observation can be performed through an opening 1011. By rotating the endoscope 1012 by 180° to slightly rearwards move, observation through the transparent portion of the sheath 1010 can be performed, as shown in FIG. 113B.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An endoscope hood comprising:
    a hood body for covering at least a leading end portion of an insertion portion of an endoscope to be inserted into the body;
    an observation portion having an edge portion which is at a distal end thereof and is in contact with organic tissue in order to dissect the tissue, said observation portion being provided at a leading end of said hood body and made of a light transmissive material for maintaining a visual field for said endoscope; and
    incising and coagulating means provided slightly away from the edge portion on said observation portion of said hood body so as to incise and coagulate organic tissue.

2. An endoscope hood according to claim 1, wherein said incising and coagulating means includes energy supply means for outputting energy for incising and coagulating the organic tissue.

3. An endoscope hood, comprising:
    a hood body for covering at least a leading end portion of an insertion portion of an endoscope to be inserted into the body;
    an observation portion for said hood body and made of a light transmissive material for maintaining a visual field for said endoscope; and
    incising and coagulating means provided for said hood body so as to incise and coagulate organic tissue,
    wherein said incising and coagulating means further comprises:
        outputting means for releasing energy for incision and coagulation, and
        energy supply means for supplying energy to the outputting means, and
    wherein said hood body has an opening portion which can be opened and closed.

4. An endoscope hood according to claim 3, wherein said opening portion is opened within the visual field of said endoscope to permit observation with said endoscope to be performed without said observation portion.

5. An endoscope hood according to claim 4, wherein said opening portion has sealing means against fluid for preventing introduction of liquid into the hood body.

6. An endoscope hood according to claim 5, wherein said sealing means against fluid is a rubber member.

7. An endoscope hood according to claim 5, wherein said sealing means against fluid is grease.

8. An endoscope hood according to claim 5, wherein said sealing means against fluid is broken partially to form an opening in said hood body.

9. An endoscope hood according to claim 2, wherein said energy supply means has at least one electrode for supplying high-frequency cauterization current.

10. An endoscope hood according to claim 9, wherein said electrode is a bipolar electrode.

11. An endoscope hood according to claim 9, wherein said electrode is a monopolar electrode.

12. An endoscope hood according to claim 2, wherein said energy supply means consists of a member for electrically generating heat.

13. An endoscope hood, comprising:
    a hood body for covering at least a leading end portion of an insertion portion of an endoscope to be inserted into the body;
    an observation portion for said hood body and made of a light transmissive material for maintaining a visual field for said endoscope; and
    incising and coagulating means provided for said hood body so as to incise and coagulate organic tissue,
    wherein said incising and coagulating means further comprises:
        outputting means for releasing energy for incision and coagulation, and energy supply means for supplying energy to the outputting means, and wherein said energy supply means has means for generating supersonic oscillation.

14. An endoscope hood, comprising:

a hood body for covering at least a leading end portion of an insertion portion of an endoscope to be inserted into the body;

an observation portion for said hood body and made of a light transmissive material for maintaining a visual field for said endoscope; and incising and coagulating means provided for said hood body so as to incise and coagulate organic tissue, wherein said incising and coagulating means further comprises:
 outputting means for releasing energy for incision and coagulation, and
 energy supply means for supplying energy to the outputting means, and wherein said energy supply means has means for transmitting microwaves.

15. An endoscope hood according to claim 9, wherein said hood body has an edge portion, and said electrode is disposed adjacent to said edge portion.

16. An endoscope hood according to claim 9, wherein the width of said electrode is smaller than the diameter of said hood body.

17. An endoscope hood according to claim 2, wherein said energy supply means has a first electrode and a second electrode for supplying high-frequency cauterization current, and the surface area of said first electrode is smaller than that of said second electrode.

18. An endoscope hood according to claim 17, wherein said hood body has an edge portion and said first electrode is disposed adjacent to said edge portion.

19. An endoscope hood according to claim 1, wherein said hood body has fluid supply means therein.

20. An endoscope hood comprising:

a hood body for covering at least a leading end portion of an insertion portion of an endoscope to be inserted into the body;

an observation portion for said hood body and made of a light transmissive material for maintaining a visual field for said endoscope; and incising and coagulating means provided for said hood body so as to incise and coagulate organic tissue, wherein said hood body has an opening portion at the leading end from which said incising and coagulating means goes in and out.

* * * * *

UNITED STATES PATENT AND TRADEMARK OFFICE
CERTIFICATE OF CORRECTION

PATENT NO. : 6,019,720
DATED : February 1, 2000
INVENTOR(S) : Shiro BITO

It is certified that error appears in the above-indentified patent and that said Letters Patent is hereby corrected as shown below:

On the Title Page

Item [56] References Cited, under "U.S. PATENT DOCUMENTS",
insert --5,674,184  10/1997  Hassler, Jr.
5,681,262  10/1997  Isse--;

Item [57] ABSTRACT, line 1, change "including" to --includes--.

Signed and Sealed this

Fifteenth Day of May, 2001

Attest:

NICHOLAS P. GODICI

Attesting Officer         Acting Director of the United States Patent and Trademark Office